United States Patent
Faltys et al.

(10) Patent No.: US 11,383,091 B2
(45) Date of Patent: Jul. 12, 2022

(54) IMPLANTABLE NEUROSTIMULATOR HAVING POWER CONTROL AND THERMAL REGULATION AND METHODS OF USE

(71) Applicant: SetPoint Medical Corporation, Valencia, CA (US)

(72) Inventors: Michael A. Faltys, Valencia, CA (US); Jesse M. Simon, Los Angeles, CA (US)

(73) Assignee: SetPoint Medical Corporation, Valencia, CA (US)

( * ) Notice: Subject to any disclaimer, the term of this patent is extended or adjusted under 35 U.S.C. 154(b) by 199 days.

(21) Appl. No.: 16/728,880

(22) Filed: Dec. 27, 2019

(65) Prior Publication Data

US 2020/0206515 A1    Jul. 2, 2020

Related U.S. Application Data

(62) Division of application No. 15/415,764, filed on Jan. 25, 2017, now Pat. No. 10,583,304.
(Continued)

(51) Int. Cl.
*A61N 1/378* (2006.01)
*A61N 1/375* (2006.01)
(Continued)

(52) U.S. Cl.
CPC ......... *A61N 1/3787* (2013.01); *A61N 1/3606* (2013.01); *A61N 1/3756* (2013.01); *A61N 1/37205* (2013.01); *A61N 1/36053* (2013.01)

(58) Field of Classification Search
CPC ............. A61N 1/3787; A61N 1/3606; A61N 1/37205; A61N 1/3756; A61N 1/36053
See application file for complete search history.

(56) References Cited

U.S. PATENT DOCUMENTS

| 2,164,121 A | 6/1939 | Pescador |
| 3,363,623 A | 1/1968 | Atwell |
| (Continued) | | |

FOREIGN PATENT DOCUMENTS

| CN | 201230913 A | 5/2009 |
| CN | 101528303 A | 9/2009 |
| (Continued) | | |

OTHER PUBLICATIONS

US 6,184,239 B1, 02/2001, Puskas (withdrawn)
(Continued)

*Primary Examiner* — Catherine M Voorhees
*Assistant Examiner* — Roland Dinga
(74) *Attorney, Agent, or Firm* — Shay Glenn LLP

(57) ABSTRACT

Leadless, implantable microstimulators for treating chronic inflammation. These devices can include a static magnetic field detector (e.g., non-Hall effect sensors/detectors, including those based on a Wiegand effect or generating pulses at a predetermined frequency range and using a detection circuit to determine the decay rate of the pulses), to trigger an emergency shut off of the micro stimulator. Also described are methods and apparatuses for regulating the temperature of an implant based applied power from a charger (e.g., voltage across the charger when unloaded and when loaded by the implant) to yield a power control loop correlated with the power drawn by the implant to determine temperature of the implant. A negotiation protocol can exchange data between the charger and the implant (e.g., type of charger, type of implant, nature of the coupling between the two, etc.) to set target power control loop parameters to estimate and regulate implant temperature.

20 Claims, 19 Drawing Sheets

Related U.S. Application Data

(60) Provisional application No. 62/286,951, filed on Jan. 25, 2016, provisional application No. 62/340,937, filed on May 24, 2016, provisional application No. 62/286,955, filed on Jan. 25, 2016.

(51) Int. Cl.
*A61N 1/372* (2006.01)
*A61N 1/36* (2006.01)

(56) References Cited

U.S. PATENT DOCUMENTS

| | | |
|---|---|---|
| 3,631,534 A | 12/1971 | Hirota et al. |
| 4,073,296 A | 2/1978 | McCall |
| 4,098,277 A | 7/1978 | Mendell |
| 4,305,402 A | 12/1981 | Katims |
| 4,503,863 A | 3/1985 | Katims |
| 4,573,481 A | 3/1986 | Bullara |
| 4,590,946 A | 5/1986 | Loeb |
| 4,632,095 A | 12/1986 | Libin |
| 4,649,936 A | 3/1987 | Ungar et al. |
| 4,702,254 A | 10/1987 | Zabara |
| 4,840,793 A | 6/1989 | Todd, III et al. |
| 4,867,164 A | 9/1989 | Zabara |
| 4,929,734 A | 5/1990 | Coughenour et al. |
| 4,930,516 A | 6/1990 | Alfano et al. |
| 4,935,234 A | 6/1990 | Todd, III et al. |
| 4,979,511 A | 12/1990 | Terry, Jr. |
| 4,991,578 A | 2/1991 | Cohen |
| 5,019,648 A | 5/1991 | Schlossman et al. |
| 5,025,807 A | 6/1991 | Zabara |
| 5,038,781 A | 8/1991 | Lynch |
| 5,049,659 A | 9/1991 | Cantor |
| 5,073,560 A | 12/1991 | Wu et al. |
| 5,106,853 A | 4/1992 | Showell et al. |
| 5,111,815 A | 5/1992 | Mower |
| 5,154,172 A | 10/1992 | Terry, Jr. et al. |
| 5,175,166 A | 12/1992 | Dunbar et al. |
| 5,179,950 A | 1/1993 | Stanislaw |
| 5,186,170 A | 2/1993 | Varrichio et al. |
| 5,188,104 A | 2/1993 | Wernicke et al. |
| 5,203,326 A | 4/1993 | Collins |
| 5,205,285 A | 4/1993 | Baker, Jr. |
| 5,215,086 A | 6/1993 | Terry, Jr. et al. |
| 5,215,089 A | 6/1993 | Baker, Jr. |
| 5,222,494 A | 6/1993 | Baker, Jr. |
| 5,231,988 A | 8/1993 | Wernicke et al. |
| 5,235,980 A | 8/1993 | Varrichio et al. |
| 5,237,991 A | 8/1993 | Baker et al. |
| 5,251,634 A | 10/1993 | Weinberg |
| 5,263,480 A | 11/1993 | Wernicke et al. |
| 5,269,303 A | 12/1993 | Wernicke et al. |
| 5,299,569 A | 4/1994 | Wernicke et al. |
| 5,304,206 A | 4/1994 | Baker, Jr. et al. |
| 5,330,507 A | 7/1994 | Schwartz |
| 5,330,515 A | 7/1994 | Rutecki et al. |
| 5,335,657 A | 8/1994 | Terry, Jr. et al. |
| 5,344,438 A | 9/1994 | Testerman et al. |
| 5,351,394 A | 10/1994 | Weinberg |
| 5,403,845 A | 4/1995 | Dunbar et al. |
| 5,458,625 A | 10/1995 | Kendall |
| 5,472,841 A | 12/1995 | Jayasena et al. |
| 5,487,756 A | 1/1996 | Kallesoe et al. |
| 5,496,938 A | 3/1996 | Gold et al. |
| 5,503,978 A | 4/1996 | Schneider et al. |
| 5,531,778 A | 7/1996 | Maschino et al. |
| 5,540,730 A | 7/1996 | Terry, Jr. et al. |
| 5,540,734 A | 7/1996 | Zabara |
| 5,567,588 A | 10/1996 | Gold |
| 5,567,724 A | 10/1996 | Kelleher |
| 5,571,150 A | 11/1996 | Wernicke et al. |
| 5,580,737 A | 12/1996 | Polisky et al. |
| 5,582,981 A | 12/1996 | Toole et al. |
| 5,604,231 A | 2/1997 | Smith et al. |
| 5,607,459 A | 3/1997 | Paul et al. |
| 5,611,350 A | 3/1997 | John |
| 5,618,818 A | 4/1997 | Ojo et al. |
| 5,629,285 A | 5/1997 | Black et al. |
| 5,637,459 A | 6/1997 | Burke et al. |
| 5,651,378 A | 7/1997 | Matheny et al. |
| 5,654,151 A | 8/1997 | Allen et al. |
| 5,683,867 A | 11/1997 | Biesecker et al. |
| 5,690,681 A | 11/1997 | Geddes et al. |
| 5,700,282 A | 12/1997 | Zabara |
| 5,705,337 A | 1/1998 | Gold et al. |
| 5,707,400 A | 1/1998 | Terry, Jr. et al. |
| 5,709,853 A | 1/1998 | Iino et al. |
| 5,712,375 A | 1/1998 | Jensen et al. |
| 5,718,912 A | 2/1998 | Thompson et al. |
| 5,726,017 A | 3/1998 | Lochrie et al. |
| 5,726,179 A | 3/1998 | Messer, Jr. et al. |
| 5,727,556 A | 3/1998 | Weth et al. |
| 5,733,255 A | 3/1998 | Dinh et al. |
| 5,741,802 A | 4/1998 | Kem et al. |
| 5,773,598 A | 6/1998 | Burke et al. |
| 5,786,462 A | 7/1998 | Schneider et al. |
| 5,788,656 A | 8/1998 | Mino |
| 5,792,210 A | 8/1998 | Wamubu et al. |
| 5,824,027 A | 10/1998 | Hoffer et al. |
| 5,853,005 A | 12/1998 | Scanlon |
| 5,854,289 A | 12/1998 | Bianchi et al. |
| 5,902,814 A | 5/1999 | Gordon et al. |
| 5,913,876 A | 6/1999 | Taylor et al. |
| 5,916,239 A | 6/1999 | Geddes et al. |
| 5,919,216 A | 7/1999 | Houben et al. |
| 5,928,272 A | 7/1999 | Adkins et al. |
| 5,964,794 A | 10/1999 | Bolz et al. |
| 5,977,144 A | 11/1999 | Meyer et al. |
| 5,994,330 A | 11/1999 | El Khoury |
| 6,002,964 A | 12/1999 | Feler et al. |
| 6,006,134 A | 12/1999 | Hill et al. |
| 6,017,891 A | 1/2000 | Eibl et al. |
| 6,028,186 A | 2/2000 | Tasset et al. |
| 6,051,017 A | 4/2000 | Loeb et al. |
| 6,083,696 A | 7/2000 | Biesecker et al. |
| 6,083,905 A | 7/2000 | Voorberg et al. |
| 6,096,728 A | 8/2000 | Collins et al. |
| 6,104,956 A | 8/2000 | Naritoku et al. |
| 6,110,900 A | 8/2000 | Gold et al. |
| 6,110,914 A | 8/2000 | Phillips et al. |
| 6,117,837 A | 9/2000 | Tracey et al. |
| 6,124,449 A | 9/2000 | Gold et al. |
| 6,127,119 A | 10/2000 | Stephens et al. |
| 6,140,490 A | 10/2000 | Biesecker et al. |
| 6,141,590 A | 10/2000 | Renirie et al. |
| 6,147,204 A | 11/2000 | Gold et al. |
| 6,159,145 A | 12/2000 | Satoh |
| 6,164,284 A | 12/2000 | Schulman et al. |
| 6,166,048 A | 12/2000 | Bencherif |
| 6,168,778 B1 | 1/2001 | Janjic et al. |
| 6,171,795 B1 | 1/2001 | Korman et al. |
| 6,205,359 B1 | 3/2001 | Boveja |
| 6,208,894 B1 | 3/2001 | Schulman et al. |
| 6,208,902 B1 | 3/2001 | Boveja |
| 6,210,321 B1 | 4/2001 | Di Mino et al. |
| 6,224,862 B1 | 5/2001 | Turecek et al. |
| 6,233,488 B1 | 5/2001 | Hess |
| 6,266,564 B1 | 7/2001 | Hill et al. |
| 6,269,270 B1 | 7/2001 | Boveja |
| 6,304,775 B1 | 10/2001 | Iasemidis et al. |
| 6,308,104 B1 | 10/2001 | Taylor et al. |
| 6,337,997 B1 | 1/2002 | Rise |
| 6,339,725 B1 | 1/2002 | Naritoku et al. |
| 6,341,236 B1 | 1/2002 | Osorio et al. |
| 6,356,787 B1 | 3/2002 | Rezai et al. |
| 6,356,788 B2 | 3/2002 | Boveja |
| 6,381,499 B1 | 4/2002 | Taylor et al. |
| 6,405,732 B1 | 6/2002 | Edwards et al. |
| 6,407,095 B1 | 6/2002 | Lochead et al. |
| 6,428,484 B1 | 8/2002 | Battmer et al. |
| 6,429,217 B1 | 8/2002 | Puskas |
| 6,447,443 B1 | 9/2002 | Keogh et al. |
| 6,449,507 B1 | 9/2002 | Hill et al. |

(56) References Cited

U.S. PATENT DOCUMENTS

| | | |
|---|---|---|
| 6,473,644 B1 | 10/2002 | Terry, Jr. et al. |
| 6,479,523 B1 | 11/2002 | Puskas |
| 6,487,446 B1 | 11/2002 | Hill et al. |
| 6,511,500 B1 | 1/2003 | Rahme |
| 6,528,529 B1 | 3/2003 | Brann et al. |
| 6,532,388 B1 | 3/2003 | Hill et al. |
| 6,542,774 B2 | 4/2003 | Hill et al. |
| 6,556,868 B2 | 4/2003 | Naritoku et al. |
| 6,564,102 B1 | 5/2003 | Boveja |
| 6,587,719 B1 | 7/2003 | Barrett et al. |
| 6,587,727 B2 | 7/2003 | Osorio et al. |
| 6,600,956 B2 | 7/2003 | Maschino et al. |
| 6,602,891 B2 | 8/2003 | Messer et al. |
| 6,609,025 B2 | 8/2003 | Barrett et al. |
| 6,610,713 B2 | 8/2003 | Tracey |
| 6,611,715 B1 | 8/2003 | Boveja |
| 6,615,081 B1 | 9/2003 | Boveja |
| 6,615,085 B1 | 9/2003 | Boveja |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,628,987 B1 | 9/2003 | Hill et al. |
| 6,633,779 B1 | 10/2003 | Schuler et al. |
| 6,656,960 B2 | 12/2003 | Puskas |
| 6,668,191 B1 | 12/2003 | Boveja |
| 6,671,556 B2 | 12/2003 | Osorio et al. |
| 6,684,105 B2 | 1/2004 | Cohen et al. |
| 6,690,973 B2 | 2/2004 | Hill et al. |
| 6,718,208 B2 | 4/2004 | Hill et al. |
| 6,721,603 B2 | 4/2004 | Zabara et al. |
| 6,735,471 B2 | 5/2004 | Hill et al. |
| 6,735,475 B1 | 5/2004 | Whitehurst et al. |
| 6,760,626 B1 | 7/2004 | Boveja |
| 6,778,854 B2 | 8/2004 | Puskas |
| 6,804,558 B2 | 10/2004 | Haller et al. |
| RE38,654 E | 11/2004 | Hill et al. |
| 6,826,428 B1 | 11/2004 | Chen et al. |
| 6,832,114 B1 | 12/2004 | Whitehurst et al. |
| 6,838,471 B2 | 1/2005 | Tracey |
| RE38,705 E | 2/2005 | Hill et al. |
| 6,879,859 B1 | 4/2005 | Boveja |
| 6,885,888 B2 | 4/2005 | Rezai |
| 6,901,294 B1 | 5/2005 | Whitehurst et al. |
| 6,904,318 B2 | 6/2005 | Hill et al. |
| 6,920,357 B2 | 7/2005 | Osoro et al. |
| 6,928,320 B2 | 8/2005 | King |
| 6,934,583 B2 | 8/2005 | Weinberg et al. |
| 6,937,903 B2 | 8/2005 | Schuler et al. |
| 6,961,618 B2 | 11/2005 | Osorio et al. |
| 6,978,787 B1 | 12/2005 | Broniatowski |
| 7,011,638 B2 | 3/2006 | Schuler et al. |
| 7,054,686 B2 | 5/2006 | MacDonald |
| 7,054,692 B1 | 5/2006 | Whitehurst et al. |
| 7,058,447 B2 | 6/2006 | Hill et al. |
| 7,062,320 B2 | 6/2006 | Ehlinger, Jr. |
| 7,069,082 B2 | 6/2006 | Lindenthaler |
| 7,072,720 B2 | 7/2006 | Puskas |
| 7,076,307 B2 | 7/2006 | Boveja et al. |
| 7,142,910 B2 | 11/2006 | Puskas |
| 7,142,917 B2 | 11/2006 | Fukui |
| 7,149,574 B2 | 12/2006 | Yun et al. |
| 7,155,279 B2 | 12/2006 | Whitehurst et al. |
| 7,155,284 B1 | 12/2006 | Whitehurst et al. |
| 7,167,750 B2 | 1/2007 | Knudson et al. |
| 7,167,751 B1 | 1/2007 | Whitehurst et al. |
| 7,174,218 B1 | 2/2007 | Kuzma |
| 7,184,828 B2 | 2/2007 | Hill et al. |
| 7,184,829 B2 | 2/2007 | Hill et al. |
| 7,191,012 B2 | 3/2007 | Boveja et al. |
| 7,204,815 B2 | 4/2007 | Connor |
| 7,209,787 B2 | 4/2007 | DiLorenzo |
| 7,225,019 B2 | 5/2007 | Jahns et al. |
| 7,228,167 B2 | 6/2007 | Kara et al. |
| 7,238,715 B2 | 7/2007 | Tracey et al. |
| 7,242,984 B2 | 7/2007 | DiLorenzo |
| 7,269,457 B2 | 9/2007 | Shafer et al. |
| 7,345,178 B2 | 3/2008 | Nunes et al. |
| 7,373,204 B2 | 5/2008 | Gelfand et al. |
| 7,389,145 B2 | 6/2008 | Kilgore et al. |
| 7,454,245 B2 | 11/2008 | Armstrong et al. |
| 7,467,016 B2 | 12/2008 | Colborn |
| 7,544,497 B2 | 6/2009 | Sinclair et al. |
| 7,561,918 B2 | 7/2009 | Armstrong et al. |
| 7,711,432 B2 | 5/2010 | Thimineur et al. |
| 7,729,760 B2 | 6/2010 | Patel et al. |
| 7,751,891 B2 | 7/2010 | Armstrong et al. |
| 7,776,326 B2 | 8/2010 | Milbrandt et al. |
| 7,797,058 B2 | 9/2010 | Mrva et al. |
| 7,819,883 B2 | 10/2010 | Westlund et al. |
| 7,822,486 B2 | 10/2010 | Foster et al. |
| 7,829,556 B2 | 11/2010 | Bemis et al. |
| 7,869,885 B2 | 1/2011 | Begnaud et al. |
| 7,937,145 B2 | 5/2011 | Dobak |
| 7,962,220 B2 | 6/2011 | Kolafa et al. |
| 7,974,701 B2 | 7/2011 | Armstrong |
| 7,974,707 B2 | 7/2011 | Inman |
| 7,996,088 B2 | 8/2011 | Marrosu et al. |
| 7,996,092 B2 | 8/2011 | Mrva et al. |
| 8,019,419 B1 | 9/2011 | Panescu et al. |
| 8,060,208 B2 | 11/2011 | Kilgore et al. |
| 8,103,349 B2 | 1/2012 | Donders et al. |
| 8,165,668 B2 | 4/2012 | Dacey, Jr. et al. |
| 8,180,446 B2 | 5/2012 | Dacey, Jr. et al. |
| 8,180,447 B2 | 5/2012 | Dacey et al. |
| 8,195,287 B2 | 6/2012 | Dacey, Jr. et al. |
| 8,214,056 B2 | 7/2012 | Hoffer et al. |
| 8,233,982 B2 | 7/2012 | Libbus |
| 8,391,970 B2 | 3/2013 | Tracey et al. |
| 8,412,338 B2 | 4/2013 | Faltys |
| 8,571,654 B2 | 10/2013 | Libbus et al. |
| 8,577,458 B1 | 11/2013 | Libbus et al. |
| 8,600,505 B2 | 12/2013 | Libbus et al. |
| 8,612,002 B2 | 12/2013 | Faltys et al. |
| 8,630,709 B2 | 1/2014 | Libbus et al. |
| 8,688,212 B2 | 4/2014 | Libbus et al. |
| 8,700,150 B2 | 4/2014 | Libbus et al. |
| 8,729,129 B2 | 5/2014 | Tracey et al. |
| 8,788,034 B2 | 7/2014 | Levine et al. |
| 8,843,210 B2 | 9/2014 | Simon et al. |
| 8,855,767 B2 | 10/2014 | Faltys et al. |
| 8,886,339 B2 | 11/2014 | Faltys et al. |
| 8,914,114 B2 | 12/2014 | Tracey et al. |
| 8,918,178 B2 | 12/2014 | Simon et al. |
| 8,918,191 B2 | 12/2014 | Libbus et al. |
| 8,923,964 B2 | 12/2014 | Libbus et al. |
| 8,983,628 B2 | 3/2015 | Simon et al. |
| 8,983,629 B2 | 3/2015 | Simon et al. |
| 8,996,116 B2 | 3/2015 | Faltys et al. |
| 9,114,262 B2 | 8/2015 | Libbus et al. |
| 9,162,064 B2 | 10/2015 | Faltys et al. |
| 9,174,041 B2 | 11/2015 | Faltys et al. |
| 9,211,409 B2 | 12/2015 | Tracey et al. |
| 9,211,410 B2 | 12/2015 | Levine et al. |
| 9,254,383 B2 | 2/2016 | Simon et al. |
| 9,272,143 B2 | 3/2016 | Libbus et al. |
| 9,358,381 B2 | 6/2016 | Simon et al. |
| 9,399,134 B2 | 7/2016 | Simon et al. |
| 9,403,001 B2 | 8/2016 | Simon et al. |
| 9,409,024 B2 | 8/2016 | KenKnight et al. |
| 9,415,224 B2 | 8/2016 | Libbus et al. |
| 9,452,290 B2 | 9/2016 | Libbus et al. |
| 9,504,832 B2 | 11/2016 | Libbus et al. |
| 9,511,228 B2 | 12/2016 | Amurthur et al. |
| 9,533,153 B2 | 1/2017 | Libbus et al. |
| 9,572,983 B2 | 2/2017 | Levine et al. |
| 9,662,490 B2 | 5/2017 | Tracey et al. |
| 9,700,716 B2 | 7/2017 | Faltys et al. |
| 9,833,621 B2 | 12/2017 | Levine |
| 9,849,286 B2 | 12/2017 | Levine et al. |
| 9,987,492 B2 | 6/2018 | Tracey et al. |
| 9,993,651 B2 | 6/2018 | Faltys et al. |
| 10,166,395 B2 | 1/2019 | Tracey et al. |
| 10,220,203 B2 | 3/2019 | Faltys et al. |
| 10,449,358 B2 | 10/2019 | Levine et al. |

(56) References Cited

U.S. PATENT DOCUMENTS

| | | |
|---|---|---|
| 10,561,846 B2 | 2/2020 | Tracey et al. |
| 10,583,304 B2 | 3/2020 | Faltys et al. |
| 2001/0002441 A1 | 5/2001 | Boveja |
| 2001/0034542 A1 | 10/2001 | Mann |
| 2002/0026141 A1 | 2/2002 | Houben et al. |
| 2002/0040035 A1 | 4/2002 | Myers et al. |
| 2002/0077675 A1 | 6/2002 | Greenstein |
| 2002/0086871 A1 | 7/2002 | O'Neill et al. |
| 2002/0095139 A1 | 7/2002 | Keogh et al. |
| 2002/0099417 A1 | 7/2002 | Naritoku et al. |
| 2002/0138075 A1 | 9/2002 | Edwards et al. |
| 2002/0138109 A1 | 9/2002 | Keogh et al. |
| 2002/0193859 A1 | 12/2002 | Schulman et al. |
| 2002/0198570 A1 | 12/2002 | Puskas |
| 2003/0018367 A1 | 1/2003 | DiLorenzo |
| 2003/0032852 A1* | 2/2003 | Perreault ............... A61N 2/006 600/9 |
| 2003/0045909 A1 | 3/2003 | Gross et al. |
| 2003/0088301 A1 | 5/2003 | King |
| 2003/0191404 A1 | 10/2003 | Klein |
| 2003/0194752 A1 | 10/2003 | Anderson et al. |
| 2003/0195578 A1 | 10/2003 | Perron et al. |
| 2003/0212440 A1 | 11/2003 | Boveja |
| 2003/0229380 A1 | 12/2003 | Adams et al. |
| 2003/0236557 A1 | 12/2003 | Whitehurst et al. |
| 2003/0236558 A1 | 12/2003 | Whitehurst et al. |
| 2004/0002546 A1 | 1/2004 | Altschuler |
| 2004/0015202 A1 | 1/2004 | Chandler et al. |
| 2004/0015204 A1 | 1/2004 | Whitehurst et al. |
| 2004/0015205 A1 | 1/2004 | Whitehurst et al. |
| 2004/0024422 A1 | 2/2004 | Hill et al. |
| 2004/0024428 A1 | 2/2004 | Barrett et al. |
| 2004/0024439 A1 | 2/2004 | Riso |
| 2004/0030362 A1 | 2/2004 | Hill et al. |
| 2004/0039427 A1 | 2/2004 | Barrett et al. |
| 2004/0048795 A1 | 3/2004 | Ivanova et al. |
| 2004/0049121 A1 | 3/2004 | Yaron |
| 2004/0049240 A1 | 3/2004 | Gerber et al. |
| 2004/0059383 A1 | 3/2004 | Puskas |
| 2004/0111139 A1 | 6/2004 | McCreery et al. |
| 2004/0138517 A1 | 7/2004 | Osorio et al. |
| 2004/0138518 A1 | 7/2004 | Rise et al. |
| 2004/0138536 A1 | 7/2004 | Frei et al. |
| 2004/0146949 A1 | 7/2004 | Tan et al. |
| 2004/0153127 A1 | 8/2004 | Gordon et al. |
| 2004/0158119 A1 | 8/2004 | Osorio et al. |
| 2004/0162584 A1 | 8/2004 | Hill et al. |
| 2004/0172074 A1 | 9/2004 | Yoshihito |
| 2004/0172085 A1 | 9/2004 | Knudson et al. |
| 2004/0172086 A1 | 9/2004 | Knudson et al. |
| 2004/0172088 A1 | 9/2004 | Knudson et al. |
| 2004/0172094 A1 | 9/2004 | Cohen et al. |
| 2004/0176812 A1 | 9/2004 | Knudson et al. |
| 2004/0178706 A1 | 9/2004 | D'Orso |
| 2004/0193231 A1 | 9/2004 | David et al. |
| 2004/0199209 A1 | 10/2004 | Hill et al. |
| 2004/0199210 A1 | 10/2004 | Shelchuk |
| 2004/0204355 A1 | 10/2004 | Tracey et al. |
| 2004/0215272 A1 | 10/2004 | Haubrich et al. |
| 2004/0215287 A1 | 10/2004 | Swoyer et al. |
| 2004/0236381 A1 | 11/2004 | Dinsmoor et al. |
| 2004/0236382 A1 | 11/2004 | Dinsmoor et al. |
| 2004/0240691 A1 | 12/2004 | Grafenberg |
| 2004/0243182 A1 | 12/2004 | Cohen et al. |
| 2004/0254612 A1 | 12/2004 | Ezra et al. |
| 2004/0267152 A1 | 12/2004 | Pineda |
| 2005/0021092 A1 | 1/2005 | Yun et al. |
| 2005/0021101 A1 | 1/2005 | Chen et al. |
| 2005/0027328 A1 | 2/2005 | Greenstein |
| 2005/0043774 A1 | 2/2005 | Devlin et al. |
| 2005/0049655 A1 | 3/2005 | Boveja et al. |
| 2005/0065553 A1 | 3/2005 | Ben Ezra et al. |
| 2005/0065573 A1 | 3/2005 | Rezai |
| 2005/0065575 A1 | 3/2005 | Dobak |
| 2005/0070970 A1 | 3/2005 | Knudson et al. |
| 2005/0070974 A1 | 3/2005 | Knudson et al. |
| 2005/0075701 A1 | 4/2005 | Shafer |
| 2005/0075702 A1 | 4/2005 | Shafer |
| 2005/0095246 A1 | 5/2005 | Shafer |
| 2005/0096707 A1 | 5/2005 | Hill et al. |
| 2005/0103351 A1 | 5/2005 | Stomberg et al. |
| 2005/0113894 A1 | 5/2005 | Zilberman et al. |
| 2005/0131467 A1 | 6/2005 | Boveja |
| 2005/0131486 A1 | 6/2005 | Boveja et al. |
| 2005/0131487 A1 | 6/2005 | Boveja |
| 2005/0131493 A1 | 6/2005 | Boveja et al. |
| 2005/0137644 A1 | 6/2005 | Boveja et al. |
| 2005/0137645 A1 | 6/2005 | Voipio et al. |
| 2005/0143781 A1 | 6/2005 | Carbunaru et al. |
| 2005/0143787 A1 | 6/2005 | Boveja et al. |
| 2005/0149126 A1 | 7/2005 | Libbus |
| 2005/0149129 A1 | 7/2005 | Libbus et al. |
| 2005/0149131 A1 | 7/2005 | Libbus et al. |
| 2005/0153885 A1 | 7/2005 | Yun et al. |
| 2005/0154425 A1* | 7/2005 | Boveja ............... A61N 1/36082 607/45 |
| 2005/0154426 A1 | 7/2005 | Boveja et al. |
| 2005/0165458 A1 | 7/2005 | Boveja et al. |
| 2005/0177200 A1 | 8/2005 | George et al. |
| 2005/0182288 A1 | 8/2005 | Zabara |
| 2005/0182467 A1 | 8/2005 | Hunter et al. |
| 2005/0187584 A1 | 8/2005 | Denker et al. |
| 2005/0187586 A1 | 8/2005 | David et al. |
| 2005/0187590 A1 | 8/2005 | Boveja et al. |
| 2005/0191661 A1 | 9/2005 | Gatanaga et al. |
| 2005/0192644 A1 | 9/2005 | Boveja et al. |
| 2005/0197600 A1 | 9/2005 | Schuler et al. |
| 2005/0197675 A1 | 9/2005 | David et al. |
| 2005/0197678 A1 | 9/2005 | Boveja et al. |
| 2005/0203501 A1 | 9/2005 | Aldrich et al. |
| 2005/0209654 A1 | 9/2005 | Boveja et al. |
| 2005/0216064 A1 | 9/2005 | Heruth et al. |
| 2005/0216070 A1 | 9/2005 | Boveja et al. |
| 2005/0216071 A1 | 9/2005 | Devlin et al. |
| 2005/0240229 A1 | 10/2005 | Whitehurst et al. |
| 2005/0240231 A1 | 10/2005 | Aldrich et al. |
| 2005/0240241 A1 | 10/2005 | Yun et al. |
| 2005/0240242 A1 | 10/2005 | DiLorenzo |
| 2005/0251220 A1 | 11/2005 | Barrett et al. |
| 2005/0251222 A1 | 11/2005 | Barrett et al. |
| 2005/0267542 A1 | 12/2005 | David et al. |
| 2005/0267547 A1 | 12/2005 | Knudson et al. |
| 2005/0277912 A1 | 12/2005 | John |
| 2005/0283198 A1 | 12/2005 | Haubrich et al. |
| 2006/0009815 A1 | 1/2006 | Boveja et al. |
| 2006/0015151 A1 | 1/2006 | Aldrich |
| 2006/0025828 A1 | 2/2006 | Armstrong et al. |
| 2006/0036293 A1 | 2/2006 | Whitehurst et al. |
| 2006/0052657 A9 | 3/2006 | Zabara |
| 2006/0052831 A1 | 3/2006 | Fukui |
| 2006/0052836 A1 | 3/2006 | Kim et al. |
| 2006/0058851 A1 | 3/2006 | Cigaina |
| 2006/0064137 A1 | 3/2006 | Stone |
| 2006/0064139 A1 | 3/2006 | Chung et al. |
| 2006/0074450 A1 | 4/2006 | Boveja et al. |
| 2006/0074473 A1 | 4/2006 | Gertner |
| 2006/0079936 A1 | 4/2006 | Boveja et al. |
| 2006/0085046 A1 | 4/2006 | Rezai et al. |
| 2006/0095081 A1 | 5/2006 | Zhou et al. |
| 2006/0095090 A1 | 5/2006 | De Ridder |
| 2006/0100668 A1 | 5/2006 | Sen-David et al. |
| 2006/0106755 A1 | 5/2006 | Stuhec |
| 2006/0111644 A1 | 5/2006 | Guttag et al. |
| 2006/0111754 A1 | 5/2006 | Rezai et al. |
| 2006/0111755 A1 | 5/2006 | Stone et al. |
| 2006/0116739 A1 | 6/2006 | Betser et al. |
| 2006/0122675 A1 | 6/2006 | Libbus et al. |
| 2006/0129200 A1 | 6/2006 | Kurokawa |
| 2006/0129202 A1 | 6/2006 | Armstrong |
| 2006/0135998 A1 | 6/2006 | Libbus et al. |
| 2006/0136024 A1 | 6/2006 | Cohen |
| 2006/0142802 A1 | 6/2006 | Armstrong |
| 2006/0142822 A1 | 6/2006 | Tulgar |
| 2006/0149337 A1 | 7/2006 | John |

(56) References Cited

U.S. PATENT DOCUMENTS

| | | |
|---|---|---|
| 2006/0155495 A1 | 7/2006 | Osorio et al. |
| 2006/0161216 A1 | 7/2006 | John et al. |
| 2006/0161217 A1 | 7/2006 | Jaax et al. |
| 2006/0167497 A1 | 7/2006 | Armstrong et al. |
| 2006/0167498 A1 | 7/2006 | DiLorenzo |
| 2006/0167501 A1 | 7/2006 | Ben-David et al. |
| 2006/0173493 A1 | 8/2006 | Armstrong et al. |
| 2006/0173508 A1 | 8/2006 | Stone et al. |
| 2006/0178691 A1 | 8/2006 | Binmoeller |
| 2006/0178703 A1 | 8/2006 | Huston et al. |
| 2006/0178706 A1 | 8/2006 | Lisogurski et al. |
| 2006/0190044 A1 | 8/2006 | Libbus et al. |
| 2006/0200208 A1 | 9/2006 | Terry, Jr. et al. |
| 2006/0200219 A1 | 9/2006 | Thrope et al. |
| 2006/0206155 A1 | 9/2006 | Ben-David et al. |
| 2006/0206158 A1 | 9/2006 | Wu et al. |
| 2006/0229677 A1 | 10/2006 | Moffitt et al. |
| 2006/0229681 A1 | 10/2006 | Fischell |
| 2006/0241697 A1 | 10/2006 | Libbus et al. |
| 2006/0241699 A1 | 10/2006 | Libbus et al. |
| 2006/0247719 A1 | 11/2006 | Maschino et al. |
| 2006/0247721 A1 | 11/2006 | Maschino et al. |
| 2006/0247722 A1 | 11/2006 | Maschino et al. |
| 2006/0259077 A1 | 11/2006 | Pardo et al. |
| 2006/0259084 A1 | 11/2006 | Zhang et al. |
| 2006/0259085 A1 | 11/2006 | Zhang et al. |
| 2006/0259107 A1 | 11/2006 | Caparso et al. |
| 2006/0271115 A1 | 11/2006 | Ben-Ezra et al. |
| 2006/0282121 A1 | 12/2006 | Payne et al. |
| 2006/0282131 A1 | 12/2006 | Caparso et al. |
| 2006/0282145 A1 | 12/2006 | Caparso et al. |
| 2006/0287678 A1 | 12/2006 | Shafer |
| 2006/0287679 A1 | 12/2006 | Stone |
| 2006/0292099 A1 | 12/2006 | Milburn et al. |
| 2006/0293720 A1 | 12/2006 | DiLorenzo |
| 2006/0293721 A1 | 12/2006 | Tarver et al. |
| 2006/0293723 A1 | 12/2006 | Whitehurst et al. |
| 2007/0016262 A1 | 1/2007 | Gross et al. |
| 2007/0016263 A1 | 1/2007 | Armstrong et al. |
| 2007/0021785 A1 | 1/2007 | Inman et al. |
| 2007/0021786 A1 | 1/2007 | Parnis et al. |
| 2007/0021814 A1 | 1/2007 | Inman et al. |
| 2007/0025608 A1 | 2/2007 | Armstrong |
| 2007/0027482 A1 | 2/2007 | Parnis et al. |
| 2007/0027483 A1 | 2/2007 | Maschino et al. |
| 2007/0027484 A1 | 2/2007 | Guzman et al. |
| 2007/0027486 A1 | 2/2007 | Armstrong |
| 2007/0027492 A1 | 2/2007 | Maschino et al. |
| 2007/0027496 A1 | 2/2007 | Parnis et al. |
| 2007/0027497 A1 | 2/2007 | Parnis |
| 2007/0027498 A1 | 2/2007 | Maschino et al. |
| 2007/0027499 A1 | 2/2007 | Maschino et al. |
| 2007/0027500 A1 | 2/2007 | Maschino et al. |
| 2007/0027504 A1 | 2/2007 | Barrett et al. |
| 2007/0055324 A1 | 3/2007 | Thompson et al. |
| 2007/0067004 A1 | 3/2007 | Boveja et al. |
| 2007/0083242 A1 | 4/2007 | Mazgalev et al. |
| 2007/0093434 A1 | 4/2007 | Rossetti et al. |
| 2007/0093870 A1 | 4/2007 | Maschino |
| 2007/0093875 A1 | 4/2007 | Chavan et al. |
| 2007/0100263 A1 | 5/2007 | Merfeld |
| 2007/0100377 A1 | 5/2007 | Armstrong et al. |
| 2007/0100378 A1 | 5/2007 | Maschino |
| 2007/0100380 A1 | 5/2007 | Fukui |
| 2007/0100392 A1 | 5/2007 | Maschino et al. |
| 2007/0106339 A1 | 5/2007 | Errico et al. |
| 2007/0112404 A1 | 5/2007 | Mann et al. |
| 2007/0118177 A1 | 5/2007 | Libbus et al. |
| 2007/0118178 A1 | 5/2007 | Fukui |
| 2007/0129767 A1 | 6/2007 | Wahlstrand |
| 2007/0129780 A1 | 6/2007 | Whitehurst et al. |
| 2007/0135846 A1 | 6/2007 | Knudson et al. |
| 2007/0135856 A1 | 6/2007 | Knudson et al. |
| 2007/0135857 A1 | 6/2007 | Knudson et al. |
| 2007/0135858 A1 | 6/2007 | Knudson et al. |
| 2007/0142870 A1 | 6/2007 | Knudson et al. |
| 2007/0142871 A1 | 6/2007 | Libbus et al. |
| 2007/0142874 A1 | 6/2007 | John |
| 2007/0150006 A1 | 6/2007 | Libbus et al. |
| 2007/0150011 A1 | 6/2007 | Meyer et al. |
| 2007/0150021 A1 | 6/2007 | Chen et al. |
| 2007/0150027 A1 | 6/2007 | Rogers |
| 2007/0156180 A1 | 7/2007 | Jaax et al. |
| 2007/0198063 A1 | 8/2007 | Hunter et al. |
| 2007/0239243 A1 | 10/2007 | Moffitt et al. |
| 2007/0244522 A1 | 10/2007 | Overstreet |
| 2007/0250145 A1 | 10/2007 | Kraus et al. |
| 2007/0255320 A1 | 11/2007 | Inman et al. |
| 2007/0255333 A1 | 11/2007 | Giftakis |
| 2007/0255339 A1 | 11/2007 | Torgerson |
| 2008/0021517 A1 | 1/2008 | Dietrich |
| 2008/0021520 A1 | 1/2008 | Dietrich |
| 2008/0046055 A1 | 2/2008 | Durand et al. |
| 2008/0051852 A1 | 2/2008 | Dietrich et al. |
| 2008/0058871 A1 | 3/2008 | Libbus et al. |
| 2008/0103407 A1 | 5/2008 | Bolea et al. |
| 2008/0140138 A1 | 6/2008 | Ivanova et al. |
| 2008/0183226 A1 | 7/2008 | Buras et al. |
| 2008/0183246 A1 | 7/2008 | Patel et al. |
| 2008/0195171 A1 | 8/2008 | Sharma |
| 2008/0208266 A1 | 8/2008 | Lesser et al. |
| 2008/0213331 A1 | 9/2008 | Gelfand et al. |
| 2008/0234790 A1 | 9/2008 | Bayer et al. |
| 2008/0281365 A1 | 11/2008 | Tweden et al. |
| 2008/0281372 A1 | 11/2008 | Libbus et al. |
| 2009/0012590 A1 | 1/2009 | Inman et al. |
| 2009/0048194 A1 | 2/2009 | Aerssens et al. |
| 2009/0082832 A1 | 3/2009 | Carbunaru et al. |
| 2009/0088821 A1 | 4/2009 | Abrahamson |
| 2009/0105782 A1 | 4/2009 | Mickle et al. |
| 2009/0112291 A1 | 4/2009 | Wahlstrand et al. |
| 2009/0123521 A1 | 5/2009 | Weber et al. |
| 2009/0125079 A1 | 5/2009 | Armstrong et al. |
| 2009/0143831 A1 | 6/2009 | Huston et al. |
| 2009/0171405 A1 | 7/2009 | Craig |
| 2009/0177112 A1 | 7/2009 | Gharib et al. |
| 2009/0187231 A1 | 7/2009 | Errico et al. |
| 2009/0210042 A1 | 8/2009 | Kowalczewski |
| 2009/0248097 A1 | 10/2009 | Tracey et al. |
| 2009/0254143 A1 | 10/2009 | Tweden et al. |
| 2009/0275997 A1 | 11/2009 | Faltys et al. |
| 2009/0276019 A1 | 11/2009 | Perez et al. |
| 2009/0281593 A9 | 11/2009 | Errico et al. |
| 2009/0312817 A1 | 12/2009 | Hogle et al. |
| 2010/0003656 A1 | 1/2010 | Kilgard et al. |
| 2010/0010556 A1 | 1/2010 | Zhao et al. |
| 2010/0010571 A1 | 1/2010 | Skelton et al. |
| 2010/0010581 A1 | 1/2010 | Goetz et al. |
| 2010/0010603 A1 | 1/2010 | Ben-David et al. |
| 2010/0016746 A1 | 1/2010 | Hampton et al. |
| 2010/0042186 A1 | 2/2010 | Ben-David et al. |
| 2010/0063563 A1 | 3/2010 | Craig |
| 2010/0074934 A1 | 3/2010 | Hunter |
| 2010/0191304 A1 | 7/2010 | Scott |
| 2010/0215632 A1 | 8/2010 | Boss et al. |
| 2010/0241183 A1 | 9/2010 | DiLorenzo |
| 2010/0241207 A1 | 9/2010 | Bluger |
| 2010/0249859 A1 | 9/2010 | DiLorenzo |
| 2010/0280562 A1 | 11/2010 | Pi et al. |
| 2010/0280569 A1 | 11/2010 | Bobillier et al. |
| 2011/0004266 A1 | 1/2011 | Sharma |
| 2011/0054569 A1 | 3/2011 | Zitnik et al. |
| 2011/0066208 A1 | 3/2011 | Pasricha et al. |
| 2011/0082515 A1 | 4/2011 | Libbus et al. |
| 2011/0092882 A1 | 4/2011 | Firlik et al. |
| 2011/0144717 A1 | 6/2011 | Burton et al. |
| 2011/0224749 A1 | 9/2011 | Ben-David et al. |
| 2011/0247620 A1 | 10/2011 | Armstrong et al. |
| 2011/0275927 A1 | 11/2011 | Wagner et al. |
| 2011/0307027 A1 | 12/2011 | Sharma et al. |
| 2012/0053657 A1 | 3/2012 | Parker et al. |
| 2012/0065706 A1 | 3/2012 | Vallapureddy et al. |
| 2012/0179219 A1* | 7/2012 | Kisker ................ A61N 1/3787 607/7 |

(56) References Cited

U.S. PATENT DOCUMENTS

| | | | |
|---|---|---|---|
| 2012/0185009 A1 | 7/2012 | Kornet et al. | |
| 2012/0185020 A1 | 7/2012 | Simon et al. | |
| 2013/0013016 A1 | 1/2013 | Diebold | |
| 2013/0066392 A1 | 3/2013 | Simon et al. | |
| 2013/0066395 A1 | 3/2013 | Simon et al. | |
| 2013/0245718 A1 | 9/2013 | Birkholz et al. | |
| 2013/0317580 A1 | 11/2013 | Simon et al. | |
| 2014/0046407 A1 | 2/2014 | Ben-Ezra et al. | |
| 2014/0206945 A1 | 7/2014 | Liao | |
| 2014/0257425 A1 | 9/2014 | Arcot-Krishnamurthy et al. | |
| 2014/0277260 A1* | 9/2014 | Khalil | A61N 1/36071 607/46 |
| 2014/0288551 A1 | 9/2014 | Bharmi et al. | |
| 2014/0330335 A1 | 11/2014 | Errico et al. | |
| 2015/0018728 A1 | 1/2015 | Gross et al. | |
| 2015/0119956 A1 | 4/2015 | Libbus et al. | |
| 2015/0133717 A1* | 5/2015 | Ghiron | A61N 2/02 600/14 |
| 2015/0180271 A1* | 6/2015 | Angara | H02J 50/12 607/46 |
| 2015/0233904 A1 | 8/2015 | Nayak | |
| 2015/0241447 A1 | 8/2015 | Zitnik et al. | |
| 2016/0067497 A1 | 3/2016 | Levine et al. | |
| 2016/0114165 A1 | 4/2016 | Levine et al. | |
| 2016/0250097 A9 | 9/2016 | Tracey et al. | |
| 2016/0331952 A1 | 11/2016 | Faltys et al. | |
| 2016/0367808 A9 | 12/2016 | Simon et al. | |
| 2017/0197076 A1 | 7/2017 | Faltys et al. | |
| 2017/0202467 A1 | 7/2017 | Zitnik et al. | |
| 2017/0203103 A1 | 7/2017 | Levine et al. | |
| 2018/0001096 A1 | 1/2018 | Faltys et al. | |
| 2018/0021217 A1 | 1/2018 | Tracey et al. | |
| 2018/0021580 A1 | 1/2018 | Tracey et al. | |
| 2018/0085578 A1 | 3/2018 | Rennaker, II et al. | |
| 2018/0117320 A1 | 5/2018 | Levine et al. | |
| 2018/0289970 A1 | 10/2018 | Faltys et al. | |
| 2019/0010535 A1 | 1/2019 | Pujol Onofre et al. | |
| 2019/0022389 A1 | 1/2019 | Leonhardt | |
| 2019/0046799 A1 | 2/2019 | Levine et al. | |
| 2019/0111263 A1 | 4/2019 | Levine et al. | |
| 2019/0192847 A1 | 6/2019 | Faltys et al. | |
| 2019/0275328 A1 | 9/2019 | Zitnik et al. | |
| 2019/0366078 A1 | 12/2019 | Faltys et al. | |
| 2021/0315505 A1 | 10/2021 | Levine et al. | |
| 2021/0353949 A1 | 11/2021 | Faltys et al. | |

FOREIGN PATENT DOCUMENTS

| | | |
|---|---|---|
| CN | 101578067 A | 11/2009 |
| CN | 101868280 A | 10/2010 |
| CN | 104220129 A | 12/2014 |
| DE | 2628045 A1 | 1/1977 |
| DE | 3736664 A1 | 5/1989 |
| DE | 20316509 U1 | 4/2004 |
| EP | 0438510 B1 | 8/1996 |
| EP | 0726791 B1 | 6/2000 |
| EP | 1001827 B1 | 1/2004 |
| EP | 2213330 A2 | 8/2010 |
| EP | 2073896 B1 | 10/2011 |
| GB | 04133 A.D. 1909 | 2/1910 |
| GB | 2073428 * | 10/1981 |
| KR | 20050039445 A | 4/2005 |
| WO | WO93/01862 A1 | 2/1993 |
| WO | WO97/30998 A1 | 8/1997 |
| WO | WO98/20868 A1 | 5/1998 |
| WO | WO00/27381 A2 | 5/2000 |
| WO | WO00/47104 A2 | 8/2000 |
| WO | WO01/00273 A1 | 1/2001 |
| WO | WO01/08617 A1 | 2/2001 |
| WO | WO01/89526 A1 | 11/2001 |
| WO | WO02/44176 A1 | 6/2002 |
| WO | WO02/057275 A1 | 7/2002 |
| WO | WO03/072135 A2 | 9/2003 |
| WO | WO2004/000413 A2 | 12/2003 |
| WO | WO2004/064918 A1 | 8/2004 |
| WO | WO2006/073484 A1 | 7/2006 |
| WO | WO2006/076681 A2 | 7/2006 |
| WO | WO2007/133718 A2 | 11/2007 |
| WO | WO2010/005482 A1 | 1/2010 |
| WO | WO2010/067360 A2 | 6/2010 |
| WO | WO2010/118035 A2 | 10/2010 |
| WO | WO2016/134197 A1 | 8/2016 |

OTHER PUBLICATIONS

Abraham, Coagulation abnormalities in acute lung injury and sepsis, Am. J. Respir. Cell Mol. Biol., vol. 22(4), pp. 401-404, Apr. 2000.

Aekerlund et al., Anti-inflammatory effects of a new tumour necrosis factor-alpha (TNF-Alpha) inhibitor (CNI-1493) in collagen-induced arthritis (CIA) in rats, Clinical & Experimental Immunology, vol. 115, pp. 32-41, Jan. 1, 1999.

Anderson et al.; Reflex principles of immunoiogical homeostasis; Annu. Rev. Immunol.; 30; pp. 313-335; Apr. 2012.

Antonica, A., et al., Vagal control of lymphocyte release from rat thymus, J. Auton. Nerv. Syst., vol. 48(3), pp. 187-197, Aug. 1994.

Asakura et al., Non-surgical therapy for ulcerative colitis, Nippon Geka Gakkai Zasshi, vol. 98, No. 4, pp. 431-437, Apr. 1997 (abstract Only).

Beliavskaia et al.,"On the effects of prolonged stimulation of the peripherai segment of the vagus nerve . . . ," Fiziologicheszkii Zhurnal SSSR Imeni I.M. Sechenova., vol. 52(11); p. 1315-1321, Nov. 1966.

Ben-Noun et al.; Neck circumfereuce as a simple screening measure for identifying overweight and obese patients; Obesity Research; vol. 9; No. 8; pp. 470-477; Aug. 8, 2001.

Benoist, et al., "Mast cells in autoimmune disease" Nature., vol. 420(19): pp. 875-878, Dec. 2002.

Benthem et al.; Parasympathetic inhibition of sympathetic neural activity to the pancreas; Am.J.Physiol Endocrinol.Metab; 280(2); pp. E378-E381; Feb. 2001.

Bernik et al.; Vagus nerve stimulation attenuates cardiac TNF production in endotoxic shock, (supplemental to Shock, vol. 15, 2001, Injury, Inflammation and sepsis: laboratory and clinical approaches, Shock, Abstracts, 24th Annual Conference on Shock, Marco Island, FL, Jun. 9-12, 2001), Abstract No. 81.

Bernik et al., Vagus nerve stimulation attenuates endotoxic shock and cardiac TNF production, 87th Clinical Congress of the American College of Surgeons, New Orleans, LA, Oct. 9, 2001.

Bernik et al., Vagus nerve stimulation attenuates LPS-induced cardiac TNF production and myocardial depression IN shock, New York Surgical Society, New York, NY, Apr. 11, 2001.

Bernik, et al., Pharmacological stimulation of the cholinergic antiinflammatory pathway, The Journal of Experimental Medicine, vol. 195, No. 6, pp. 781-788, Mar. 18, 2002.

Besedovsky, H., et al., Immunoregulatory feedback between interleukin-1 and glucocorticoid hormones, Science, vol. 233, No. 4764, pp. 652-654, Aug. 1986.

Bhattacharya, S.K. et al., Central muscarinic receptor subtypes and carrageenin-induced paw oedema in rats, Res. Esp. Med. vol. 191(1), pp. 65-76, Dec. 1991.

Bianchi et al., Suppression of proinflammatory cytokines in monocytes by a tetravalent guanylhydrazone, Journal of Experimental Medicine, vol. 183, pp. 927-936, Mar. 1996.

Biggio et al.; Chronic vagus nerve stimulation induces neuronal plasticity in the rat hippocampus; Int. J. Neurpsychopharmacol.; vol. 12; No. 9; pp. 1209-1221; Oct. 2009.

Blackwell, T. S. et al., Sepsis and cytokines: current status, Br. J. Anaesth., vol. 77(1), pp. 110-117, Jul. 1996.

Blum, A. et al., Role of cytokines in heart failure, Am. Heart J., vol. 135(2), pp. 181-186, Feb. 1998.

Boldyreff, Gastric and intestinal mucus, its properties and physiological importance, Acta Medica Scandinavica (journal), vol. 89, Issue 1-2, pp. 1-14, Jan./Dec. 1936.

(56) References Cited

OTHER PUBLICATIONS

Borovikova et al., Acetylcholine inhibition of immune response to bacterial endotoxin in human macrophages, Abstracts, Society for Neuroscience, 29th Annual Meeting, Miami Beach, FL, (Abs. No. 624.6); Oct. 23-28, 1999.
Borovikova et al., Efferent vagus nerve activity attenuates cytokine-mediated inflammation, Society for Neuroscience Abstracts, vol. 26, No. 102, Nov. 4-9, 2000 (abstract only).
Borovikova et al., Intracerebroventricular CNI-1493 prevents LPS-induced hypotension and peak serum TNF at a four-log lower dose man systemic treatment, 21st Annual Conference on Shock, San Antonio, TX, Jun. 14-17, 1998, Abstract No. 86.
Borovikova et al., Role of the efforent vagus nerve signaling in the regulation of the innate immune response to LPS, (supplemental to Shock, vol. 13, 2000, Melecular, cellular, and systemic pathological aspects and therapeutic approaches, abstracts, 5th World Congress on Trauma, Shock inflammation and sepsis-pathophysiology, immune consequences and therapy, Feb. 29, 2000-Mar. 4, 2000, Munich, DE), Abstract No. 166.
Borovikova et al., Role of the vagus nerve in the anti-inflammatory effects of CNI-1493, the FASEB journal, vol. 14, No. 4, 2000 (Experimental Biology 2000, San Diego, CA, Apr. 15-18, 2000, Abstract No. 97.9).
Borovikova et al., Vagotomy blocks the protective effects of I.C.V. CNI-1493 against LPS-induced shock, (Supplemental to Shock, vol. 11, 1999, Molecular, cellular, and systemic pathobioloigal aspects and therapeutic approaches, abstacts and program, Fourth International Shock Congress and 22nd Annual Conference on Shock, Philadelphia, PA, Jun. 12-16, 1999), Abstract No. 277.
Borovikova, L. V., et al., Role of vagus nerve signaling in CNI-1493-mediated suppression of acute inflammation, Autonomic Neuroscience, vol. 85, No. 1-3, pp. 141-147, Dec. 20, 2000.
Borovikova, L. V., et al., Vagus nerve stimulation attenuates the systemic inflammatory response to endotoxin, Nature, vol. 405, No. 6785: pp. 458-462, May 25, 2000.
Bruchfeld et al.; Whole blood cytokine attenuation by cholinergic agonists ex vivo and relationship to vagus nerve activity in rheumatoid arthritis; J. Int. Med.; 268(1); pp. 94-101; Jul. 2010.
Bulloch et al.; Characterization of choline O-acetyltransferase (ChAT) in the BALB/C mouse spleen; Int.J.Neurosci.; 76(1-2); pp. 141-149; May 1994.
Bumgardner, G. L. et al., Transplantation and cytokines, Seminars in Liver (Disease, vol. 19, No. 2, Thieme Medical Publishers; pp. 189-204, © 1999.
Burke et al., Bent pseudoknots and novel RNA inhibitors of type 1 human immunodeficiency (virus (HIV-1) reverse transcriptase, J. Mol. Biol., vol. 264(4); pp. 650-666, Dec. 1996.
Bushby et al; Centiles for adult head circumference; Archives of Disease in Childhood; vol. 67(10); pp. 1286-1287; Oct. 1992.
Cano et al.; Characterization of the central nervous system innervation of the rat spleen using viral transneuronal tracing; J.Comp Neurol.; 439(1); pp. 1-18; Oct. 2001.
Carteron, N. L., Cytokines in rheumatoid arthritis: trials and tribulations, Mol. Med. Today, vol. 6(8), pp. 315-323, Aug. 2000.
Cavaillon et al.; The pro-inflammatory cytokine casade; Immune Response in the Critically Ill; Springer-Verlag Berlin Hiedelberg; pp. 37-66; Jan. 21, 2002.
Cheyuo et al.; The parasympathetic nervous system in the quest for stroke therapeutics; J. Cereb. Blood Flow Metab.; 31(5); pp. 1187-1195; May 2011.
Cicala et al., "Linkage between inflammation and coagulation: An update on the molecular basis of the crosstalk," Life Sciences, vol. 62(20); pp. 1817-1824, Apr. 1998.
Clark et al.; Enhanced recognition memory following vagus nerve stimulation in human subjects; Nat. Neurosci.; 2(1); pp. 94-98; Jan. 1999.
Cohen, "The immunopathogenesis of sepsis," Nature., vol. 420(6917): pp. 885-891, Dec. 2002.

Corcoran, et al., The effects of vagus nerve stimulation on pro- and anti-inflammatory cytokines in humans: a preliminary report, NeuroImmunoModulation, vol. 12(5), pp. 307-309, Sep. 2005.
Crusz et al.; Inflammation and cancer; advances and new agents; Nature reviews Clinical Oncology; 12(10); pp. 584-596; doi: 10.1038/nrclinonc.2015.105; Jun. 30, 2015.
Dake; Chronic cerebrospinal venous insufficiency and multiple sclerosis: Hostory and background; Techniques Vasc. Intervent. Radiol.; 15(2); pp. 94-100; Jun. 2012.
Das, Critical advances in spticemia and septic shock, Critical Care, vol. 4, pp. 290-296, Sep. 7, 2000.
Del Signore el al; Nicotinic acetylcholine receptor subtypes in the rat sympathetic ganglion: pharmacological characterization, subcellular distribution and effect of pre- and postganglionic nerve crush; J.Neuropathol.Exp.Neurol.; 63(2); pp. 138-150; Feb. 2004.
Diamond et al.; Mapping the immunological homunculus; Proc. Natl. Acad. Sci. USA; 108(9); pp. 3461-3462; Mar. 1, 2011.
Dibbs, Z., et al., Cytokines in heart failure: pathogenetic mechanisms and potential treatment, Proc. Assoc. Am. Physicians, vol. 111, No. 5, pp. 423-428, Sep.-Oct. 1999.
Dinarello, C. A., The interleukin-1 family: 10 years of discovery, FASEB J., vol. 8, No. 15, pp. 1314-1325, Dec. 1994.
Dorr et al.; Effect of vagus nerve stimulation on serotonergic and noradrenergic transmission; J. Pharmacol. Exp. Ther.; 318(2); pp. 890-898; Aug. 2006.
Doshi et al., Evolving role of tissue factor and its pathway inhibitor, Crit. Care Med., vol. 30, suppl. 5, pp. S241-S250, May 2002.
Elenkov et al.; Stress, corticotropin-releasing hormone, glucocorticoids, and the immune / inflammatory response: acute and chronic effects; Ann. N.Y. Acad. Sci.; 876; pp. 1-13; Jun. 22, 1999.
Ellington et al., In vitro selection of RNA molecules that bind specific ligands, Nature, vol. 346, pp. 818-822, Aug. 30, 1990.
Ellrich et al.; Transcutaneous vagus nerve stimulation; Eur. Neurological Rev.; 6(4); pp. 254-256; Winter 2011.
Engineer et al.; Directing neural plasticity to understand and treat tinnitus; Hear. Res.; 295; pp. 58-66; Jan. 2013.
Engineer et al.; Reversing pathological neural activity using targeted plasticity; Nature; 470(7332); pp. 101-104; Feb. 3, 2011 (Author Manuscript).
Esmon, The protein C pathway, Crit. Care Med., vol. 28, suppl. 9, pp. S44-S48, Sep. 2000.
Fields; New culprits in chronic pain; Scientific American; pp. 50-57; Nov. 2009.
Fleshner, M., et al., Thermogenic and corticosterone responses to intravenous cytokines (IL-1? and TNF-?) are attenuated by subdiaphragmatic vagotomy, J. Neuroimmunol., vol. 86(2), pp. 134-141, Jun. 1998.
Fox, D. A., Cytokine blockade as a new strategy to treat rheumatoid arthritis, Arch. Intern. Med., vol. 160, pp. 437-444, Feb. 28, 2000.
Fox, et al., Use of muscarinic agonists in the treatment of Sjorgren' syndrome, Clin. Immunol., vol. 101, No. 3; pp. 249-263, Dec. 2001.
Fujii et al.; Simvastatin regulates non-neuronal cholinergic activity in T lymphocytes via CD11a-mediated pathways; J. Neuroimmunol.; 179(1-2); pp. 101-107; Oct. 2006.
Gao et al.; Investigation of specificity of auricular acupuncture points in regulation of autonomic function in anesthetized rats; Autonomic Neurosc.; 138(1-2); pp. 50-56; Feb. 29, 2008.
Gattorno, M., et al., Tumor necrosis factor induced adhesion molecule serum concentrations in henoch-schoenlein purpura and pediatric systemic lupus erythematosus, J. Rheumatol., vol. 27, No. 9, pp. 2251-2255, Sep. 2000.
Gaykema, R. P., et al., Subdiaphragmatic vagotomy suppresses endotoxin-induced activation of hypothalamic corticotropin-releasing hormone neurons and ACTH secretion, Endocrinology, vol. 136, No. 10, pp. 4717-4720, Oct. 1995.
Ghelardini et al., S-(−)-ET 126: A potent and selective M1 antagonist in vitro and in vivo, Life Sciences, vol. 58, No. 12, pp. 991-1000, Feb. 1996.
Ghia, et al., The vagus nerve: a tonic inhibitory influence associated with inflammatory bowel disease in a murine model, Gastroenterology, vol. 131, No. 4, pp. 1122-1130, Oct. 2006.

(56) References Cited

OTHER PUBLICATIONS

Giebelen, et al., Stimulation of ?7 cholinergic receptors inhibits lipopolysaccharide-induced neutrophil recruitment by a tumor necrosis factor ?-indspendent mechanism, Shock, vol. 27, No. 4, pp. 443-447, Apr. 2007.
Goyal et al., Nature of the vagal inhibitory innervation to the lower esophageal sphincter. Journal of Clinical Investigation, vol. 55, pp. 1119-1126, May 1975.
Gracie, J. A., et al., A proinflammatory rale for IL-18 in rheumatoid arthritis, J. Clin. Invest., vol. 104, No. 10, pp. 1393-1401, Nov. 1999.
Granert et al., Suppression of macrophage activation with CNI-1493 increases survival in infant rats with systemic haemophilus influenzae infection, Infection and Immunity, vol. 68, No. 9, pp. 5329-5334, Sep. 2000.
Green et al., Feedback technique for deep relaxation, Psycophysiology, vol. 6, No. 3, pp. 371-377, Nov. 1969.
Gregory et al., Neutrophil-kupffer-cell interaction in host defenses to systemic infections, Immunology Today, vol. 19, No. 11, pp. 507-510, Nov. 1998.
Groves et al.; Recordings from the rat locus coeruleus during acute vagal nerve stimulation in the anaesthetised rat; Neuroscience Letters; 379(3); pp. 174-179; May 13, 2005.
Guarente, Leonard, Ph. D.; Sirtuins, Aging, and Medicine; N Engl J Med ; vol. 364:pp. 2235-2244; Jun. 2011.
Guslandi, M., Nicotine treatment for ulcerative colitis, Br. J. Clin. Pharmacol., vol. 48(4), pp. 481-484, Oct. 1999.
Hansson, E.; Could chronic pain and spread of pain sensation be induced and maintained by glial activation?. Acta Physiologica, vol. 187, Issue 1-2; pp. 321R327, May/Jun. 2006.
Harrison's Principles of Internal Medicine, 13th Ed., pp. 511-515 and 1433-1435, Mar. 1994.
Hatton et al.; Vagal nerve stimulation: overview and implications for anesthesiologists; Int'l Anesthesia Research Society; vol. 103; No. 5; pp. 1241-1249; Nov. 2006.
Hirano, T., Cytokine suppresive agent improves survival rate in rats with acute pancreatitis of closed duodenal loop, J. Surg. Res., vol. 81, No. 2, pp. 224-229, Feb. 1999.
Hirao et al., The limits of specificity: an experimental analysis with RNA aptamers to MS2 coat protein variants, Mol. Divers., vol. 4, No. 2, pp. 75-89, 1999 (Accepted Jan. 13, 1999).
Hoffer et al.; Implantable electrical and mechanical interfaces with nerve and muscle; Annals of Biomedical Engineering; vol. 8; pp. 351-360; Jul. 1980.
Holladay et al., Neuronal nicotinic acetylcholine receptors as targets for drug discovery, Journal of Medicinal Chemistry, 40(26), pp. 4169-4194, Dec. 1997.
Hommes, D. W. et al., Anti- and Pro-inflammatory cytokines in the pathogeresis of tissue damage in Crohn's disease, Current Opinion in Clinical Nutrition and Metabolic Care, vol. 3(3), pp. 191-195, May 2000.
Hsu, et al., Analysis of efficiency of magnetic stimulation, IEEE Trans. Biomed. Eng., vol. 50(11), pp. 1276-1285, Nov. 2003.
Hsu, H. Y., et al., Cytokine release of peripheral blood monocuclear cells in children with chronic hepatitis B virus infection, J. Pediatr. Gastroenterol., vol. 29, No. 5, pp. 540-545, Nov. 1999.
Hu, et ai., The effect of norepinephrine on endotoxin-mediated macrophage activation, J. Neuroimmunol., vol. 31(1), pp. 35-42, Jan. 1991.
Huston et al.; Splenectomy inactivates the cholinergic antiinflammatory pathway during lethal endotoxemia and polymicrobial sepsis; J. Exp. Med. 2006; vol. 203, No. 7, pp. 1623-1628; Jun. 19, 2006.
Huston et al.; Transcutaneous vagus nerve stimulation reduces serum high mobility group box 1 levels and improves survival in murine sepsis; Crit. Care Med.; 35(12); pp. 2762-2768; Dec. 2007.
Hutchinson et al.; Proinflammatory cytokines oppose opioid induced acute and chronic analgesia; Brain Behav Immun.; vol. 22; No. 8; pp. 1178-1189; Nov. 2008.

Ilton et al., "Differential expression of neutrophil adhesion molecules during coronary artery surgery with cardiopulmonary bypass" Journal of Thoracic and Cardiovascular Surgery, Mosby-Year Book, Inc., St. Louis, Mo, US, pp. 930-937, Nov. 1, 1999.
Jaeger et al., The structure of HIV-1 reverse transcriptase complexed with an RNA pseudoknot inhibitor, The EMBO Journal, 17(15), pp. 4535-4542, Aug. 1998.
Jander, S. et al., Interleukin-18 is induced in acute inflammatory demyelinating polymeuropathy, J. Neuroimmunol., vol. 114, pp. 253-258, Mar. 2001.
Joshi et al., Potent inhibition of human immunodeficiency virus type 1 replection by template analog reverse transcriptase , J. Virol., 76(13), pp. 6545-6557, Jul. 2002.
Kawahara et al.; SIRT6 links histone H3 lysine 9 deacetylation to NF-kappaB-dependent gene expression and organismal life span.; Cell. ; vol. 136; No. 1; pp. 62-74; Jan. 2009.
Kalishevskaya et al. "The character of vagotomy-and atropin-induced hypercoagulation," Sechenov Physiological Journal of the USSR, 65(3): pp. 398-404, Mar. 1979.
Kalishevskaya et al.; Nervous regulation of the fluid state of the blood; Usp. Fiziol. Nauk;,vol. 13; No. 2; pp. 93-122; Apr.-Jun. 1982.
Kanai, T. et al., Interleukin-18 and Crohn's disease, Digestion, vol. 63, suppl. 1, pp. 37-42, (year of pub. sufficiently earlier than effective US filing date and any foreign priority date) 2001.
Katagiri, M., et al., Increased cytokine production by gastric mucosa in patients with helicobacter pylori infection, J. Clin, Gastroenterol., vol. 25, Suppl. 1, pp. S211-S214, 1997.
Kawashima, et al., Extraneuronal cholinergic system in lymphocytes, Pharmacology & Therapeutics, vol. 86, pp. 29-48, Apr. 2000.
Kees et al; Via beta-adrenoceptors, stimulalion of extraspleniic sympathetic nerve fibers inhibits lipopolysaccharide-induced TNF secretion in perfused rat spleen; J.Neuroimmunol.; 145(1-2); pp. 77-85; Dec. 2003.
Kensch et al., HIV-1 reverse transcriptase-pseudoknot RNA aptamer interaction has a binding affinity in the low picomolar range coupled with high specificity, J. Biol. Chem., 275(24), pp. 18271-18278, Jun. 16, 2000.
Khatun, S., et al., "Induction of hypercoagulability condition by chronic localized cold stress in rabbits," Thromb. and Haemost., 81(3): pp. 449-455, Mar. 1999.
Kimball, et al., Levamisole causes differential cytokine expression by elicited mouse peritoneal macrophases, Journal of Leukocyte Biology, vo. 52, No. 3, pp. 349-356, Sep. 1992 (abstract only).
Kimmings, A. N., et al., Systemic inflammatory response in acute cholangitis and after subsequent treatment, Eur. J. Surg., vol. 166, pp. 700-705, Sep. 2000.
Kirchner et al.; Left vagus nerve stimulation suppresses experimentally induced pain; Neurology; vol. 55; pp. 1167-1171; Oct. 2000.
Kokkula, R. et al., Successful treatment of collagen-induced arthritis in mice and rats by targeting extracellular high mobility group box chromosomal protein 1 activity, Arthritis Rheum., 48(7), pp. 2052-2058, Jul. 2003.
Koopman et al.; Pilot study of stimulation of the cholinergic anti-inflammatory pathway with an implantable vagus nerve stimulation device in patients with rheumatoid arthritis; Arth. Rheum.; 64(10 suppl.); pp. S195; Oct. 2012.
Krarup et al; Conduction studies in peripheral cat nerve using implanted electrodes: I. methods and findings in controls; Muscle & Nerve; vol. 11; pp. 922-932; Sep. 1988.
Kudrjashov, et al. "Reflex nature of the physiological anticoagulating system," Nature, vol. 196(4855): pp. 647-649; Nov. 17, 1962.
Kumins, N. H., et al., Partial hepatectomy reduces the endotoxin-induced peak circulating level of tumor necrosis factor in rats, Shock, vol. 5, No. 5, pp. 385-388, May 1996.
Kuznik, "Role of the vascular wall in the process of hemostatis," Usp Sovrem Biol., vol. 75(1): pp. 61-85, (year of pub. sufficiently earlier than effective US filing date and any foreign priority date)1973.
Kuznik, et al., "Blood Coagulation in stimulation of the vagus nerve in cats," Biull. Eskp. Biol. Med., vol. 78(7): pp. 7-9, (year of pub. sufficiently earlier than effective US filing date and any foreign priority date) 1974.

(56) References Cited

OTHER PUBLICATIONS

Kuznik, et al., "Heart as an efferent regulator of the process of blood coagulation and fibrinolysis," Kardlologiia, vol. 13(3): pp. 10-17, (year of pub. sufficiently earlier than effective US filing date and any foreign priority date) 1973.
Kuznik, et al., "Role of the heart and vessels in regulating blood coagulation and fibrinolysis," Kagdiologiia, vol. 13(4): pp. 145-154, Apr. 1973.
Kuznik, et al., "Secretion of blood coagulation factors into saliva under conditions of hypo-and hypercoagulation," Voprosy Meditsinskoi Khimii, vol. 19(1): pp. 54-57; (year of pub. sufficiently earlier than effective US filing date and any foreign priority date) 1973.
Kuznik, et al., "The dynamics of procoagulatible and fibrinolytic activities during electrical stimulation of peripheral nerves," Sechenov Physiological Journal of the USSR, vol. 65; No. 3: pp. 414-420, Mar. 1979.
Kuznik, et al., "The role of the vascular wall in the mechanism of control of blood coagulation and fibrinolysis on stimulation of the vagus nerve," Cor Vasa, vol. 17(2): pp. 151-158, (year of pub. sufficiently earlier than effective US filing date and any foreign priority date) 1975.
Lang, et al., "Neurogienic control of cerebral blood flow," Experimental Neurology, 43(1): pp. 143-161, Apr. 1974.
Lee, H. G., et al., Peritoneal lavage fluids stimulate NIH3T3 fibroblast proliferation and contain increased tumour necrosis factor and IL6 in experimental silica-induced rat peritonitis, Clin. Exp. Immunol., vol. 100, pp. 139-144, Apr. 1995.
LeNovere, N. et al., Molecular evolution of the nicotinic acetylcholine receptor; an example of multigene family in excitable cells, J. Mol. Evol., 40, pp. 155-172, Feb. 1995.
Leonard, S. et al., Neuronal nicotinic receptors: from structure to function, Nicotine & Tobacco Res. 3:203-223, Aug. 2001.
Lips et al.; Coexpression and spatial association of nicotinic acetylcholine receptor subunits alpha7 and alpha10 in rat sympathetic neurons; J.Mol.Neurosci.; 30; pp. 15-16; Feb. 2006.
Lipton, J. M. et al.; Anti-inflammatory actions of the neuroimmunomodulator ?-MSH, Immunol. Today, vol. 18, pp. 140-145, Mar. 1997.
Loeb et al.; Cuff electrodes for chronic stimulation and recording of peripheral nerve activity; Journal of Neuroscience Methods; vol. 64; pp. 95-103; Jan. 1996.
Madretsma, G. S., et al., Nicotine inhibits the in vitro production of interleukin 2 and tumour necrosis factor-alpha by human monocuclear cells, Immunopharmacology, vol. 35, No. 1, pp. 47-51, Oct. 1996.
Manta et al.; Optimization of vagus nerve stimulaticn parameters using the firing activity of serotonin neurons in the rat dorsal raphe; European Neuropsychopharmacology; vol. 19; pp. 250-255; Jan. 2009 (doi: 10.1016/j.euroneuro.2008.12.001).
Martindale: The Extra Pharmacopoeia; 28th Ed. London; The Pharmaceutical Press; pp. 446-485; © 1982.
Martiney et al., Prevention and treatment of experimental autoimmune encephalomyelitis by CNI-1493, a macrophage-deactivating agent, Journal of Immunology, vol. 160, No. 11, pp. 5588-5595, Jun. 1, 1998.
McGuinness, P. H., et al., Increases in intrahepatic CD68 positive cells, MAC387 positive cells, and proinflammatory cytokines (particulary interleukin 18) in chronic hepatitis C infection, Gut, vol. 46(2), pp. 260-269, Feb. 2000.
Miguel-Hidalgo, J.J.; The role of glial cells in drug abuse; Current Drug Abuse Reviews; vol. 2; No. 1; pp. 76-82; Jan. 2009.
Milligan et al.; Pathological and protective roles of glia in chronic pain; Nat Rev Neurosci.; vol. 10; No. 1; pp. 23-26; Jan. 2009.
Minnich et al.; Anti-cytokine and anti-inflammatory therapies for the treatment of severe sepsis: progress and pitfalls; Proceedings of the Nutrition Society; vol. 63(3); pp. 437-441; Aug. 2004.
Mishchenko, et al., "Coagulation of the blood and fibrinolysos in dogs during vagal stimulation," Sechenov Physiological Journal of the USSR, vol. 61(1): pp. 101-107, 1975.

Mishchenko, "The role of specific adreno-and choline-receptors of the vascular wall in the regulation of blood coagulation in the stimulation of the vagus nerve," Biull. Eskp. Bioi. Med., vol. 78(8): pp. 19-22, 1974.
Molina et al., CNI-1493 attenuates hemodynamic and pro-inflammatory responses to LPS, Shock, vol. 10, No. 5, pp. 329-334, Nov. 1998.
Nadol et al., "Surgery of the Ear and Temporal Bone," Lippinkott Williams & Wilkins, 2nd Ed., 2005, (Publication date: Sep. 21, 2004), p. 580.
Nagashima et al., Thrombin-activatable fibnnolysis inhibitor (TAFI) deficiency is compatible with murine life, J. Clin. Invest., 109, pp. 101-110, Jan. 2002.
Nathan, C. F., Secretory products of macrophages, J. Clin. Invest., vol. 79(2), pp. 319-326, Feb. 1987.
Navalkar et al.; Irbesartan, an angiotensin type 1 receptor inhibitor, regulates markers of infammation in patients with premature atherosclerosis; Journal of the American College of Cardiology; vol. 37; No. 2; pp. 440-444; Feb. 2001.
Navzer et al.; Reversing pathological neural activity using targeted plasticity; Nature; 470(7332); pp. 101-104; Feb. 3, 2011.
Neuhaus et al.; P300 is enhanced in responders to vagus nerve stimulation for treatment of major depressive disorder; J. Affect. Disord.; 100(1-3); pp. 123-128; Jun. 2007.
Noguchi et al., Increases in Gastric acidity in response to electroacupuncture stimulation of hindlimb of anesthetized rats, Jpn. J. Physiol., 46(1), pp. 53-58, Feb. 1996.
Norton, Can ultrasound be used to stimulate nerve tissue, BioMedical Engineering OnLine, 2(1), pp. 6, Mar. 4, 2003.
Olofsson et al.; Rethinking inflammation: neural circuits in the regulation of immunity; Immunological Reviews; 248(1); pp. 188-204; Jul. 2012.
Oshinsky et al.; Non-invasive vagus nerve stimulation as treatment for trigeminal allodynia; Pain; 155(5); pp. 1037-1042; May 2014.
Palmblad et al., Dynamics of early synovial cytokine expression in rodent collagen-induced arthritis: a thereapeutic study unding a macrophage-deactivation compound, American Journal of Pathology, vol. 158, No. 2, pp. 491-500, Feb. 2, 2001.
Pateyuk, et al.,"Treatment of Botkin's disease with heparin," Klin. Med., vol. 51(3): pp. 113-117, Mar. 1973.
Pavlov et al; Controlling inflammation: the cholinergic anti-inflammatory pathway; Biochem. Soc. Trans.; 34(Pt 6); pp. 1037-1040; Dec. 2006.
Payne, J. B. et al., Nicotine effects on PGE2 and IL-1 beta release by LPS-treated human monocytes, J. Perio. Res., vol. 31, No. 2, pp. 99-104, Feb. 1996.
Peuker; The nerve supply of the human auricle; Clin. Anat.; 15(1); pp. 35-37; Jan. 2002.
Pongratz et al.; The sympathetic nervous response in inflammation; Arthritis Research and Therapy; 16(504); 12 pages; retrieved from the internet (http://arthritis-research.com/content/16/6/504) ; Jan. 2014.
Prystowsky, J. B. et al., Interleukin-1 mediates guinea pig gallbladder inflammation in vivo, J. Surg. Res., vol. 71, No. 2, pp. 123-126, Aug. 1997.
Pulkki, K. J., Cytokines and cardiomyocyte death, Ann. Med., vol. 29(4), pp. 339-343, Aug. 1997.
Pullan, R. D., et al., Transdermal nicotine for active ulceratiive colitis, N. Engl. J. Med., vol. 330, No. 12, pp. 811-815, Mar. 24, 1994.
Pulvirenti et al; Drug dependence as a disorder of neural plasticity:focus on dopamine and glutamate; Rev Neurosci.; vol. 12; No. 2; pp. 141-158; Apr./Jun. 2001.
Rahman et al.; Mammalian Sirt 1: Insights on its biological functions; Cell Communications and Signaling; vol. 9; No. 11; pp. 1-8; May 2011.
Rayner, S. A. et al., Local bioactive tumour necrosis factor (TNF) in corneal allotransplantation, Clin. Exp. Immunol., vol. 122, pp. 109-116, Oct. 2000.
Reale et al.; Treatment with an acetylcholinesterase inhibitor in alzheimer patients modulates the expression and production of the pro-inflammatory and anti-inflammatory cytokines; J. Neuroimmunology; 148(1-2); pp. 162-171; Mar. 2004.

(56) References Cited

OTHER PUBLICATIONS

Rinner et al.; Rat lymphocytes produce and secrete acetylcholine in dependence of differentiation and activation; J.Neuroimmunol.; 81(1-2); pp. 31-37; Jan. 1998.
Robinson et al.; Studies with the Electrocardiograph on the Action of the Vagus Nerve on the Human Heart; J Exp Med; 14(3):217-234; Sep. 1911.
Romanovsky, A. A., et al.,The vagus nerve in the thermoregulatory response to systemic inflammation, Am. J. Physiol., vol. 273, No. 1 (part 2), pp. R407-R413, Jul. 1, 1997.
Saghizadeh et al.; The expression of TNF? by human muscle; J. Clin. Invest.; vol. 97; No. 4; pp. 1111-1116; Feb. 15, 1996.
Saindon et al.; Effect of cervical vagotomy on sympathetic nerve responses to peripheral interleukin-1beta; Auton.Neuroscience Basic and Clinical; 87; pp. 243-248; Mar. 23, 2001.
Saito, Involvement of muscarinic M1 receptor in the central pathway of the serotonin-induced bezold-jarisch reflex in rats, J. Autonomic Nervous System, vol. 49, pp. 61-68, Sep. 1994.
Sandborn, W. J., et al., Transdermal nicotine for mildly to moderately active ulcerative colitis, Ann. Intern. Med, vol. 126, No. 5, pp. 364-371, Mar. 1, 1997.
Sato, E., et al., Acetylcholine stimulates alveolar macrophages to release inflammatory cell chemotactic activity, Am. J. Physiol., vol. 274, pp. L970-L979, Jun. 1998.
Sato, K.Z., et al., Diversity of mRNA expression for muscarinic acetylcholine receptor subtypes and neuronal nicotinic acetylcholine receptor subunits in human mononuclear leukosytes and leukemic cell lines, Neuroscience Letters, vol. 266, pp. 17-20, Apr. 30, 1996.
Scheinman, R. I., et al., Role of transcriptional activation of I?B? in mediation of immunosuppression by glucocorticoids, Science, vol. 270, No. 5234, pp. 283-286, Oct. 13, 1995.
Schneider et al., High-affinity ssDNA inhibitors of the review transcriptase of type 1 human immunodeficiency virus, Biochemistry, 34(29), pp. 9599-9610, Jul. 1995.
Shafer, Genotypic testing for human immunodeficiency virus type 1 drug resistance, Clinical Microbiology Reviews, vol. 15, pp. 247-277, Apr. 2002.
Shapiro et al.; Prospective, randomised trial of two doses of rFVIIa (NovoSeven) in haemophilia patients with inhibitors undergoing surgery; Thromb Haemost; vol. 80(5); pp. 773-778; Nov. 1998.
Sher, M. E., et al., The influence of cigarette smoking on cytokine levels in patients with inflammatory bowel disease, Inflamm. Bowel Dis., vol. 5, No. 2, pp. 73-78, May 1999.
Shi et al.; Effects of efferent vagus nerve excitation on inflammatory response in heart tissue in rats with endotoxemia; vol. 15, No. 1; pp. 26-28; Jan. 2003 (Eng. Abstract).
Snyder et al., Correction of hemophilia B in canine and murine models using recombinant adeno-associated viral vectors; Nature Medicine, 5(1), pp. 64-70, Jan. 1999.
Sokratov, et al. "The role of choline and adrenegic structures in regulation of renal excretion of hemocoagulating compounds into the urine," Sechenov Physiological Journal of the USSR, vol. 63(12): pp. 1728-1732, 1977.
Stalcup et al., Endothelial cell functions in the hemodynamic responses to stress, Annals of the New York Academy of Sciences, vol. 401, pp. 117-131, Dec. 1982.
Steinlein, New functions for nicotine acetylcholine receptors?, Behavioural Brain Res., vol. 95(1), pp. 31-35, Sep. 1998.
Sternberg, E. M., Perspectives series: cytokines and the brain 'neural-immune interactions in health and disease,' J. Clin. Invest., vol. 100, No. 22, pp. 2641-2647, Dec. 1997.
Stevens et al.; The anti-inflammatory effect of some immunosuppressive agents; J. Path.; 97(2); pp. 367-373; Feb. 1969.
Strojnik et al.; Treatment of drop foot using and implantable peroneal underknee stimulator; Scand. J. Rehab. Med.; vol. 19(1); pp. 37R43; Dec. 1986.
Strowig et al.; Inflammasomes in health and disease; Nature; vol. 481; pp. 278-286; doi: 10.1038/nature10759; Jan. 19, 2012.

Sugano et al., Nicotine Inhibits the production of inflammatory mediators in U937 cells through modulation of nuclear factor-kappaβ activation, Biochemical and Biophysical Research Communications, vol. 252, No. 1, pp. 25-28, Nov. 9, 1998.
Suter et al.; Do glial cells control pain?; Neuron Glia Biol.; vol. 3; No. 3; pp. 255-268; Aug. 2007.
Swick et al.; Locus coeruleus neuronal activity in awake monkeys: relationship to auditory P300-like potentials and spontaneous EEG. Exp. Brain Res.; 101(1); pp. 86-92; Sep. 1994.
Sykes, et al., An investigation into the effect and mechanisms of action of nicotine in inflammatory bowel disease, Inflamm. Res., vol. 49, pp. 311-319, Jul. 2000.
Takeuchi et al., A comparision between chinese blended medicine "Shoseiryuto" tranilast and ketotifen on the anit-allergic action in the guinea pigs, Allergy, vol. 34, No. 6, pp. 387-393, Jun. 1985 (eng. abstract).
Tekdemir et al.; A clinico-anatomic study of the auricular branch of the vagus nerve and arnold's ear-cough reflex; Surg. Radiol. Anat.; 20(4); pp. 253-257; Mar. 1998.
Toyabe, et al., Identification of nicotinic acetylcholine receptors on lymphocytes in the periphery as well as thymus in mice, Immunology, vol. 92(2), pp. 201-205, Oct. 1997.
Tracey et al., Mind over immunity, Faseb Journal, vol. 15, No. 9, pp. 1575-1576, Jul. 2001.
Tracey, K. J. et al., Anti-cachectin/TNF monoclonal antibodies prevent septic shock during lethal bacteraemia; Nature, 330: pp. 662-664, Dec. 23, 1987.
Tracey, K. J. et al., Physiology and immunology of the cholinergic antiinflammatory pathway; J Clin Invest.; vol. 117: No. 2; pp. 289-296; Feb. 2007.
Tracey, K. J.; Reflex control of immunity; Nat Rev Immunol; 9(6); pp. 418-428; Jun. 2009.
Tracey, K. J. et al., Shock and tissue injury induced by recombinant human cachectin, Science, vol. 234, pp. 470-474, Oct. 24, 1986.
Tracey, K.J., The inflammatory reflex, Nature, vol. 420, pp. 853-859, Dec. 19-26, 2002.
Tsutsui, H., et al., Pathophysiolocical roles of interleukin-18 in inflammatory liver diseases; Immunol. Rev., 174:192-209, Apr. 2000.
Tuerk et al., RNA pseudoknots that inhibit human immunodeficiency virus type 1 reverse transcriptase; Proc. Natl. Acad. Sci. USA, 89, pp. 6988-6992, Aug. 1992.
Tuerk et al., Systematic evolution of ligands by exponential enrichment: RNA ligands to bacteriophage T4 DNA polymerase; Science, 249(4968), pp. 505-510, Aug. 3, 1990.
Van Dijk, A. P., et al., Transdermal nictotine inhibits interleukin 2 synthesis by mononuclear cells derived from healthy volunteers, Eur. J. Clin. Invest, vol. 28, pp. 664-671, Aug. 1998.
Van Der Horst et al.; Stressing the role of FoxO proteins in lifespan and disease; Nat Rev Mol Cell Biol.; vol. 8; No. 6; pp. 440-450; Jun. 2007.
Vanhoutte, et al., Muscarinic and beta-adrenergic prejunctional modulation of adrenergic neurotransmission in the blood vessel wall, Gen Pharmac., vol. 14(1), pp. 35-37, Jan. 1983.
VanWesterloo, et al., The cholinergic anti-inflammatory pathway regulates the host response during septic peritonitis, The Journal of Infectious Diseases, vol. 191, pp. 2138-2148, Jun. 15, 2005.
Ventureyra, Transcutaneous vagus nerve stimulation for partial onset seizure therapy, Child's Nerv Syst, vol. 16(2), pp. 101-102, Feb. 2000.
Vijayaraghavan, S.; Glial-neuronal interactions-implications for plasticity anddrug addictionl AAPS J.; vol. 11; No. 1; pp. 123-132; Mar. 2009.
Villa et al., Protection against lethal polymicrobial sepsis by CNI-1493, an inhibitor of pro-inflammatory cytokine synthesis, Journal of Endotoxin Research, vol. 4, No. 3, pp. 197-204, Jun. 1997.
Von Känel, et al., Effects of non-specific ?-adrenergic stimulation and blockade on blood coagulation in hypertension, J. Appl. Physiol., vol. 94, pp. 1455-1459, Apr. 2003.
Von Känel, et al., Effects of sympathetic activation by adrenergic infusions on hemostasis in vivo, Eur. J. Haematol., vol. 65: pp. 357-369, Dec. 2000.

(56) References Cited

OTHER PUBLICATIONS

Walland et al., Compensation of muscarinic brochial effects of talsaclidine by concomitant sympathetic activation in guinea pigs; European Journal of Pharmacology, vol. 330(2-3), pp. 213-219, Jul. 9, 1997.
Wang et al; Nicotinic acetylcholine receptor alpha7 subunit is an essential regulator of inflammation; Nature; 421; 384-388; Jan. 23, 2003.
Wang, H., et al., HMG-1 as a late mediator of endotoxin lethality in mice, Science, vol. 285, pp. 248-251, Jul. 9, 1999.
Waserman, S. et al., TNF-? dysregulation in asthma: relationship to ongoing corticosteroid therapy, Can. Respir. J., vol. 7, No. 3, pp. 229-237, May-Jun. 2000.
Watanabe, H. et al., The significance of tumor necrosis factor (TNF) levels for rejection of joint allograft, J. Reconstr. Microsurg., vol. 13, No. 3, pp. 193-197, Apr. 1997.
Wathey, J.C. et al., Numerical reconstruction of the quantal event at nicotinic synapses; Biophys. J., vol. 27: pp. 145-164, Jul. 1979.
Watkins, L.R. et al., Blockade of interleukin-1 induced hyperthermia by subdiaphragmatic vagotomy: evidence for vagal mediation of immune-brain communication, Neurosci. Lett., vol. 183(1-2), pp. 27-31, Jan. 1995.
Watkins, L.R. et al., Implications of immune-to-brain communication for sickness and pain, Proc. Natl. Acad. Sci. U.S.A., vol. 96(14), pp. 7710-7713, Jul. 6, 1999.
Webster's Dictionary, definition of "intrathecal", online version accessed Apr. 21, 2009.
Weiner, et al., "Inflammation and therapeutic vaccination in CNS diseases," Nature., vol. 420(6917): pp. 879-884, Dec. 19-26, 2002.
Westerheide et al.; Stress-inducible regulation of heat shock factor 1 by the deacetyiase SIRT1.; Science; Vo. 323; No. 5717; pp. 1063-1066; Feb. 2009.
Whaley, K. et al., C2 synthesis by human monocytes is modulated by a nicotinic cholinergic receptor, Nature, vol. 293, pp. 580-582, Oct. 15, 1981.
Woiciechowsky, C. et al., Sympathetic activation triggers systemic interleukin-10 release in immunodepression induced by brain injury, Nature Med., vol. 4, No. 7, pp. 808-813, Jul. 1998.
Yeh, S.S. et al., Geriatric cachexia: the role of cytokines, Am. J. Clin. Nutr., vol. 70(2), pp. 183-197, Aug. 1999.
Yu et al.; Low-level transcutaneous electrical stimulation of the auricular branch of the vagus nerve: a non-invasive approach to treat the initial phase of atrial fibrillation; Heart Rhythm; 10(3); pp. 428-435; Mar. 2013.
Zamotrinsky et al.; Vagal neurostimulation in patients with coronary artery disease; Auton. Neurosci.; 88(1-2); pp. 109-116; Apr. 2001.
Zhang et al., Tumor necrosis factor, The Cytokine Handbook, 3rd ed., Ed. Thompson, Academic Press, pp. 517-548, Jul. 1, 1998.
Zhang et al.; Roles of SIRT1 in the acute and restorative phases following induction of inflammation.; J Biol Chem.; vol. 285; No. 53; pp. 41391-41401; Dec. 2010.
Zhang et al.; Chronic vagus nerve stimulation improves autonomic control and attenuates systemic inflammation and heart failure progression in a canine high-rate pacing model; Circulation Heart Fail.; 2; pp. 692-699; Nov. 2009.
Zhao et al.; Transcutaneous auricular vagus stimulation protects endotoxemic rat from lipopolysaccharide-induced inflammation, Evid. Based Complement Alternat. Med.; vol. 2012; Article ID 627023; 10 pages; Dec. 29, 2012.
Faltys et al.; U.S. Appl. No. 16/544,882 entitled "Neural stimulation devices and systems for treatment of chronic inflammation," filed Aug. 19, 2019.
Manogue; U.S. Appl. No. 16/582,726 entitled "Methods and apparatuses for reducing bleeding via coordinated trigeminal and vagal nerve stimulation," filed Sep. 25, 2019.
Tracey et al.; U.S. Appl. No. 17/170,772 entitled "Treatment of bleeding by non-invasive stimulation," filed Feb. 8, 2021.
Koopman et al., Pilot study of stimulation of the cholinergic anti-inflammatory pathway with an implantable vagus nerve stimulation device in patients with rheumatoid arthritis: 2012 ACR/ARHP Annual Meeting; Abstract No. 451: 4 pages; retrieved from the internet (https://acrabstracts.org/abstract/pilot-study-of-stimulation-of-the-cholinergic-anti-inflammatory-pathway-with-an-implantable-vagus-nerve-stimulation-device-in-patients-with-rheumatoid-arthritis); (Abstract Only); on Sep. 24, 2020.
Pavlov et al.; The cholinergic anti-inflammatory pathway; Brain, Behavior, and Immunity; 19; p. 493-499; Nov. 2005.
Zitnik et al.; Treatment of chronic inflammatory diseases with implantable medical devices; Cleveland Clinic Journal of Medicine; 78(Suppl 1); pp. S30-S34; Aug. 2011.
Levine et al.; U.S. Appl. No. 16/916,036 entitled "Control of vagal simulation," filed Jun. 29, 2020.
Housley et al.; Biomarkers in multiple sclerosis; Clinical Immunology; 161(1); pp. 51-58; Nov. 2015.
Katsavos et al.; Biomarkers in multiple sclerosis: an up-to-date overview; Multiple Sclerosis International; vol. 2013, Article ID 340508, 20 pages; (year of pub. sufficiently earlier than effective US filing date and any foreign priority date) 2013.
Faltys et al.; U.S. Appl. No. 16/785,400 entitled "Systems and methods for establishing a nerve block," filed Feb. 7, 2020.
Palov et al.; The cholinergic anti-inflammatory pathway: a missing link in neuroimmunomodulation; Molecular Medicine; 9(5); pp. 125-134; May 2003.
Koopman et al.; THU0237 first-in-human study of vagus nerve stimulation for rheumatoid arthritis: clinical and biomarker results through day 84; Annals of the Rheumatic Diseases; 72(Suppl 3):A245; Jun. 1, 2013 (Abstract Only).
Koopman et al.; Vagus nerve stimulation inhibits cytokine production and attenuates disease severity in rheumatoid arthritis; Proceedings of the National Academy of Sciences; 113(29); pp. 8284-8289; Jul. 19, 2016.
Mayo Clinic; The factsheet of vagus nerve stimulation from the Mayo Clinic website: www.mayoclinic.org/tests-procedures/vagus-nerve-stimulation/about/pac-20384565; retrieved from the internet on Sep. 28, 2021.
Levine et al.; U.S. Appl. No. 17/599,594 entitled "Vagus nerve stimulation to treat neurodegenerative disorders," filed Sep. 29, 2021.

* cited by examiner

IMPLANTABLE NEUROSTIMULATOR HAVING POWER CONTROL AND THERMAL REGULATION AND METHODS OF USE

CROSS REFERENCE TO RELATED APPLICATIONS

This patent application is a division of U.S. patent application Ser. No. 15/415,764, titled "IMPLANTABLE NEUROSTIMULATOR HAVING POWER CONTROL AND THERMAL REGULATION AND METHODS OF USE," filed on Jan. 25, 2017, which claims priority to U.S. Provisional Patent Application No. 62/286,951, titled "POWER CONTROL AND THERMAL REGULATION OF AN IMPLANTABLE NEURO STIMULATOR," filed on Jan. 25, 2016; U.S. Provisional Patent Application No. 62/340,937, titled "POWER CONTROL AND THERMAL REGULATION OF AN IMPLANTABLE NEURO STIMULATOR," filed on May 24, 2016; and U.S. Provisional Patent Application No. 62/286,955, titled "IMPLANTABLE MICROSTIMULATORS," filed on Jan. 25, 2016, each of which is herein incorporated by reference in its entirety.

This patent application may be related to U.S. patent application Ser. No. 14/887,192, titled "NEURAL STIMULATION DEVICES AND SYSTEMS FOR TREATMENT OF CHRONIC INFLAMMATION," filed Oct. 19, 2015, which is a continuation of U.S. patent application Ser. No. 14/508,940, titled "NEURAL STIMULATION DEVICES AND SYSTEMS FOR TREATMENT OF CHRONIC INFLAMMATION," filed Oct. 7, 2014, now U.S. Pat. No. 9,162,064, which is a continuation of U.S. patent application Ser. No. 14/082,047, titled "NEURAL STIMULATION DEVICES AND SYSTEMS FOR TREATMENT OF CHRONIC INFLAMMATION," filed Nov. 15, 2013, now U.S. Pat. No. 8,855,767, which is a divisional of U.S. patent application Ser. No. 12/978,250, titled "NEURAL STIMULATION DEVICES AND SYSTEMS FOR TREATMENT OF CHRONIC INFLAMMATION," filed on Dec. 23, 2010, now U.S. Pat. No. 8,612,002, which claims priority to U.S. Provisional Patent Application Nos. 61/289,946, titled "LEADLESS CUFF MICROSTIMULATOR STIMULATOR," filed on Dec. 23, 2009; and 61/306,849, titled "NEURAL STIMULATION DEVICES AND SYSTEMS FOR TREATMENT OF CHRONIC INFLAMMATION," filed on Feb. 22, 2010. Also incorporated by reference herein is: abandoned U.S. patent application Ser. No. 12/874,171, titled "PRESCRIPTION PAD FOR TREATMENT OF INFLAMMATORY DISORDERS" filed Sep. 1, 2010, each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are implantable microstimulators (e.g., neural stimulation systems and devices) that may include a static magnetic field detector for emergency shut-off of the implant. These implants may be configured to negotiate with an external charger (via inductive coils) to control charging power based at least in part an estimate of implant temperature, e.g., surface temperature, derived by the charger. The implant may alternatively or additionally negotiate the charging level provided by the charger to extend communication between the implant and the charger. In particular, the apparatuses (systems and devices, including implants and/or chargers) described herein may be configured for electrically stimulating one or more nerves (e.g., the vagus nerve) to treat chronic inflammation by modulation of the inflammatory response (via the nicotinic cholinergic anti-inflammatory pathway)

BACKGROUND

Implantable electrical stimulation devices have been developed for therapeutic treatment of a wide variety of diseases and disorders. For example, implantable cardioverter defibrillators (ICDs) have been used in the treatment of various cardiac conditions. Spinal cord stimulators (SCS), or dorsal column stimulators (DCS), have been used in the treatment of chronic pain disorders including failed back syndrome, complex regional pain syndrome, and peripheral neuropathy. Peripheral nerve stimulation (PNS) systems have been used in the treatment of chronic pain syndromes and other diseases and disorders. Functional electrical stimulation (FES) systems have been used to restore some functionality to otherwise paralyzed extremities in spinal cord injury patients.

Typical implantable electrical stimulation systems may include one or more programmable electrodes on a lead that are connected to an implantable pulse generator (IPG) that contains a power source and stimulation circuitry. However, these systems can be difficult and/or time consuming to implant, as the electrodes and the IPG are usually implanted in separate areas and therefore the lead must be tunneled through body tissue to connect the IPG to the electrodes. Also, leads are susceptible to mechanical damage over time, particularly as they are usually thin and long.

Recently, small implantable neural stimulator technology, i.e. microstimulators, having integral electrodes attached to the body of a stimulator has been developed to address the disadvantages described above. This technology allows the typical IPG, lead and electrodes described above to be replaced with a single integral device. Integration of the lead has several advantages including reduction of surgery time by eliminating, for example, the need for implanting the electrodes and IPG in separate places, the need for a device pocket, the need for tunneling to the electrode site, and requirements for strain relief ties on the lead itself. Reliability may therefore be increased significantly, especially in soft tissue and across joints because active components, such as lead wires, are now part of the rigid structure and are not subject to the mechanical damage due to repeated bending or flexing over time.

Unfortunately, the currently developed leadless devices tend to be larger and more massive than desirable, and even than traditional electrode/lead assemblies, making it difficult to stably position such devices in the proper position with respect to the nerve. Without device stability, the nerve and/or surrounding muscle or tissue can be damaged due to movement of the assembly. Further these devices require long charging times, and are often difficult to control (e.g., program) and regulate. There remains a need for leadless integral microstimulator devices that can be stably positioned on the nerve and regulate their power, including power delivered by an outside charger to inductively charge the implant.

The power requirement of implantable neurostimulators may be highly limiting. The greater the power required, the longer the charging time, and the larger the implant (e.g., battery, capacitor, etc.) must be. In addition, because these devices are implanted, they must be protected or constrained from heating above internal body temperature more than a minimum amount (e.g., 2° C.), or risk damaging tissues. This may be particularly challenging when inductive charging is used to charge the implant.

Moreover, there might be unexpected situations such as circuit dysfunction or failure, sudden health condition change of the patient, unusual environment, thermistor failure, etc. A manual shut-off of the microstimulator may be needed in such emergency situations. There is a need for a manual shut off of the implantable microstimulator to protect the patients in case of emergency.

Described herein are microstimulators (MS, also referred to herein as neurostimulators, microregulators, MRs, etc.) and methods of using them that may address some of the needs identified above.

SUMMARY OF THE DISCLOSURE

Described herein are systems for the treatment of chronic inflammatory disorders that include an implantable microstimulator with a static magnetic field detector.

Any of these apparatuses may include a detector for detecting a static magnetic field of a predetermined strength to disable (e.g., turn "off", suspend, disable or prevent stimulation from the device). For example, disclosed herein include a leadless, implantable microstimulator devices (neurostimulators) for treating chronic inflammation that are configured to have an emergency shut-off that may be triggered by a predetermined static magnetic field that is externally applied near the implant. In particular, described herein are implants that are based on non-hall effect sensors for detecting the static magnetic field. This is because Hall effect sensors are typically larger and may not be appropriate for the very small, compact and low-energy neurostimulator implants described herein.

In general, the device can comprise a hermetically sealed capsule body, at least two electrically conductive capsule regions, wherein each region electrically connects to an electrode for applying stimulation to a vagus nerve. The implantable microstimulator device can comprise a resonator within the sealed capsule body. The resonator can comprise a coil and a capacitor configured to resonate at a predetermined frequency range.

The implantable microstimulator device can comprise a static magnetic field detector. The static magnetic field detector can comprise a low power pulse generator to generate pulses at the predetermined frequency range, the pulses configured to be introduced into the resonator, and a detection circuit configured to monitor a decay rate of the pulses. The implantable microstimulator device can further comprise a battery within the sealed capsule body, and an electronic assembly within the sealed capsule body. The electronic assembly comprises power management circuitry configured to receive power from the resonator to charge the battery, a microcontroller configured to control stimulation of the vagus nerve from the conductive capsule regions, and an emergency shut-off control configured to shut down the device when the decay rate increases to a predetermined threshold decay rate.

In some variations, a magnet can be placed near the implantable microstimulator to trigger the static magnetic field detector and cause an emergency shut off of the micro stimulator. In some variations, the static magnetic field detector can comprise a resonator built in the microstimulator. The resonator can utilize an antenna, which is configured to receive power from an external charger. The antenna can comprise a coil of wire with a ferrite core to form an inductor with a defined inductance. This inductor can be coupled with a capacitor and a resistance to form a resonant circuit (RLC circuit). An external high quality NPO capacitor can be used to set the tank frequency. The frequency can be set to that of the radiated electric field to receive power and data from the external source. For example, the resonator can be a coil and capacitor configured to resonate at about 131 KHz+/−2%. The coil can be constructed with many turns of magnet wire with a target inductance of about 20 uH.

The static magnetic field detector can comprise a low power pulse generator. For example, the pulse generator can be an ultra-low power pulse generator based on a ring oscillator with the power between 1 nanowatt and 10 microwatts. In some other variations, the power of the pulse generator can be between 1 nanowatt and 1 microwatt. The low power pulse from the pulse generator can be introduced into the coil or the resonator RLC circuit. When the coil is tuned, the low power pulses can take a relatively long time to decay. But when a magnetic field is introduced to the coil, the coil is detuned. Therefore, the decay rate is much quicker (or time constant is smaller).

The static magnetic field detector can further comprise a detection circuit. The detection circuit can be configured to monitor the decay rate of the pulses or time constant of the resonator. The static magnetic field detector can be configured to shut down the microstimulator when the decay rate is increased to a predetermined value. The static magnetic field detector can be configured to shut down the microstimulator when the decay rate is 1.5, 2, 2.5, 3, 4, 5, 10 times of the previous value or any values therebetween. Values outside the above range are also possible. In some variation, the static magnetic field detector can be configured to shut down the microstimulator by using h a shorting switch. In some variations, the low power pulses can be introduced periodically, such as every second, to detect the presence of the magnetic field. In some other variations, the low pulses can be introduced continuously to monitoring the presence of the magnetic field.

In some variations the static magnetic field is detected using a Wiegand material (e.g., a material, such as a Wiegand wire exhibiting the Wiegand effect).

Methods of shutting down an implantable microstimulator device are also described herein. For example, described herein are methods of shut down an implantable microstimulator device by using a static magnetic field detector.

In some variations these methods may include the steps of: generating pulses by a low power pulse generator, introducing the pulses into an RLC resonator, monitoring a decay rate of the pulses, and shutting down the device when the decay rate increases to a predetermined threshold decay rate.

In some variations, the method of shutting down the device by the static magnetic field detector can comprise utilizing a built-in receiving coil of the micro stimulator. In some other variations, the method can comprise utilizing another RLC resonator of the micro stimulator.

In some variation, the method can comprise placing a magnet near the device. In some variation, the method can further comprise shutting down the device when the predetermined threshold decay rate increases 1.5, 2, 5, 10 times any values therebetween. In some variation, the method can comprise using a shorting switch configured to shut down the device.

In some variation, a power of the pulses from the low pulse generator is between 1 nanowatt and 10 microwatts. In some other variation, a power of the pulses is between 1 nanowatt and 1 microwatts. In some variation, the low power pulses are introduced periodically. In some other variation, the low power pulses are introduced continuously.

The above summary of the invention is not intended to describe each illustrated embodiment or every implementation of the present invention, but to highlight certain key features. The figures and the detailed description that follow more particularly exemplify these embodiments and features.

In addition or alternatively, any of the neurostimulators and chargers for charging these neurostimulators described herein include control circuitry that negotiates and controls the power applied by the charger to prevent overheating of the implanted neurostimulator, while still rapidly and efficiently charging the implant. For example, described herein are chargers for inductively charging a neurostimulator implanted within a portion of the patient's body. A charger may include: an energizer coil; an amplifier configured to drive an electrical current through the energizer coil to generate an electromagnetic field; and a controller comprising a power control loop configured to modulate the electrical current driven through the energizer coil based on an estimate of a tank voltage of the neurostimulator (PWRIN), to prevent a surface temperature of the neurostimulator from exceeding a predetermined threshold relative to the body temperature of the patient.

A charger for inductively charging a neurostimulator implanted within a portion of the patient's body may also or alternatively include: an energizer coil; an amplifier configured to drive an electrical current through the energizer coil to generate an electromagnetic field; and a controller comprising a power control loop configured to modulate the electrical current driven through the energizer coil such that a surface temperature of the neurostimulator remains within about 2 degrees Celsius of the body temperature of the patient.

The power control loop may be configured to modulate the electrical current driven through the energizer coil based on a measurement of a change in voltage across the energizer coil when the energizer coil is in an unloaded state and a loaded state from charging the neuro stimulator.

The power control loop may be configured to modulate the electrical current driven through the energizer coil based on a power control loop parameter, wherein the power control loop parameter is based on a set power level of the amplifier and a measurement of a change in voltage across the energizer coil when the energizer coil is in an unloaded state and a loaded state from charging the neurostimulator.

In some variations, the set power level and change in voltage may be multiplied together to yield the power control loop parameter.

The power control loop may be configured to modulate the current driven through the energizer coil such that the power control loop parameter is maintained at approximately a predetermined target value. The predetermined target value may be based on an identification of the charger and the neurostimulator. The predetermined target value may further be based on an identification of one or more characteristics of the inductive coupling between the charger and the neurostimulator. The power control loop may be configured to duty cycle the electric current driven through the energizer coil when the change in voltage across the energizer coil is not detected. The power control loop may further comprise a pulse width modulator, wherein the pulse width modulator is configured to be duty cycled when the change in voltage across the energizer coil is not detected. The power control loop may be configured to duty cycle the electric current driven through the energizer coil when the TxH is greater than a predetermined value.

Also described herein are methods of inductively charging a microstimulator with a charger. For example a method of charging (e.g., to prevent overheating of the outside of the implant above a few degrees) may include: determining a change in voltage across an energizer coil of the charger when the energizer coil is in an unloaded state and a loaded state; and modulating a set power level of the energizer coil based on the determined changed in voltage across the energizer coil.

The power level may be modulated by setting the power level such that the power level multiplied by the change in voltage equals a predetermined value.

Any of these methods may include duty cycling the energizer coil when the change in voltage is not detected, and/or determining the charger type and the microstimulator type. The power level may be modulated by setting the power level such that the power level multiplied by the change in voltage equals a predetermined value, wherein the predetermined value is based on the charger type and the microstimulator type.

Although the implants described herein are shown and described as implantable in the neck (e.g., carotid) region of the vagus nerve, any of these implants may be inserted in other body regions, including in particular the subdiaphragmatic region (see, e.g., U.S. patent application Ser. No. 15/433,936). Furthermore, the implants described typically include batteries; in some variations any of these implants may not include a battery (e.g., "batteryless" implants that may apply stimulation in the presence of the inductive field, also described in U.S. patent application Ser. No. 15/433, 936, herein incorporated by reference in its entirety).

DETAILED DESCRIPTION

Figure 1A:
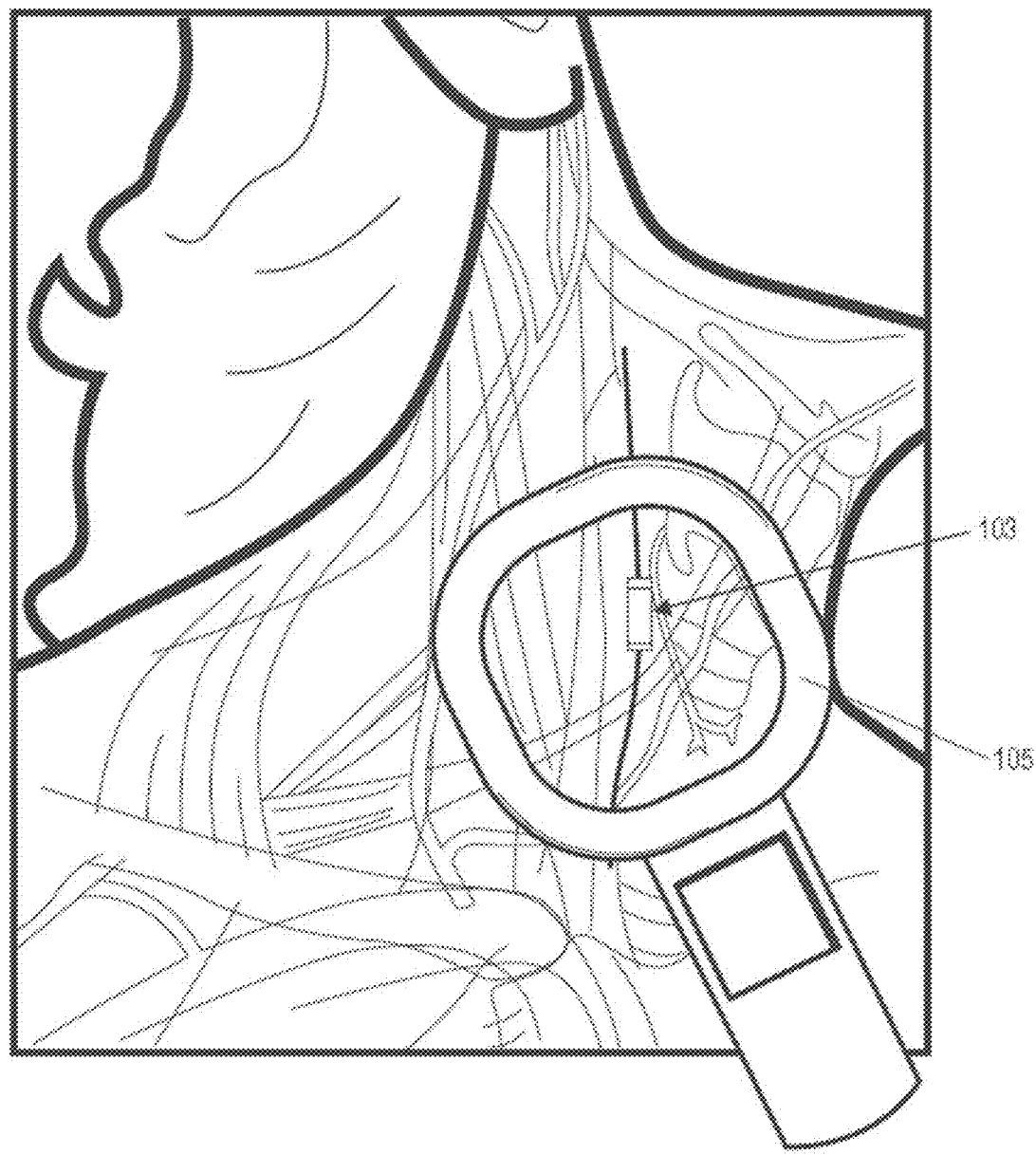
FIG. 1A shows one variation of a system for modulating chronic inflammation including a leadless microstimulator (shown connected to the vagus nerve) and an external charger/controller. This apparatus may be adapted or configured to include an emergency shut-off mechanism as described herein (e.g., a static magnetic field detector) and/or it may be configured to negotiate between the charger and the implant to regulate the applied power.

Systems for electrically stimulating one or more nerves to treat chronic inflammation may include an implantable, wireless microstimulator such as those described herein and an external charging device (which may be referred to as a charging wand, charger, or energizer). In some variations the system also includes a controller such as a "prescription pad" that helps control and regulate the dose delivered by the system. The microstimulator may be secured in position using a securing device (which may be referred to as a "POD") to hold the microstimulator in position around or adjacent to a nerve. These microstimulators are designed and adapted for treatment of chronic inflammation, and may be configured specifically for such use. Thus, an implantable microstimulator may be small, and adapted for the low duty-cycle stimulation to modulate inflammation. For example, the implantable microstimulator may hold a relatively small amount of power over weeks or even months and discharge it at a rate sufficient to modulate the antiinflammatory pathway without significantly depressing heart rate or triggering any number of unwanted effects from the vagus nerve or other neural connections. Any of the nerves of the inflammatory reflex, including the vagus nerve, may be treated as described herein using the systems described.

Any of these apparatuses (systems and devices, including microstimulators and chargers) may be adapted to include one or more of an emergency shutoff, which may be based on a static magnetic field detector, and/or a thermal control or regulation based on the power in ("PWRIN") of the microstimulator. The thermal regulator may be configured to modulate the power applied by the inductive coupling between the external charger and the microstimulator (implant), as will be described in greater detail below. In general, the microstimulator may include a power negotiation protocol. This protocol may be hardware, firmware and/or software, and may regulate charger function, including switching the charger on or off (including altering the duty cycle of the charger). The power negotiation protocol may be on the charger, the micro stimulator, or both. For example, a controller of the microstimulator may execute a power negotiation protocol to negotiate at whap power the battery will charge at. The microstimulator may exchange data with and between the charger, at least in part to negotiate what power level the MS will draw power from the charger; if the MS attempts to draw too much power from the charger, it may delay or stop communication between the MS and the charger. Thus, the power negotiation protocol may throttle down the power drawn by the MS, thereby extending communication between the MR and the charger, permitting further telemetry. Initially, the charger and implant may exchange identifying information, such as charger type (capability, e.g., coil size, etc.), implant type (e.g., inductive coil size(s), etc.), coupling between the two, etc. Once communication has been initiated, the apparatus may then negotiate what level the charger will charge the implant (e.g., what applied voltage, current, power, etc.).

Any of these apparatuses may use an intermediate field communication link (e.g., when the implant is running off of a battery), including a high-gain amplifier to amplify an RF signal from the charger, using the battery rather than charging it during initial communication between the charger and implant, which may allow longer range.

As mentioned, in general, the apparatuses described herein may include an implant (micro stimulator) and a charger. For example, FIG. 1 illustrates one variation of a system for treating chronic inflammation that includes a microstimulator contained in nerve cuff (e.g., "POD") that is mounted on cervical vagus nerve and charged a programmed by an external charger/programmer unit. This variation of a system includes a microstimulator 103 that has been implanted to contact the vagus nerve as shown. The implant may be programmed, controlled and/or charged by a charger/controller 105 device. In this variation the charger/controller is a loop with a wand region.

Figure 1B:
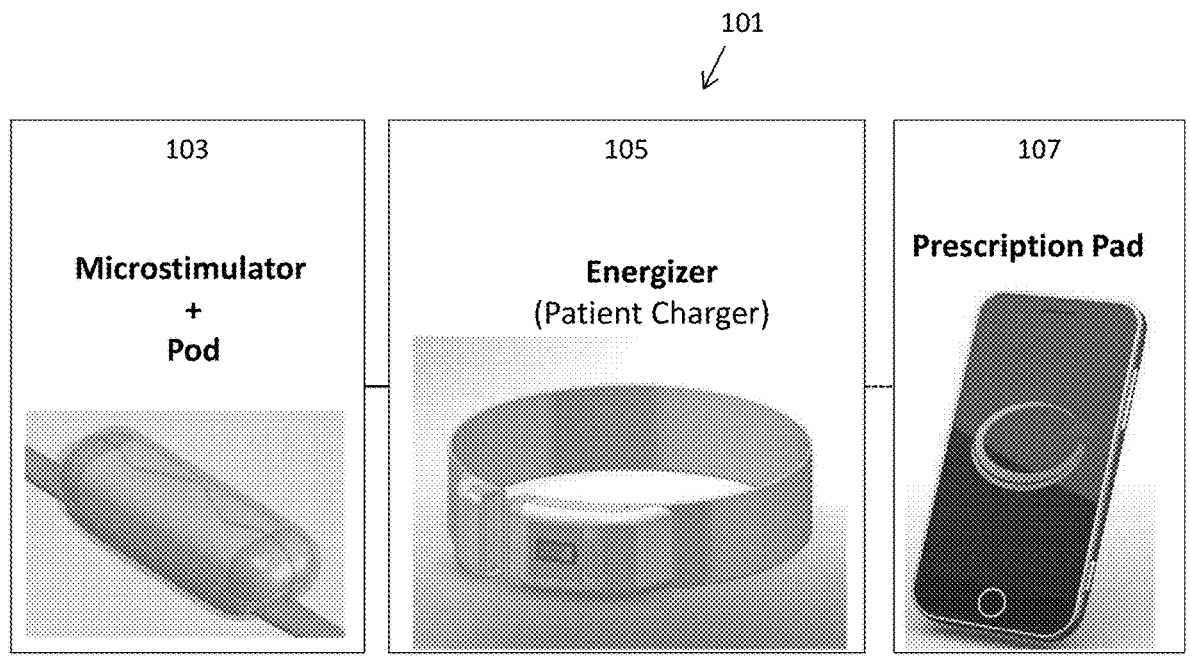
FIG. 1B shows a system for modulating chronic inflammation, including a micro stimulator, charger ("energizer"), and system programmer/controller ("prescription pad").

FIG. 1B shows another variation of a system for treating chronic inflammation that also includes an implantable microstimulator 103 (shown inserted into a POD to hold it in position relative to a nerve) and a charging device ("energizer" 105) configured as a collar to be worn around the subject's neck and charge the implant. Optionally, the system may include a separate controller ("prescription pad" 107) which may be a separate dedicated device or part of a mobile or other handheld device (e.g., an application to run on a handheld device) and may provide control information to and receive data from (e.g., telemetry) the microstimulator via the charger (or in some variations, directly).

Figure 1C:
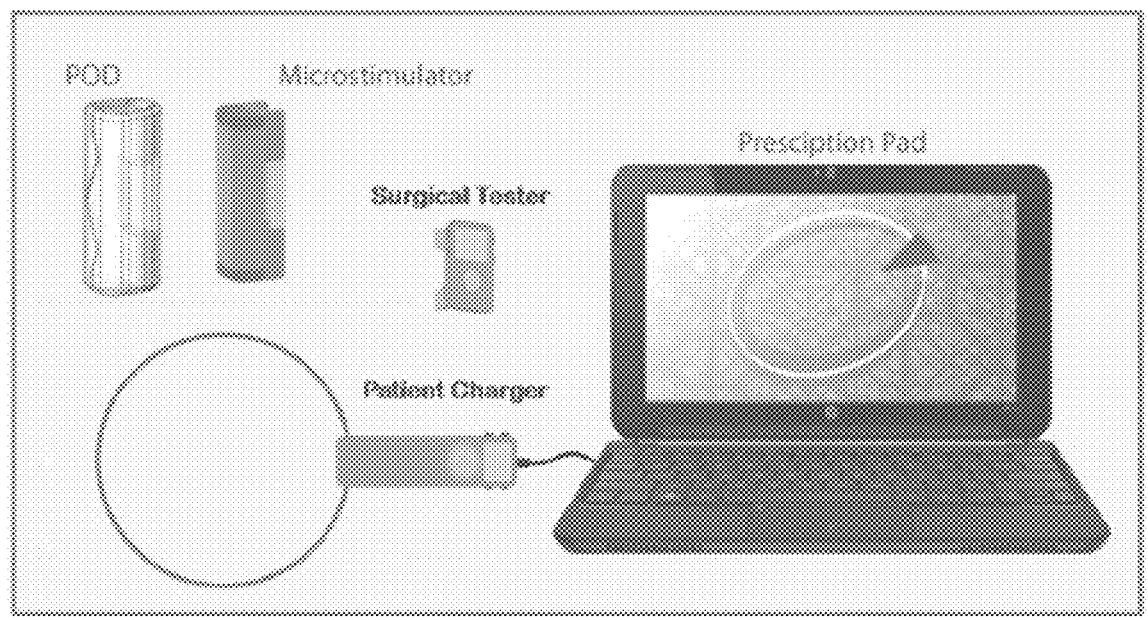
FIG. 1C shows a system for modulating chronic inflammation, including a micro stimulator, a securing device (POD) for securing the leadless stimulator to the nerve, an external charger, a system programmer/controller ("prescription pad") and an optional surgical tester.
Figure 1D:
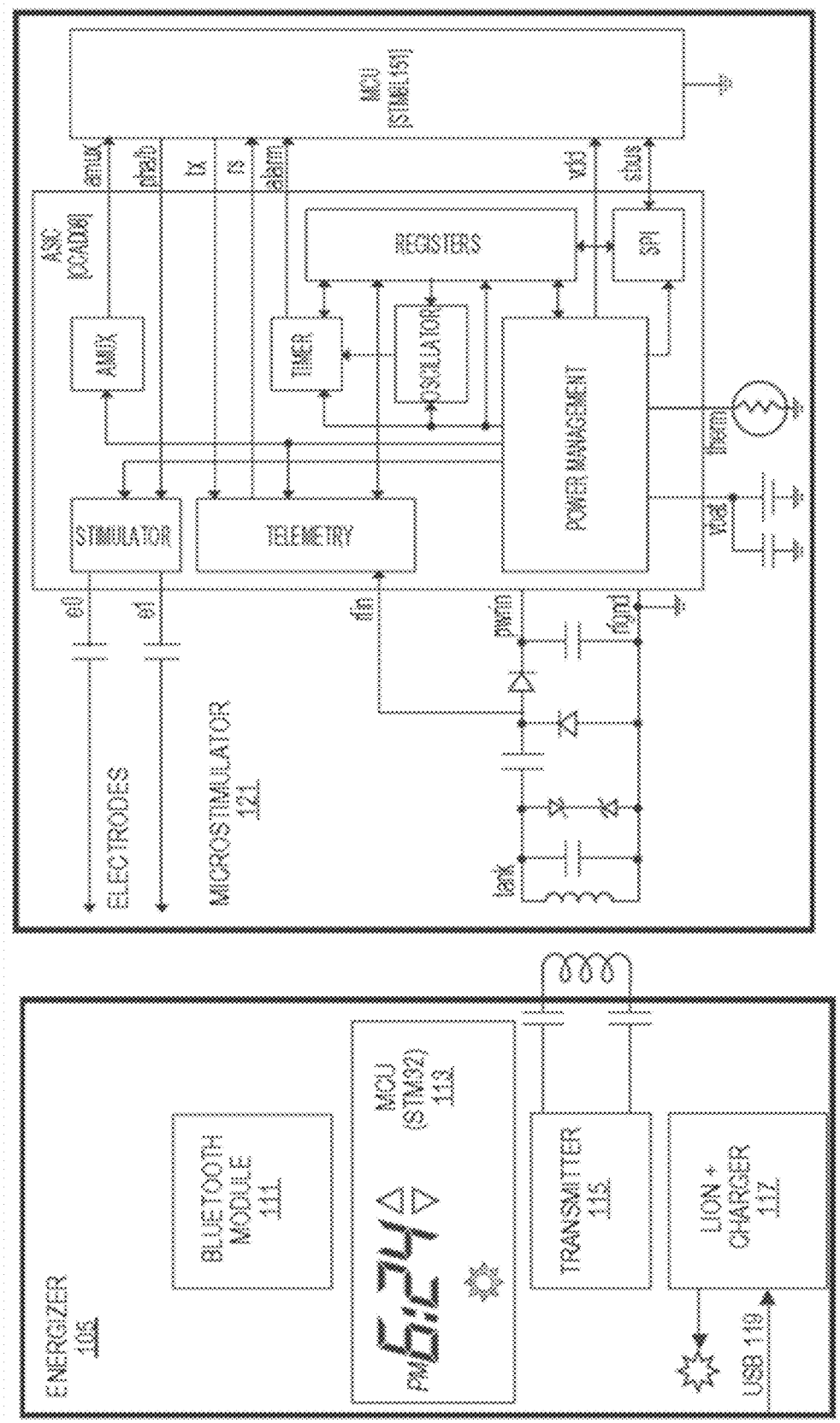
FIG. 1D is a block diagram schematically illustrating a microstimulator and a charger.
Figure 2:
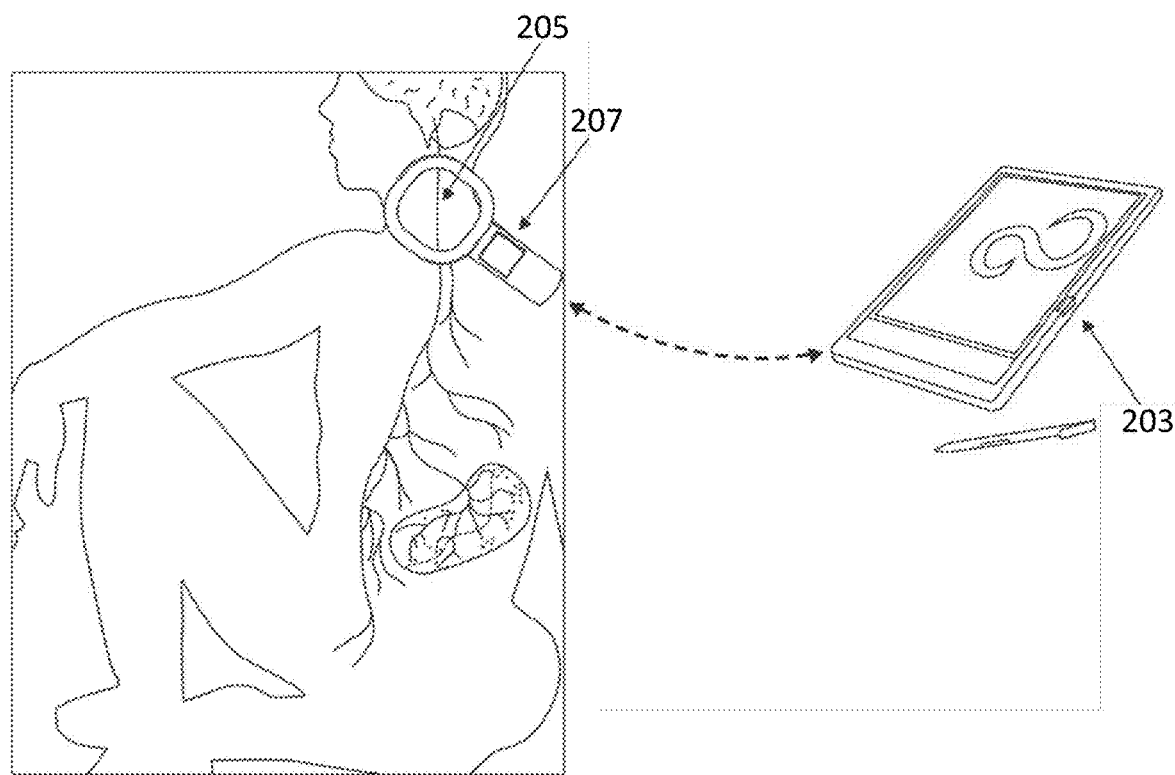
FIG. 2 illustrates one variation of a system including an external programmer/controller wirelessly connected to a microstimulator, which may communicate with the implant through the charger as illustrated.

FIG. 1C shows another variation of a system for treating chronic inflammation. The systems described herein may also be referred to as systems for the neural stimulation of the cholinergic anti-inflammatory pathway (NCAP). These systems may be configured as chronic implantable systems. In some variations, the systems are configured to treat acutely (e.g., acute may 8 hours or less), sub-acutely (expected to occur for fewer than 30 days), or chronically (expected to occur for more than 30 days).

In general, the systems described herein may be configured to apply electrical stimulation at a minimum level necessary to modulate the inflammatory reflex (e.g., modulating cytokine release) characterized by the Chronaxie and rheobase. Chronaxie typically refers to the minimum time over which an electric current double the strength of the rheobase needs to be applied in order to stimulate the neuron. Rheobase is the minimal electrical current of infinite duration that results in an action potential. As used herein, cytokines refer to a category of signaling proteins and glycoproteins that, like hormones and neurotransmitters, are used extensively in cellular communication.

The NCAP Systems described herein are typically intended for the treatment of chronic inflammation through the use of implanted neural stimulation devices (micro stimulators) to affect the Neural Stimulation of the Cholinergic Anti-inflammatory Pathway (NCAP) as a potential therapeutic intervention for rheumatologic and other inflammation-mediated diseases and disorders. Neuro stimulation of the Cholinergic Anti-inflammatory Pathway (NCAP) has been shown to modulate inflammation. Thus, the treatment and management of symptoms manifested from the onset of disease (e.g., inflammatory disease) is based upon the concept of modulating the Cholinergic Anti-inflammatory Pathway. The NCAP pathway normally maintains precise restraint of the circulating immune cells. As used herein, the CAP is a reflex that utilizes cholinergic nerve signals traveling via the Vagus nerve between the brain, chemoreceptors, and the reticuloendothelial system (e.g., spleen, liver). Local release of pro-inflammatory cytokines (e.g., tumor necrosis factor or TNF) from resident immune cells is inhibited by the efferent, or indirectly by afferent vagus nerve signals. NCAP causes important changes in the function and microenvironment of the spleen, liver and other reticuloendothelial organs. Leukocytes which circulate systemically become "educated" as they traverse the liver and spleen are thereby functionally down regulated by the affected environment of the reticuloendothelial system. This effect can potentially occur even in the absence of an inflammatory condition.

Under this model, remote inflammation is then dampened by down-regulated cytokine levels. Stimulation of the vagus nerve with a specific regiment of electrical pulses regulates production of pro-inflammatory cytokines. In-turn, the down regulation of these cytokines may reduce localized inflammation in joints and other organs of patients with autoimmune and inflammatory disorders.

The NCAP System includes a neurostimulator that may trigger the CAP by stimulating the cervical vagus nerve. The NCAP System issues a timed burst of current controlled pulses with sufficient amplitude to trigger the CAP at a particular interval. These two parameters, Dose Amplitude and Dose Interval, may be used by a clinician to adjust the device. For example, the clinician may set the Dose Amplitude by modifying the current level. The Dose Interval may be set by changing the duration between Doses (e.g. 12, 24, 48 hours).

In some variations, dose amplitude may be set to within the Therapy Window. The Therapy window is defined as the lower limit of current necessary to trigger the CAP, and the upper limit is the level at which the Patient feels uncomfortable. The lower limit is called the Threshold (T), and the uncomfortable level is called Upper Comfort Level (UCL).

Dose Amplitude thresholds are nonlinearly dependent upon Current (I), Pulse width (PW), Pulse Frequency (PF), and Burst Duration (BD). Amplitude is primarily set by charge (Q), that is Current (I)×Pulse width (PW). In neurostimulation applications current has the most linear relationship when determining thresholds and working within the therapy window. Therefore, the clinician may modify Dose Amplitude by modifying current. The other parameters are held to experimentally determined defaults. Pulse width is selected to be narrow enough to minimize muscle recruitment and wide enough to be well above the chronaxie of the targeted neurons. Stimulus duration and pulse frequency was determined experimentally in Preclinical work.

Dose Interval may be specific for particular diseases and the intensity of diseases experienced by a patient. Our initial research has indicated that the cervical portion of the vagus nerve may be an ideal anatomic location for delivery of stimulation. The nerve runs through the carotid sheath parallel to the internal jugular vein and carotid artery. At this location, excitation thresholds for the vagus are low, and the nerve is surgically accessible. We have not found any significant difference in biomarker modulation (e.g., modulation of cytokines) between right and left. Even though the right vagus is thought to have lower thresholds than the left in triggering cardiac dysrythmias, the thresholds necessary for NCAP are much lower than those expected to cause such dysrythmias. Therefore a device delivering NCAP can safely be applied to either the right or left vagus.

We have also found, surprisingly, that the Therapy Window is maximized on the cervical vagus through the use of a bipolar cuff electrode design. Key parameters of the cuff may be: spacing and shielding of the contacts. For example, the contact points or bands may be spaced 1-2 diameters of the vagus nerve apart, and it may be helpful to shield current from these contacts from other nearby structures susceptible to inadvertent triggering. The cuff may be further optimized by using bands which are as long and wide as possible to reduce neurostimulator power requirements.

Figure 3A:
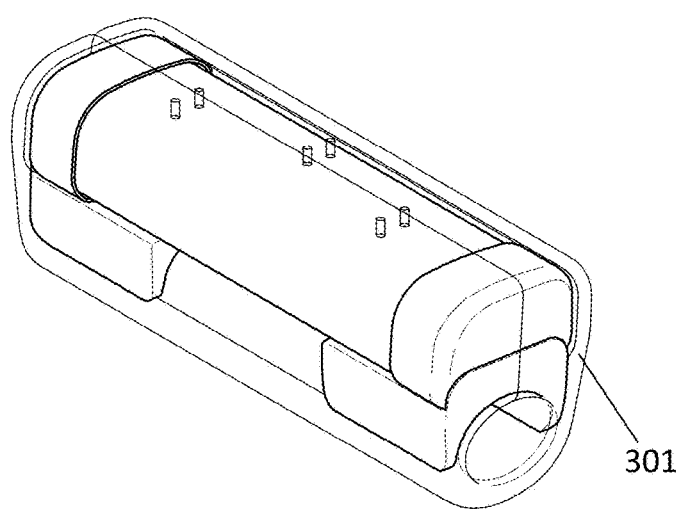
FIG. 3A shows one variation of a microstimulator in a POD configured to surround a nerve of the inflammatory reflex.
Figure 3B:
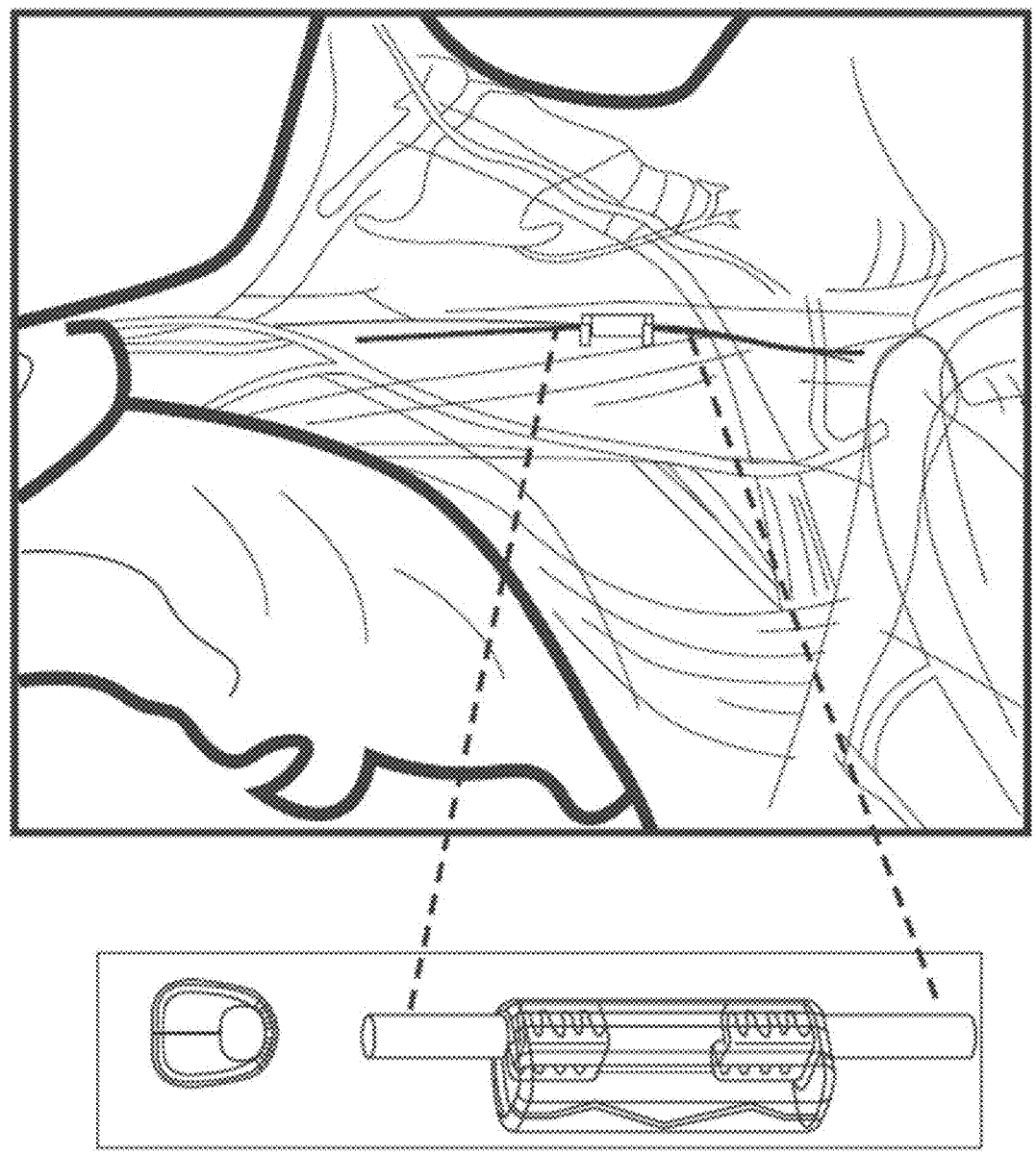
FIG. 3B shows an enlarged view of the microstimulator and POD.

Thus, any variations of the systems described herein (e.g., the NCAP system) may be implemented with a Cuff, Lead and Implantable Pulse Generation (IPG), or a Leadless Cuff. The preferred implementation is a leadless cuff implemented by a microstimulator with integral electrode contacts in intimate contact with the nerve and contained within a Protection and Orientation Device (POD). This is illustrated in FIGS. 3A and 3B. The POD 301 may form a current shield, hold the microstimulator into place against the vagus nerve, and extend the microstimulator integral contacts with integral contacts in the POD itself. The POD is typically a polymer shell that encapsulates a microstimulator implant and that allows a nerve to run through the interior against the shell wall parallel to the length of the microstimulator implant. Within the shell of the POD, the microstimulator implant remains fixed against the Vagus nerve so the electrodes remain in contact with the nerve. The POD anchors the implant in place and prevents the implant from rotating or separating from the nerve, as well as maintaining contact between the electrodes and the nerve and preserving the orientation as necessary for efficient external charging of the microstimulator battery.

Referring back to FIG. 1C, the system may include an implantable microstimulator contained in a POD, a Patient Charger, and a prescription pad that may be used by the clinician to set dosage parameters for the patient. This system may evaluate the efficacy, safety, and usability of an NCAP technology for chronic treatment of clinical patients. The system can employ a Prescription Pad (external controller) that may include the range of treatment options.

As described in more detail in U.S. Ser. No. 12/874,171 (titled "PRESCRIPTION PAD FOR TREATMENT OF INFLAMMATORY DISORDERS"), previously incorporated by reference in its entirety, the Prescription Pad may incorporate workflows in a simplified interface and provide data collection facilities that can be transferred to an external database utilizing commercially robust and compliant methods and procedures. In use, the system may be recommended for use by a clinician after assessing a patient; the clinician may determine that treatment of chronic inflammation is warranted. The clinician may then refer the patient to an interventional doctor to implant the microstimulator. Thereafter then clinician (or another clinician) may monitor the patient and adjust the device via a wireless programmer (e.g. prescription pad). The clinician may be trained in the diagnosis and treatment procedures for autoimmune and inflammatory disorders; the interventional placement of the system may be performed by a surgeon trained in the implantation of active neuro stimulation devices, with a sufficient depth of knowledge and experience regarding cervical and vagal anatomy, experienced in performing surgical dissections in and around the carotid sheath.

The system may output signals, including diagnostics, historical treatment schedules, or the like. The clinician may adjust the device during flares and/or during routine visits. Examples of implantation of the microstimulator were provided in U.S. Ser. No. 12/874,171. For example, the implant may be inserted by making an incision in the skin (e.g., ≈3 cm) along Lange's crease between the Facial Vein and the Omohyoid muscle, reflecting the Sternocleidomastoid and gaining access to the carotid sheath. The IJV may be displaced, and the vagus may be dissected from the carotid wall (≤2 cm). A sizing tool may be used to measure the vagus, and an appropriate Microstimulator and POD Kit (small, medium, large) may be selected. The POD may then be inserted under nerve with the POD opening facing the surgeon, so that the microstimulator can be inserted inside POD so that the microstimulator contacts capture the vagus. The POD may then be sutured shut. In some variations a Surgical Tester may be used to activate the microstimulator and perform system integrity and impedance checks, and shut the microstimulator off, during or after the implantation. In other variations the surgical tester may be unnecessary, as described in greater detail below.

A physician may use the Patient Charger to activate the micro stimulator, perform integrity checks, and assure sufficient battery reserve exists. Electrodes may be conditioned with sub-threshold current and impedances may be measured. A Physician may charge the microstimulator. In some variations a separate charger (e.g., an "energizer") may be used by the patient directly, separate from the controller the physician may use. Alternatively, the patient controller may include controls for operation by a physician; the system may lock out non-physicians (e.g., those not having a key, code, or other security pass) from operating or modifying the controls.

In general, a physician may establish safe dosage levels. The physician may slowly increment current level to establish a maximum limit (Upper Comfort Limit). This current level may be used to set the Dosage Level. The exact procedure may be determined during this clinical phase.

The Physician may also specify dosing parameters that specify dosage levels and dosage intervals. The device may contain several concurrent dosing programs which may be used to acclimate the patient to stimulus, gradually increase dosage until efficacy is achieved, reset tachyphylaxis, or deal with unique patient situations.

As mentioned, a patient may use the Patient Charger to replenish the microstimulator battery at necessary times (e.g., every day, every week, etc.). A clinician may also work with the patient to setup a schedule based upon the patient's stimulation needs and lifestyle. In some variations, the microstimulator battery charging is achieved by expanding the Patient Charger loop, putting the loop over the head, and closing the handle to close the loop, which may position the charger sufficiently near the implanted device. Charging may start automatically or the user (patient or physician) can push a charge button. The patient may watch the progress on the Patient Charger and may be signaled when charging is complete. The length of the charge may depend primarily upon dosage level. The more often a patient charges, the shorter the charge time may be.

The charger and/or implant may include a clock, and in some variations the patient may set the time zone on the Patient Charger to reflect his/her location. The Patient Charger may update the microstimulator time parameters while charging. This may enable the patient to adjust for travel related time zone changes or daylight savings time adjustments. Because stimulation may be perceptible (felt by the patient), it may be important that the patient receive the stimulation at the same time(s) every day.

If the patient does not charge frequently enough, the system may automatically cease treatment when about 3 months of standby battery remains. Once treatment stops the patient must visit their physician to restart treatment, to avoid damage to the implant requiring re-implantation.

In general, the microstimulator and POD can be suitable for chronic treatment with a design life of 10 years or more. The battery may support a 20 year life. Microstimulator battery charging intervals may be dependent on patient dose settings, however, as described in greater detail below, the system may be configured to conserve power and therefore minimize charging intervals and/or times, greatly enhancing patient comfort and compliance.

The microstimulator and POD may be packaged into kits. Any of the systems described herein may also include a surgical kit with the items necessary for the implantation of Microstimulator and POD. This does not prevent the surgeon, during a revision, from using the existing POD and only replacing the micro stimulator. System kits may be available for small, medium, and large vagus nerves. A vagus nerve sizing kit may be available to determine which kit to use. In some variations the microstimulator and POD have a loose fit such the lumen of the device and the widest part of the nerve has a loose fit without constraining blood flow, and allowing axial flexibility and both compressive and tensile forces on the device without damaging the nerve. For example, the POD may encapsulate the microstimulator so current leakage may occur through vagus nerve access ports. All other sources of current leakage may be <25 uA when POD is sutured shut. The microstimulator may have a slot for the vagus nerve. This slot may have three sizes (approximately small, medium, large) for vagus nerves of approximately (e.g., +/−5%, 10%, 20%, 30%, 40%, 50%): 2 w×1.5 h; 3 w×2 h; 4 w×3 h (mm).

Implantable components of the microstimulator and POD and components are typically applied within the sterile barrier during the interventional procedure and may be supplied sterile. Sterilization method may be Ethylene Oxide (EO).

In some variations, the POD may be secured by 1-3 sutures and may include a marker to easily allow surgeon to match suture holes minimizing failure. The POD may be configured so that over-tightening the sutures does not cause vagal devascularization. The microstimulator and POD cross sectional area may not exceed 60 mm2 including the largest nerve model. The volume including the largest nerve model may be less than 1.5 cc.

Because rotation around the axis and movement up and down on the vagus nerve may occur during the healing period. The Patient Charger may allow accommodation of this movement.

In some variations, the microstimulator may have a bipolar stimulation current source that produce as stimulation dose with the characteristics shown in table 1, below. In some variation, the system may be configured to allow adjustment of the "Advanced Parameters" listed below; in some variations the parameters may be configured so that they are predetermined or pre-set. In some variations, the Advanced Parameters are not adjustable (or shown) to the clinician. All parameters listed in Table 1 are ±5% unless specified otherwise.

TABLE 1

| Micro stimulator parameters | | |
|---|---|---|
| Property | Value | Default |
| Dosage Amplitude (DA) | 0-5,000 µA in 25 µA steps | 0 |
| Intervals | Minute, Hour, Day, Week, Month | Day |
| Number of Doses per Interval | N = 60 Maximum | 1 |
| Advanced Parameters | | |
| Pulse width Range (PW) | 100-1,000 µS in 50 µS increments | 200 |

TABLE 1-continued

| Micro stimulator parameters | | |
|---|---|---|
| Property | Value | Default |
| Stimulus Duration (SD) | 1-1000 seconds per dose | 60 |
| Pulse Frequency (PF) | 1-50 Hz | 10 |
| Stimulus Voltage (SV) | ±3.3 or ±5.5 ± 1 Volts | Automatically set by software |
| Constant Current Output | ±15% over supported range of load impedances (200-2000Ω) | |
| Specific Dose Time | Set a specific time between 12:00 am-12:00 am in one minute increments for each Dose Issue | Driven by default table (TBD) |
| Number of Sequential Dosing Programs | 4 maximum | 1 |

The Dosage Interval is defined as the time between Stimulation Doses. In some variations, to support more advanced dosing scenarios, up to four 'programs' can run sequentially. Each program has a start date and time and will run until the next program starts. Dosing may be suspended while the Prescription Pad is in Programming Mode. Dosing may typically continue as normal while charging. Programs may be loaded into one of four available slots and can be tested before they start running. Low, Typical, and High Dose schedules may be provided. A continuous application schedule may be available by charging every day, or at some other predetermined charging interval. For example, Table 2 illustrates exemplary properties for low, typical and high dose charging intervals:

TABLE 2

| low typical and high dose charging intervals | |
|---|---|
| Property | Value |
| Low Dose Days Charge Interval | 30 days max: 250 µA, 200 µS, 60 s, 24 hr, 10 Hz, ±3.3 V |
| Typical Dose Charge Interval | 30 days max: 1,000 µA, 200 µS, 120 s, 24 hr, 10 Hz, ±3.3 V |
| High Dose Charge Interval | 3.5 days max: 5,000 µA, 500 µS, 240 s, 24 hr, 20 Hz, ±5.5 V, |

The system may also be configured to limit the leakage and maximum and minimum charge densities, to protect the patient, as shown in Table 3:

TABLE 3

| safety parameters | |
|---|---|
| Property | Value |
| Hardware DC Leakage Protection | <50 nA |
| Maximum Charge Density | 30 µC/cm$^2$/phase |
| Maximum Current Density | 30 mA/cm$^2$ |

In some variations, the system may also be configured to allow the following functions (listed in Table 4, below):

TABLE 4

Additional functions of the micro stimulator and/or controller(s)

| Function | Details |
|---|---|
| Charging | Replenish Battery |
| Battery Check | Determine charge level |
| System Check | Self Diagnostics |
| Relative Temperature | Temperature difference from baseline |
| Program Management | Read/Write/Modify a dosage parameter programs |
| Program Up/Download | Transfer entire dosage parameter programs |
| Electrode Impedances | Bipolar Impedance (Complex) |
| Signal Strength | Strength of the charging signal to assist the patient in aligning the external Charge to the implanted Microstimulator. |
| Patient Parameters | Patient Information |
| Patient History | Limited programming and exception data |
| Implant Time/Zone | GMT + Time zone, 1 minute resolution, updated by Charger each charge session |
| Firmware Reload | Boot loader allows complete firmware reload |
| Emergency Stop | Disable dosing programs and complete power down system until Prescription Pad connected |

As mentioned above, in some variations, the system may record function of the microstimulator (e.g., a limited patient history). For example, the system may record: date and time that each program that is started and the associated program parameters; power down events due undercharging; hardware or software exceptions; emergency power down events; compliance events with associated impedance measurement; etc. In some variations, at least the last 50 events may be preserved in a circular buffer. Any of the systems describe herein may be approved for MRI usage at 3 Tesla (e.g., the torque will be less than a maximum threshold, the temperature rise may be less than 4° C., and the blackout area may be less than a maximum threshold volume. In some variations, the microstimulator and POD may be configured to withstand monopolar electrocautery.

The Patient Charger (including the energizer variations) typically fits over a patient's head to charge the implants in the patient's neck. As described in greater detail below, the Patient Charger may support neck circumferences ranging between 28-48 cm and head circumferences of up to 72 cm. The implant and the charger may further be configured so that they orientation of the charger and implant may allow sufficient tolerance to permit charging when worn by the user in a number of positions, without requiring substantial repositioning. The Patient Charger may provide functionality that can be accessed through a connected Prescription Pad or other external controller. For example, Table 5 below lists some function elements that may be accessed by a prescription pad in conjunction with a charger:

TABLE 5 functions that may be performed by prescription pad and charger

| Function | Prescription Pad connected to Charger | Charger Alone |
|---|---|---|
| Charging | Y | Y |
| Battery Check | Y | Y |
| System Check | Y | Y |
| Absolute device | Y | Used for thermal |

TABLE 5-continued functions that may be performed by prescription pad and charger

| Function | Prescription Pad connected to Charger | Charger Alone |
|---|---|---|
| Temperature | | safety purposes only |
| Program Management | Y | N |
| Program Up/Download | Y | N |
| Electrode Impedances | Y | OK Check Only |
| Signal Strength | Y | Y |
| Patient Parameters | Y | N |
| Patient History | Y | N |
| Implant Time/Zone/Date | Y (time zone not changed) | Y (synced to Charger and changed by patient) |
| Firmware Reload | Y | N |
| Emergency Stop | Y | Y (special sequence) |

In general, a charger (which may be used by a patient directly) may include a recharge reminder alarm (audio and/or visual) that will remind the patient to charger on a daily, weekly, or monthly frequency. The Patient Charger may be charged through a Wall Adapter plug alone or in conjunction with a Charging Dock. The Patient Charger may clearly indicate that it is charging.

In some variations, the Patient Charger firmware will be version controlled and may be updated with Prescription Pad software in the field, or can be updated in the factory. For example, the Prescription Pad software may be controlled and may be updated in the field by the one or more web applications, a USB Dongle, a CD, etc. In some variations, the Prescription Pad may identify the microstimulator through a unique electronic ID electronically available in the microstimulator. The ID may be linked to a serial number that is embossed in the case. However, the Patient Charger may not require knowledge of this ID to charge the device.

The micro stimulators described herein are configured for implantation and stimulation of the cholinergic anti-inflammatory pathway, and especially the vagus nerve. In particular the micro stimulators described herein are configured for implantation in the cervical region of the vagus nerve to provide extremely low duty-cycle stimulation sufficient to modulate inflammation. These micro stimulators may be adapted for this purpose by including one or more of the following characteristics, which are described in greater detail herein: the conductive capsule ends of the microstimulator may be routed to separate electrodes; the conductive capsule ends may be made from resistive titanium alloy to reduce magnetic field absorption; the electrodes may be positioned in a polymer saddle; the device includes a suspension (e.g., components may be suspended by metal clips) to safeguard the electronics from mechanical forces and shock; the device may include an H-bridge current source with capacitor isolation on both leads; the device may include a built in temperature sensor that stops energy absorption from any RF source by detuning the resonator; the device may include a built-in overvoltage sensor to stop energy absorption from any RF source by detuning resonator; the system may include DACs that are used to calibrate silicon for battery charging and protection; the system may include DACs that are used to calibrate silicon for precision timing rather than relying on crystal oscillator; the system may include a load stabilizer that maintains constant load so that inductive system can communicate efficiently; the system may include current limiters to prevent a current rush so that the microstimulator will power up smoothly from resonator power source; the system may extract a clock from carrier OR from internal clock; the device may use an ultra low power accurate RC oscillator that uses stable temperature in body, DAC calibration, and clock adjustment during charging process; the device may use a solid state LIPON battery that allows fast recharge, supports many cycles, cannot explode, and is easy to charge with constant voltage; and the device may include a resonator that uses low frequency material designed not to absorb energy by high frequency sources such as MRI and Diathermy devices.

Many of these improvements permit the device to have an extremely small footprint and power consumption, while still effectively modulating the vagus nerve.

Figure 4:
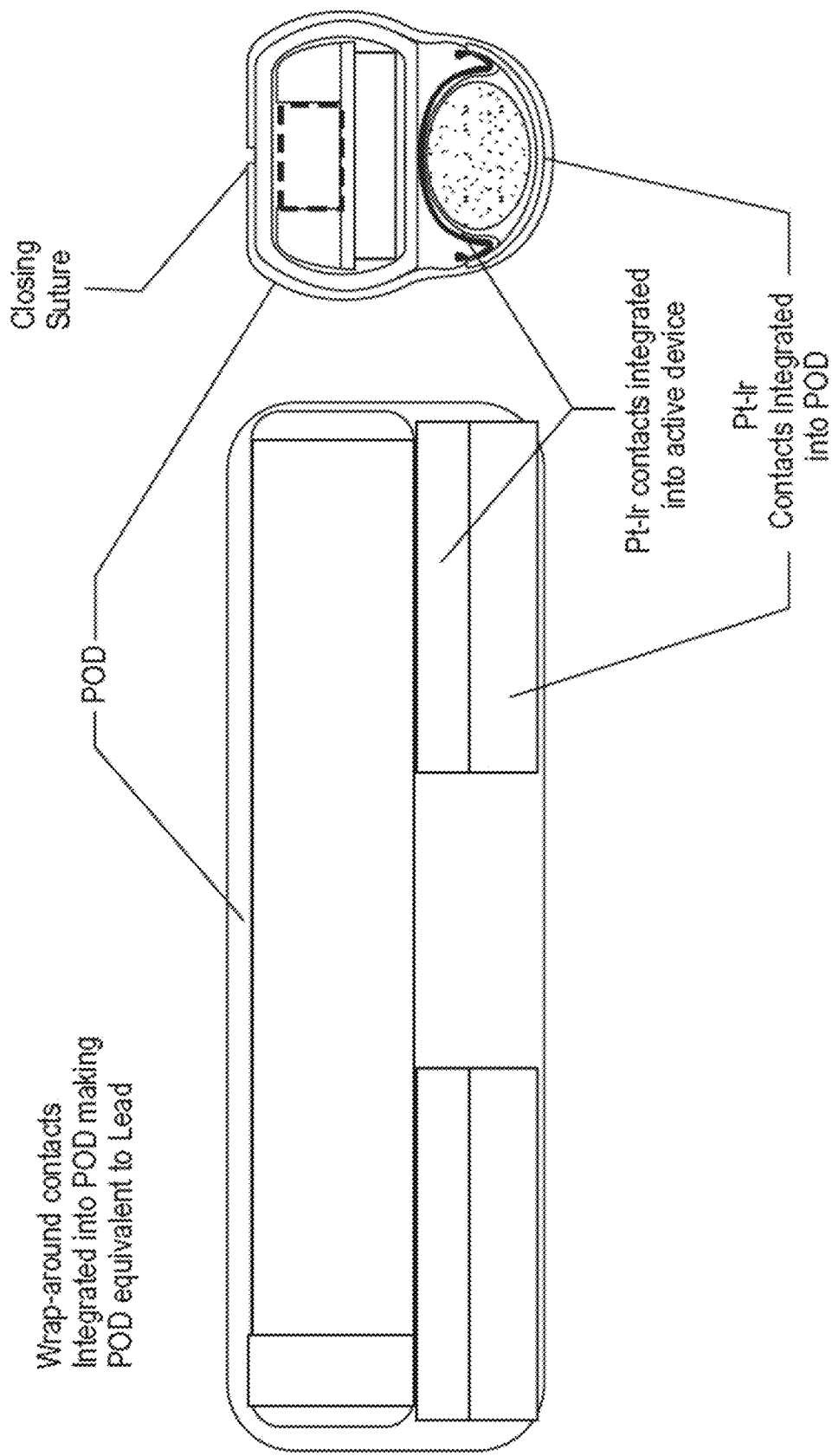
FIG. 4 shows a schematic diagram of a microstimulator and POD around vagus nerve.

As mentioned above, some of the device variations described herein may be used with a POD to secure the implant (e.g., the leadless/wireless microstimulator implant) in position within the cervical region of the vagus nerve so that the device may be programmed and recharged by the charger/programmer (e.g., "energizer"). For example, FIG. 4 shows a schematic diagram of a POD containing a microstimulator. The cross section in FIG. 4 shows the ceramic tube containing electronic assembly that includes the hybrid, battery and coil. The rigid or semi-rigid contacts are mounted on the tube and surround the oval vagus nerve. The POD surrounds the entire device and includes a metal conductor that makes electrical contact with the microstimulator contacts and electrically surrounds the nerve.

FIG. 3A is a perspective drawing of the Pod containing the microstimulator. Sutures (not shown) are intended to be bridged across one to three sets of holes. Electrodes integrated into the pod are not shown but would extend as bands originating and ending on the two outer pairs of suture holes.

In many variations, the microstimulators described herein are tunable electrical nerve stimulators configured to deliver modulated electrical stimulus to the vagus nerve of the patient for treatment of inflammatory and autoimmune disorders. The micro stimulator, in conjunction with the POD, is intended to perform as a chronic stimulating unit that generates output pulses with defined electrical characteristics to the vagus nerve of a patient. The stimulator is intended for chronic use and may be capable of executing patient specific programs with varying parameters in order to treat a wide array of diseases with differing severity levels.

Figure 3D:
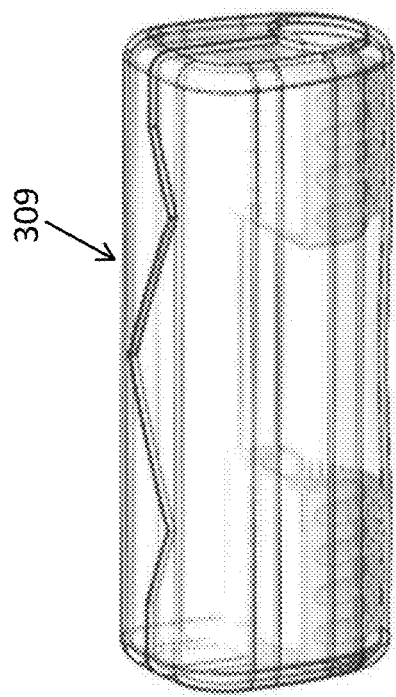
FIG. 3D shows the microstimulator of FIG. 3C within a POD.
Figure 3C:
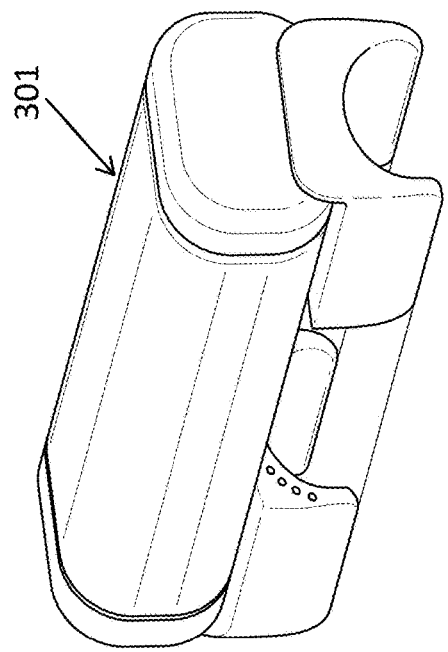
FIG. 3C shows another variation of a microstimulator.
Figure 3E:
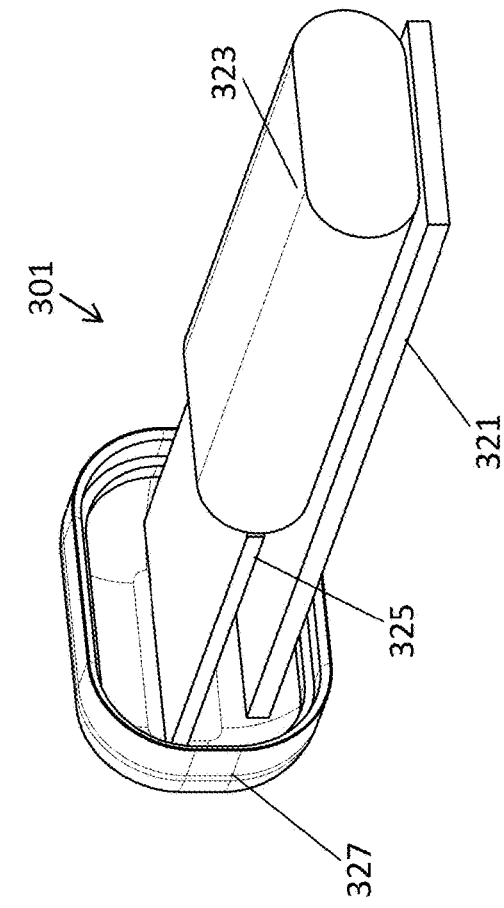
FIG. 3E shows another variation of the microstimulator.

In some variations, including those described above, the microstimulator consists of a ceramic body with hermetically sealed titanium-niobium ends and integral platinum-iridium electrodes attached. The microstimulator may be designed to fit within a POD 309, as shown in FIGS. 3A and 3D. As described above, the POD is a biocompatible polymer with integrated electrodes that may help the microstimulator to function as a leadless cuff electrode. In some variations, such as the variation shown in FIG. 3E, contained within the hermetic space of the microstimulator 301 is an electronic assembly that contains a rechargeable battery 321, solenoid antenna 323, hybrid circuit 325 and electrode contacts (Ti Alloy braze ring and end cap) 327 at each end to make contact with the titanium/platinum case ends.

In general, the microstimulator is designed to be implanted within deep tissue, so that it can be recharged and controlled using an external (e.g., transcutaneous) inductive link through a charger encircling the implant outside the body. One advantage to the micro stimulators configured as described herein (including the extremely low duty-cycle of the device) is the low energy requirements of these devices, particularly as compared to prior art devices. For example, Table 6, below illustrates exemplary charging and use profiles for low, typical and maximally used implants. In general, the daily charging duration for low and average patients may be less than 2 minutes/day, and for Maximum patients less than 10 minutes per day.

TABLE 6

Use and charge profiles

| Patient | Full Discharge | Charge Frequency | | |
| --- | --- | --- | --- | --- |
| | | Daily | Weekly | Monthly |
| Low | 53 days | 0.4 min | 2.6 min | 11.3 min |
| Typical | 50 days | 0.4 min | 2.8 min | 12.0 min |
| Maximum | 5 days | 3.7 min | NA | NA |

The electrode of the microstimulator may provide a nerve contact area equal to approximately ½ the surface area of the nerve for at least a length of 5 mm. Minimum electrode area=2 mm (min vagus diameter)×π×5 mm (min length)×½ circumference=15 mm2. For example, a vagus nerve diameter of 2-4 mm may be supported. In combination with the POD, less than 1 mm of total gap may be allowed around the vagus, indicating three sizes or adjustable electrodes. The bipolar Impedances of the electrodes may be less than 1000 ohms (real component).

In some variations (such as the variation illustrated above in FIG. 3E), the microstimulator may be implemented on a multi-chip hybrid substrate and consist of the following components: Microcontroller, Application Specific Integrated Circuit (ASIC), LiPON Rechargeable Battery, and various discrete components The Patient Charger communicates with and replenishes the microstimulator deep within the body (e.g., neck) utilizing an electromagnetic field. The Patient Charger may be used by both clinicians and patients. It may include a coil that is run through a handle that separates to expand for placement over then head. Once placed over the head and closed the Patient Charger may attempt to find the Microstimulator and start charging. When charging is complete the patient may be signaled. In use, a clinician may program the microstimulator by connecting a USB cable between the Prescription Pad and the Patient Charger. The Patient Charger wirelessly connect with the implant and with outer devices (e.g., the controller such as a prescription pad). The Patient Charger may also record all charging sessions and store Microstimulator data.

The chargers described herein are configured and optimized for use with the cervical, low duty-cycle microstimulators described above, or for sub-diaphragmatic use. These charges may be worn about a subject's neck and/or waist (or torso) and may very quickly charge the implanted micro stimulator, and may program and control the microstimulator as well as receive data or information from the microstimulator. The chargers described herein may use a solenoid that connects around the subject's neck with novel connection mechanism. For example, the connection mechanism may be clasp or quick connect connector that connects the loop (coil) of the charger around the subject's neck. The quick connector may be magnetic or friction fit. For example, in some variations the connector closing the loop around the subject's neck includes insertion of pins to connect one side of the loop(s) with the opposite side. For example, in some variations, the charger (e.g., energizer) coil uses a breakable coil with a magnetic latch and pogo spring pins to make contact. The coil resistance may be kept low despite the clasp/connection. For example, a multiplicity of pins may be used to keep coil resistance low and Q high.

The magnetic field strength of the charger may be modulated via a digitally compensated pwm circuit so that the power is critically tuned rather than using a resistive element. In addition, the carrier frequency may be generated using a phase accumulator to provide highly accurate frequency generation for precise tuning.

The Patient Charger may be stored in a Charging Dock to keep the battery in a charged state. A travel wall socket adapter may also be used. The Charger typically includes a battery, such as a LION rechargeable battery.

In operation, the Patient Charger may develop an axial magnetic field in alignment with the Microstimulator in the neck. The loop is sized to accommodate the largest neck and provide sufficient power to charge the battery in the adjustments to assure that sufficient charge is being transferred to Micro stimulator.

Recharge time for the Microstimulator may be dependent on how much energy is drained between recharges by the patient. This may depend upon the patient settings and how often the patient charges. Patients may be able to charge as infrequently as every month. This may allow the clinician to recommend a charging schedule that is most convenient for the patient; such as when a care giver is available. The neck loop makes charging a hands free operation once the device is put around the neck.

The Energizer and Microstimulator coils may be tuned to resonate so that energy is transferred with the maximum efficiency from the Energizer to Microstimulator. The Microstimulator in turn may harvest the energy from the Energizer created magnetic field to power itself. The power harvested may be less than 15 mW. Tuning, or maximizing the mutual inductance between the two coils may be performed by using resonators that are physically adjusted to approximately 133 KHz±4 KHz. Fine tune adjustments may be made dynamically by varying the Energizer frequency with the allocated 127-135 KHz frequency band. Another method to be employed for electronic tuning that may be used induces a static flux in series inductor in the Energizer coil to electronically modify the inductance (see, e.g., U.S. Pat. No. 3,631,534).

Energy transfer may be controlled by throttling the magnetic field. The magnetic field may be created by a high efficiency Class-D amplifier. The induced coil voltage on the resonator is controlled by the collector voltage driving the amplifier. It is important to only provide sufficient power to the implant as not to saturate the Microstimulator circuits or overheat the Microstimulator, a condition which can easily be achieved. Energy transfer varies significantly with vertical position so feedback is required. Feedback may be obtained by sending a query to the Microstimulator telemeter incoming energy level. This feedback may also be obtained by measuring the difference in Energizer coil voltage between the presence and absence of the Microstimulator, as described herein. With that measure the energy being absorbed by the Microstimulator can be calculated with sufficient accuracy to control the Energizer collector voltage.

The telemetry system in this example is implemented such that two standard microprocessor UARTs communication with a RS-232 type half duplex protocol where the Energizer is the master. Two rates, e.g., 1200 and 4800 baud, may be implemented. Forward telemetry modulates transmitter collector voltage to send data across. To keep the Microstimulator demodulator as simple as possible a DC balanced Manchester code may be employed with a simple zero crossing data slicer. The RS-232 code itself does not need to be DC balanced, but the presence of start and stop bits are sufficient to allow sufficient energy transfer during communications.

The Microstimulator resonated may be put into one of two states with a shorting switch. When the switch is open the Microstimulator is operating normally, receiving power and telemetry, and is loading the Energizer. When the Microstimulator switch is closed the coil is no longer tuned to the Energizer coil and the Microstimulator ceases to receive power, and the load that the Microstimulator normally asserts on the Energizer is removed. This switch provides several functions: it may be used to send back telemetry data to the Energizer, used by the Energizer to measure the power absorption by the Microstimulator, and/or used by the Microstimulator to turn off power absorption in case the Microstimulator becomes too hot or the internal voltage becomes too high.

The Microstimulator may respond to all packets by toggling the load switch with the UART. Data is sent in NRZ format (e.g., back telemetry). The Energizer may measure the coil voltage, removing the ≈130 KHz carrier and extracting the resulting data stream that is effectively the peak coil voltage updated at a rate of 20 KHz. The Energizer converts this analog voltage into a digital word and slices the data to produce bits that are fed to the UART. This is done in the digital domain because a sophisticated min/max peak detector can be implemented that does not require DC balanced data and can respond within 1-2 symbols.

Power is adjusted by achieving a target modulation depth on received back telemetry data. The target modulation depth is determined by calibrating the system through measurements of power transfer to the Micro stimulator. It is unknown at this point when calibration will occur: once for all systems, once for each system, on power up of each system, continuously as the Energizer coil moves around.

Static Magnetic Field Detector

Any of the implantable micro stimulators described herein can include a static magnetic field detector for emergency shut off of the micro stimulator. Though many safety measures have been taken, there might be unexpected situations such as circuit dysfunction or failure, sudden health condition change of the patient, unusual environment, thermistor failure, etc. A manual shut-off of the microstimulator may be needed in such emergency situations. In some variations, a magnet can be placed near the implantable microstimulator to trigger the static magnetic field detector and cause an emergency shutdown of the micro stimulator.

Figure 5:
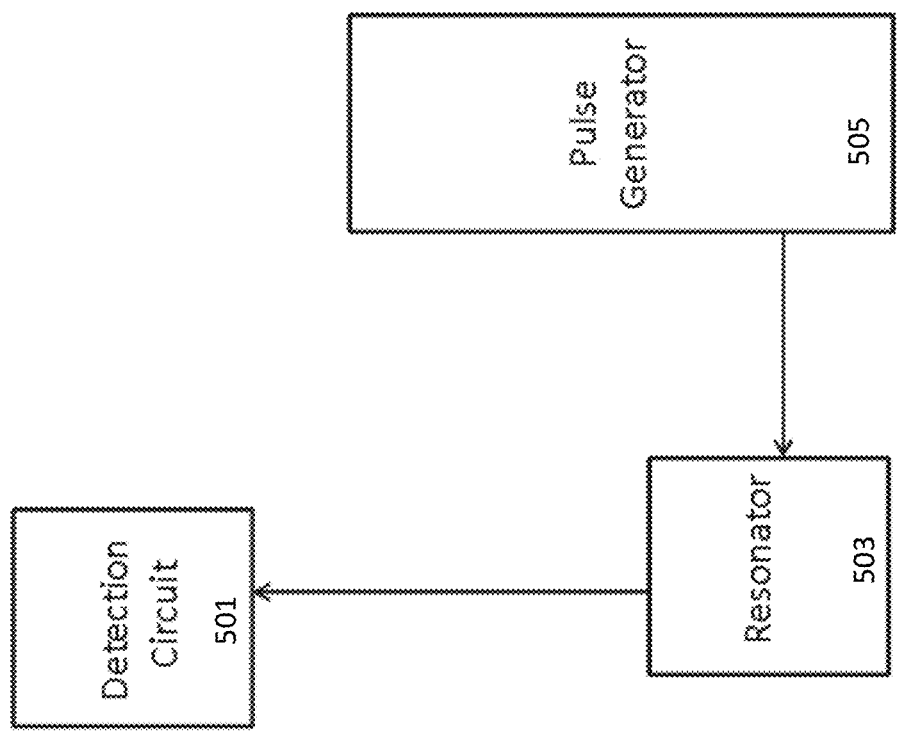
FIG. 5 is a block diagram of a static magnetic field detector for a neural micro stimulator.

FIG. 5 is a block diagram of the static magnetic field detector for emergency shut down the microstimulator. In some variations, the static magnetic field detector can comprise a resonator built in the microstimulator. As discussed above, the implantable microstimulator can comprise an antenna to receive power from the external electric field. In some variations, the antenna can comprise a coil of wire with a ferrite core to form an inductor with a defined inductance. This inductor can be coupled with a capacitor and a resistance to form a resonant circuit (RLC circuit). The RLC circuit can have certain characteristics such a resonant frequency and a quality factor (Q). An external high quality NPO capacitor can be used to set the tank frequency. The frequency can be set to that of the radiated electric field to receive power and data from the external source. For example, the resonator can be a coil and capacitor configured to resonate at about 131 KHz+/−2%. The coil can be constructed with many turns of magnet wire with a target inductance of about 20 uH. The resonator can be configured to resonate at other frequencies and the coil can be constructed with an inductance of other values. In some other variations, it is possible that the static magnetic field detector can comprise another resonator instead of using the receiving resonator.

The static magnetic field detector can comprise a low power pulse generator. For example, a low power current pulse generator can be connected with the RLC circuit. In some variations, the power of the pulse generator can be lower than 10 microwatts. For example, the pulse generator can be an ultra-low power pulse generator based on a ring oscillator with the power between 1 nanowatt and 10 microwatts. In some other variations, the power of the pulse generator can be between 1 nanowatt and 1 microwatt. In yet some other variations, the power of the pulse generator can be lower than 1 nanowatt.

As shown, the low power pulse from the pulse generator can be introduced into the coil or the resonator RLC circuit. As known to the skilled in the art, RLC circuit can resonate at a resonance frequency or a predetermined frequency range. The oscillating current pulses decay with time due to the resistance in the circuit. When the coil is tuned, the low power pulses can take a relatively long time to decay. But when a magnetic field is introduced to the coil, the inductance of the RLC circuit is changed and the coil is detuned. Therefore, the decay rate is much quicker (or time constant is smaller). For example, a magnet can be placed near the implantable micro stimulator, the ferrite of the coil can be coupled with the inductance of the static magnetic field of the magnet, the inductance of the RLC resonator can be changed to be off the resonance frequency or the predetermined frequency range. When the coil is detuned, the low power pulses take a much faster time to drop off to zero. The decay rate of the pulses can be much higher.

The static magnetic field detector can further comprise a detection circuit as shown in FIG. 5. The detection circuit 501 can be configured to monitor the decay rate of the pulses or time constant of the resonator 503. As known to the skilled in the art, the detection circuit can have many variations. For example, the detection circuit can measure a current in the resonator. For another example, the detection circuit can measure a voltage at the resonator circuit. The static magnetic field detector can be configured to shut down the microstimulator when the decay rate is increased to a predetermined value. In some variations, the static magnetic field detector can be configured to shut down the microstimulator when the decay rate is increased to 50% of the previous value. In some variations, the static magnetic field detector can be configured to shut down the microstimulator when the decay rate is increased to 50% of the previous value. In some variations, the static magnetic field detector can be configured to shut down the microstimulator when the decay rate is increased to 2 times of the previous value. The static magnetic field detector can be configured to shut down the microstimulator when the decay rate is 1.5, 2, 2.5, 3, 4, 5, 10 times of the previous value or any values therebetween. Values outside the above range are also possible.

The static magnetic field detector can be configured to shut down the microstimulator in a variety of ways. For example, the static magnetic field detector can be configured to shut down the microstimulator by using h a shorting switch. In some variations, when the switch is open, the microstimulator is operating normally; when the switch is closed, the resonator is open and the microstimulator turns off power. In some other variations, when the switch is closed, the microstimulator is operating normally; when the switch is open, the microstimulator turns off power.

In some variations, the low power pulses (e.g., from pulse generator 505) can be introduced periodically, such as every second, to detect the presence of the magnetic field. In some other variations, the low pulses can be introduced continuously to constantly monitoring the presence of the magnetic field.

Disclosed herein are also methods to shut down an implantable microstimulator by using a static magnetic field. In some variations, the method of shutting down an implantable microstimulator by the static magnetic field detector can comprise utilizing a built-in receiving coil of the micro stimulator. In some other variations, the method of shutting down an implantable microstimulator by the static magnetic field detector can comprise utilizing another RLC resonator of the micro stimulator.

Figure 6:
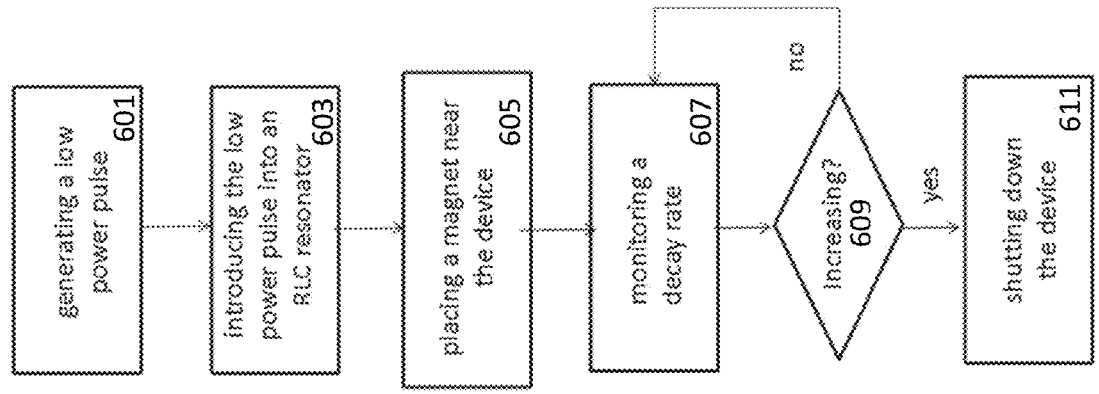
FIG. 6 is a flow diagram illustrating the operation of a static magnetic field detector to shut down a neural microstimulator in emergency.

FIG. 6 schematically illustrates the method of shutting down an implantable microstimulator by a static magnetic field detector. The method can comprise generating low power pulses 601. In some variations, the power of the pulse generator can be between 1 nanowatt and 10 microwatts. In some other variations, the power of the pulse generator can be between 1 nanowatt and 1 microwatt. In yet some other variations, the power of the pulse generator can be lower than 1 nanowatt. In some variations, the low power pulses can be introduced periodically. In some other variations, the low power pulses can be introduced continuously.

The method of shutting down an implantable microstimulator by a static magnetic field detector can further comprise introduce the pulses into the coil of the RLC resonator 603. For example, the pulses can be current pulses connected to the RLC resonator. The method can further comprise placing a magnet near the implantable microstimulator 605.

The method of shutting down an implantable microstimulator by a static magnetic field detector can further comprise monitoring the decay rate of the pulses of the resonator or the time constant of the RLC resonator 607, and determine if they are increasing or decreasing 609. When the coil is tuned, the low power pulses can take a relatively long time to decay. But when a magnetic field is introduced to the coil, the inductance of the RLC circuit is changed and the coil is detuned. Therefore, the decay rate can be much larger (or time constant can be smaller). The static magnetic field detector can be configured to shut down the microstimulator when the decay rate is at a predetermined value 611, for example, the decay rate is 1.5, 2, 2.5, 3, 4, 5, 10 times of the previous value or any values therebetween. Values outside the above range are also possible. Shutting down the device may immediately stop delivery of power to the nerve to which the implant is attached.

Any appropriate static magnetic field sensor may be used, although it may be particularly beneficial to avoid Hall effect devices. In addition to the use of a low-power pulse applied to the resonator and a detection circuit, as described above, in any of these apparatuses a Wiegand material may be used, or any other material that uses a magnetic hysteresis effect. The Wiegand effect is a nonlinear magnetic effect, and may include the use of a specially annealed and hardened wire ("Wiegand wire"), such as a low-carbon Vicalloy, a ferromagnetic alloy of cobalt, iron, and vanadium. The wire may exhibits a very large magnetic hysteresis: if a magnet is brought near the wire, the high coercivity outer shell excludes the magnetic field from the inner soft core until the magnetic threshold is reached, whereupon the entire wire—both the outer shell and inner core may rapidly switch magnetization polarity (the Wiegand effect). The voltage induced by a changing magnetic field may be proportional to the rate of change of the field, thus a Wiegand-wire core can increase the output voltage of a magnetic field sensor by several orders of magnitude as compared to a similar coil with a non-Wiegand core. This higher voltage can easily be detected electronically.

Power Control Loop

As mentioned above, in any of these apparatuses, in order to protect the patient from harm from overheating of the neurostimulator, the temperature of the outer surface of the implant can be kept within a minimum temperature range (e.g., <1.1° C., 1.3° C., 1.5° C., 1.7° C., 1.8° C., 1.9° C., 2° C., 2.1° C., 2.2° C., 2.3° C., 2.4° C., 2.5° C., etc.) of the normal surrounding body temperature. This temperature of operation is particularly critical when the implant is interacting with the charger, as described above. As will be outlined herein, the temperature of the microstimulator may be regulated within a predetermined temperature range (e.g., within about 2 degrees Celsius) by controlling the power drawn by the microstimulator from the charger.

Although the temperature may be estimated by one or more thermistor within the implant that may be used to estimate temperature, and may detune the microstimulator coil when the internal temperature reaches a threshold (internal threshold, e.g., approximately 41.5° C.), the critical temperature may be the external temperature, rather than the internal temperature. Although it may be difficult to measure the outside temperature, accurate estimation of this temperature may allow more precise and longer-lasting control of the implant, including during charging and/or telemetry, as well as enhancing safety.

Figure 7:
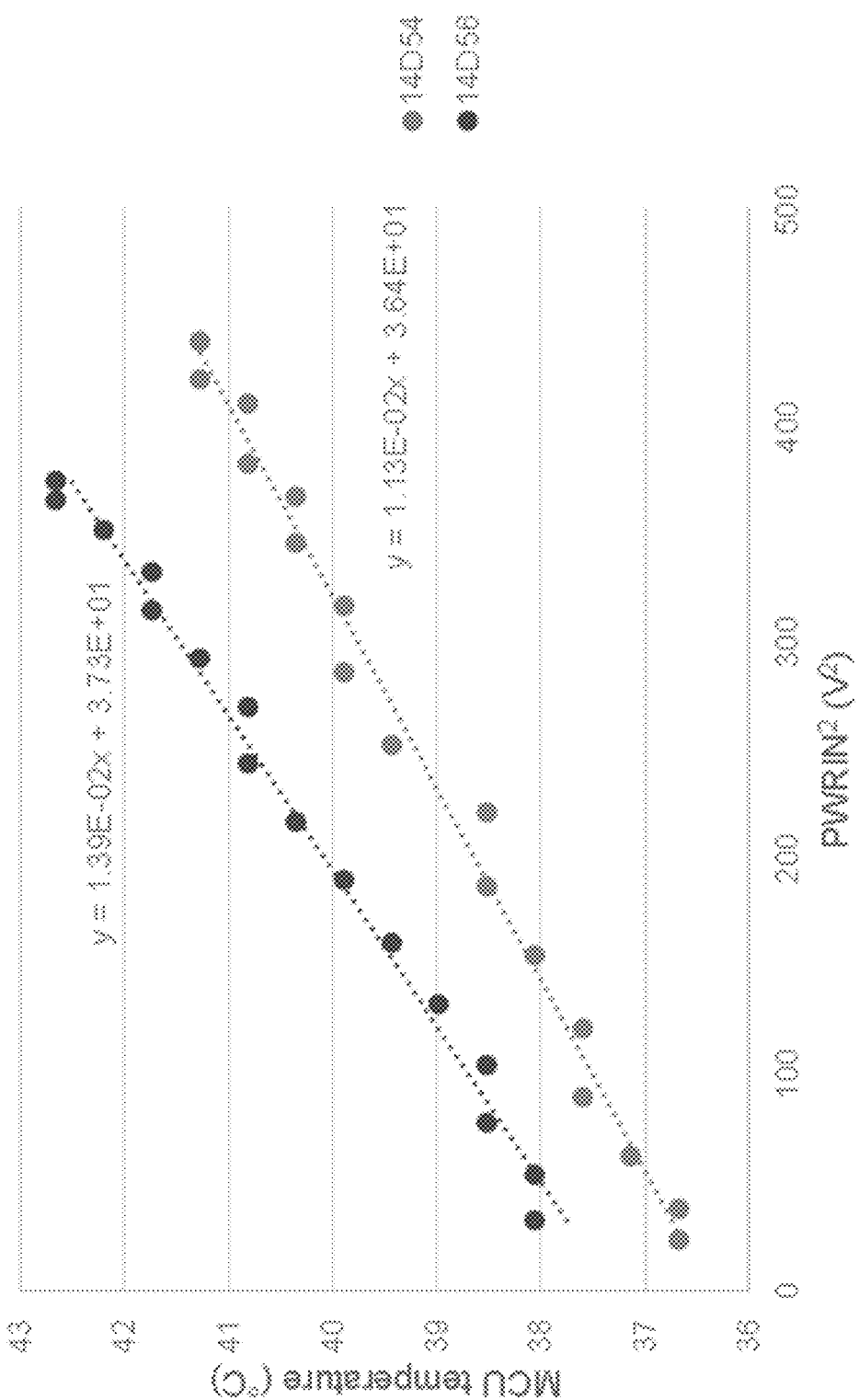
FIG. 7 is a graph showing that the microcontroller temperature of the microstimulator may be proportional to the square of the microstimulator tank voltage (PWRIN); data is from two different animals having an MS implanted at the carotid.
Figure 8:
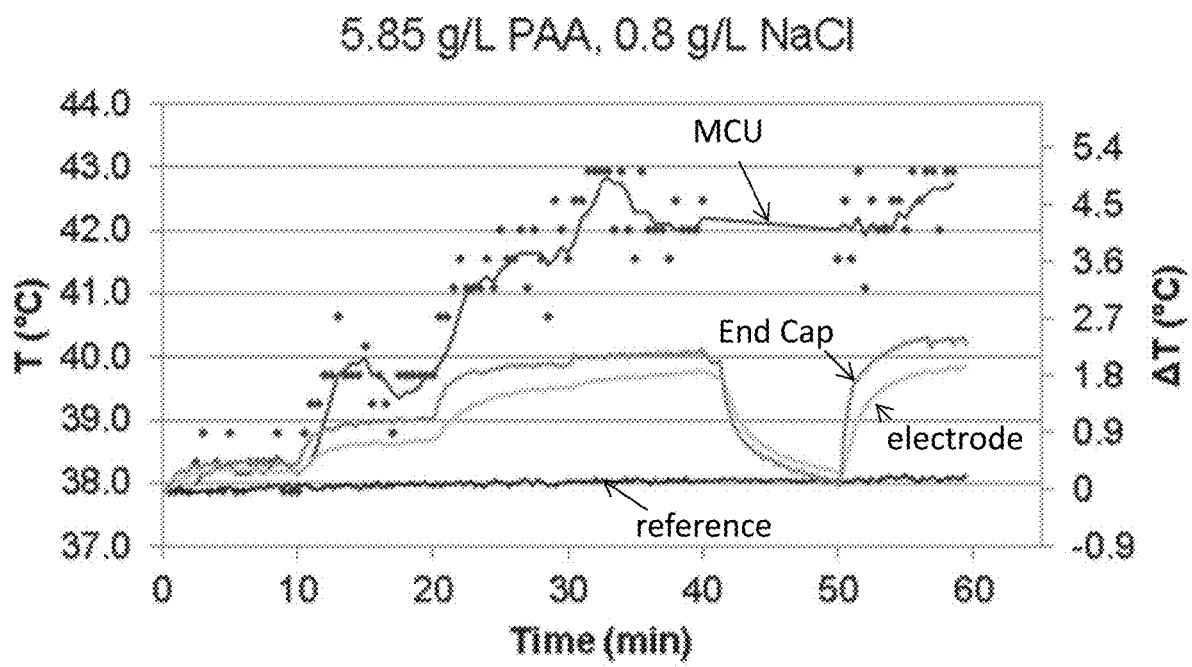
FIG. 8 is a graph illustrating (based on thermal modeling) that surface temperatures of a microstimulator (MCU) may change as a function of power in (PWRIN); in this example, a 1.75 degrees Celsius temperature increase of the end caps occurs for a PWRIN of about 16V in some apparatuses.
Figure 9:
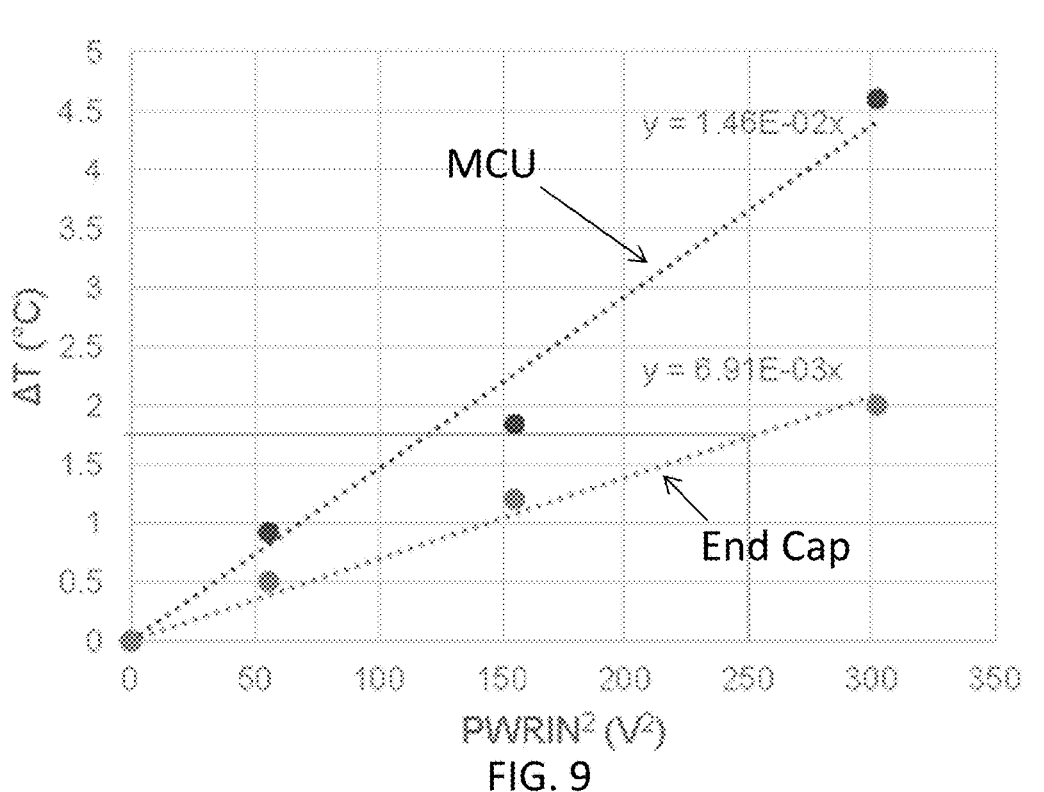
FIG. 9 shows a linear relationship between the change in both microcontroller temperature (MCU) and end cap temperature as the square of PWRIN (PWRIN$^2$).

FIG. 7 shows that the microcontroller temperature of the micro stimulator is proportional to the square of the micro stimulator tank voltage (PWRIN). Two animal subjects were implanted with a MS and the temperature of each implant was determined, and shown to be a function of power in (PWRIN) for each. This is also shown in the graph of FIG. 8. Since the microcontroller is part of the micro stimulator, the temperature of the outer surface can be estimated using a heat transfer equation, as shown in FIG. 8, which also shows the temperatures of the microcontroller and the end caps as a function of PWRIN squared. The graph in FIG. 9 shows that a 1.75 degrees Celsius temperature increase of the end caps occurs for a PWRIN of about 16V. At steady state, the rise in temperature a point i (delta $T_i$) is related to the net heat flux, q, by the heat transfer equation:

$$q = C_i \Delta T_i,$$

Where Ci is a lumped heat loss coefficient that characterizes the heat flux path through point i into the surrounding medium. Thus, in vitro measurements show that accurate estimates of surface temperature can be determine for given power levels. If the power in (PWRIN) can be regulated (e.g., below a threshold level) then the maximum surface temperature may be regulated to <2° C. different relative to body temperature (+/−2° C.).

In operation, the PWRIN can be determined by directly querying the micro stimulator (also referred to herein as the microregulator or MR). For example, the charger can query the micro stimulator during charging for the PWRIN, and can adjust the power level of the charger to ensure that PWRIN remains below the desired threshold (e.g., 16V or another predetermined voltage level). However, querying the micro stimulator may require a communication link between the MR and the charger and software to process and handle this information. It would be desirable if the PWRIN, the tank voltage of the MR, could be determined by values that can be measured entirely on the charger.

FIGS. 11-15 show an inductive circuit analysis of the charger and the MR. From this analysis, it was determined that PWRIN was correlated to the set power level of the charger (TxH) multiplied by the change in voltage across the energizer coil circuit when unloaded by the MR and when the energizer coil circuit is loaded by the MR (RxU-RxL), where RxU is the voltage across the energizer coil circuit when unloaded by the MR (can short the MR coil to create the unloaded state), and RxL is the voltage across the energizer coil circuit when loaded by the MR. This correlation holds well for any value of k, the coupling coefficient, between the charger and MR, meaning the correlation holds regardless of MR location and orientation. Thus, TxH* (RxU−RxL) can be used as part of a power control loop parameter that allows the charger to control PWRIN, and thus the increase in temperature, by monitoring only the charger parameters.

Figure 10A:
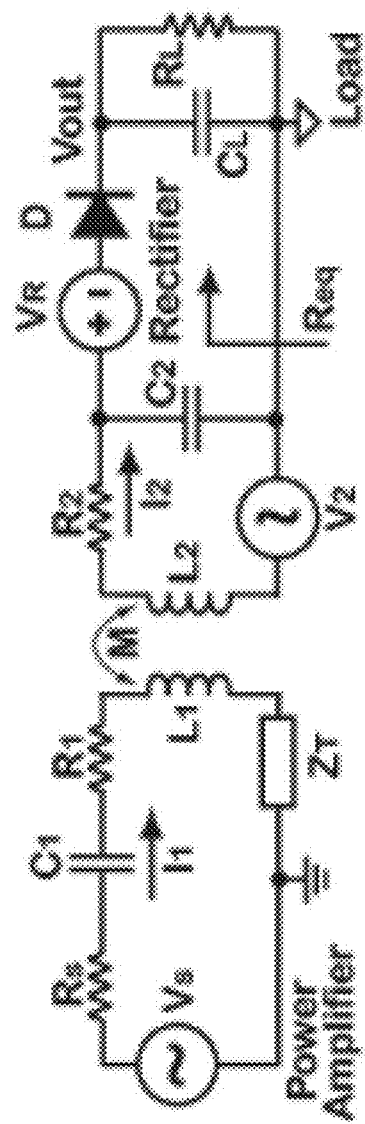
FIGS. 10A and 10B are generic circuit descriptions of a power amplifier and an implant that receives inductive charging from the power amplifier, and a simplified circuit diagram, adapted from Ghovanloo and Atluri ("An Integrated Full-Wave CMOS Rectifier With Built-In Back Telemetry for RFID and Implantable Biomedical Applications," Circuits and Systems I: Regular Papers, IEEE Transactions on, vol. 55, no. 10, pp. 3328-3334, November 2008). These diagrams may be helpful in describing a possible, theoretical description of the estimation of temperature in an implant from a charging device (e.g., inductive link circuit analysis), as described herein.
Figure 10B:
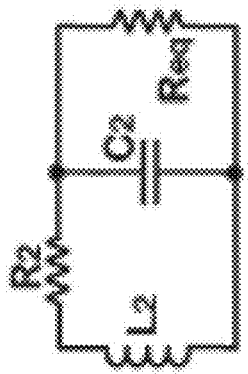

For example, FIGS. 10A-10B show an exemplary inductive charging circuit. Circuits are coupled through mutual inductance, M, where:

$$M = k\sqrt{L_1 L_2},$$

k is the coupling coefficient. Rectifier circuit is represented as an ideal diode in this example (FIG. 10A) in series with a DC voltage source equal to the rectifier dropout voltage. It has a nonlinear impedance given by:

$$R_{eq} = \frac{1}{2} R_L \left( \frac{v_2}{v_2 - v_R} \right)^2,$$

Where $R_L$ is the load resistance and $$V_2 = k Q_2 \sqrt{L_1 L_2} j\omega i_1$$

It may be shown that the reflected impedance, $Z_T$ is given by:

$$Z_T = \frac{\omega^2 k^2 L_1 L_2}{R_2 + j\omega L_2 + \frac{R_{eq}}{1 + j\omega R_{eq}}}.$$

Figure 11:
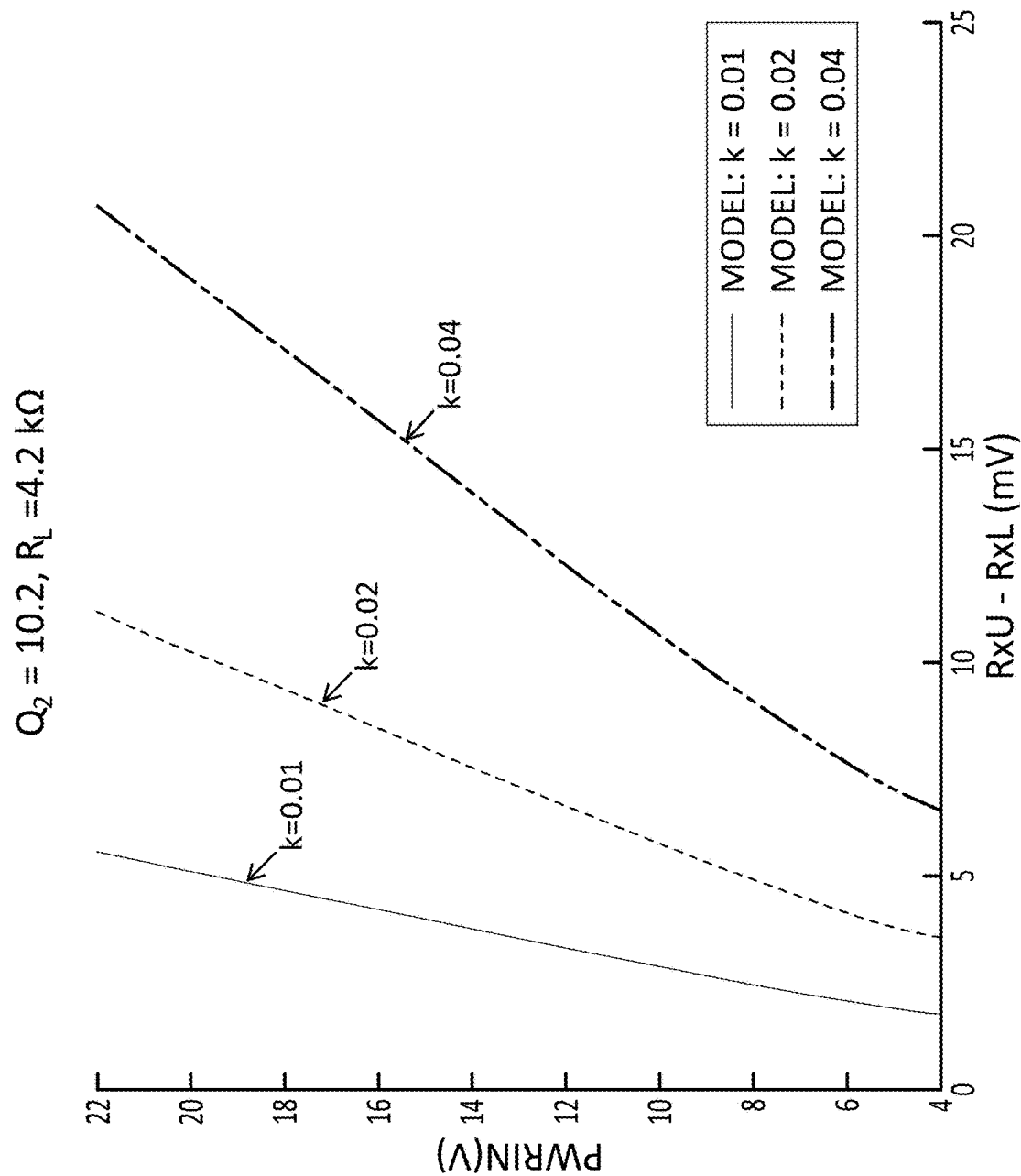
FIG. 11 is a graph illustrating the relationship between power in vs. margin for different coupling coefficients between the charger and the implant inductive coils.
Figure 12A:
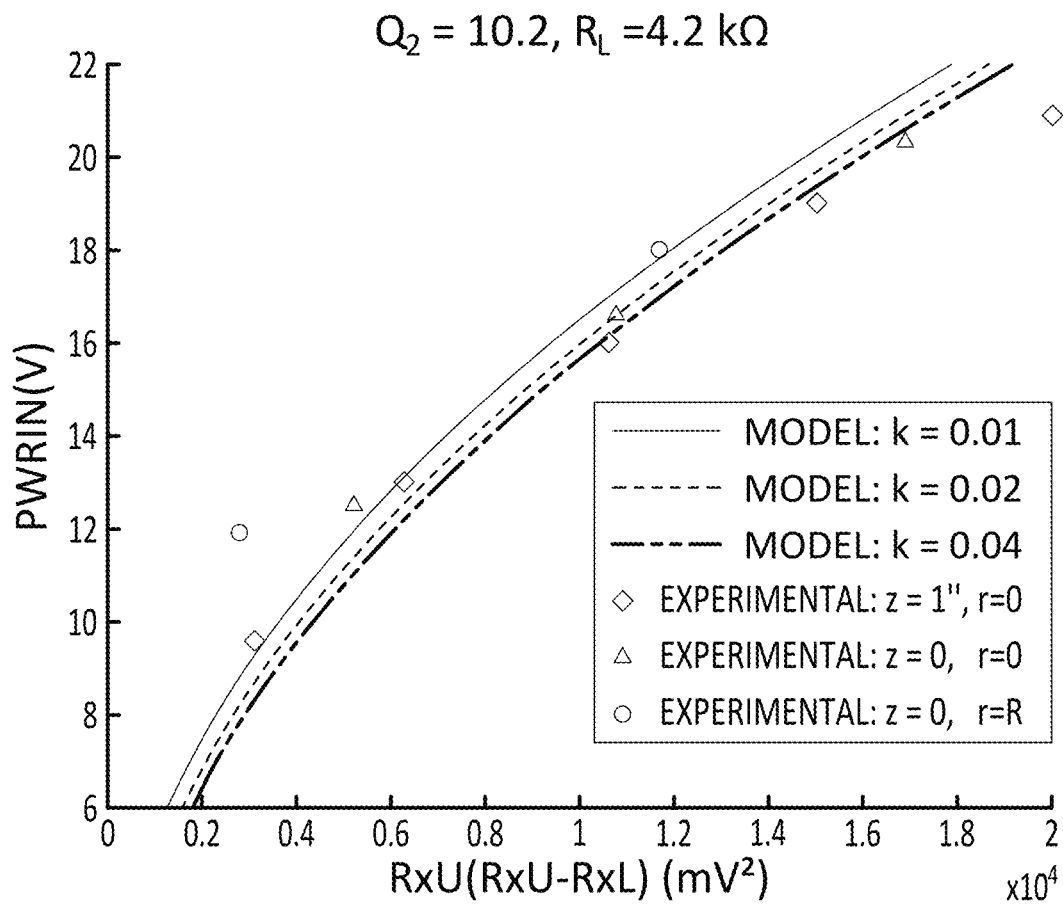
FIG. 12A shows a first example of scaling (in a model) charger parameters to estimate temperature and/or power in (PWRIN) in an implant.
Figure 12B:
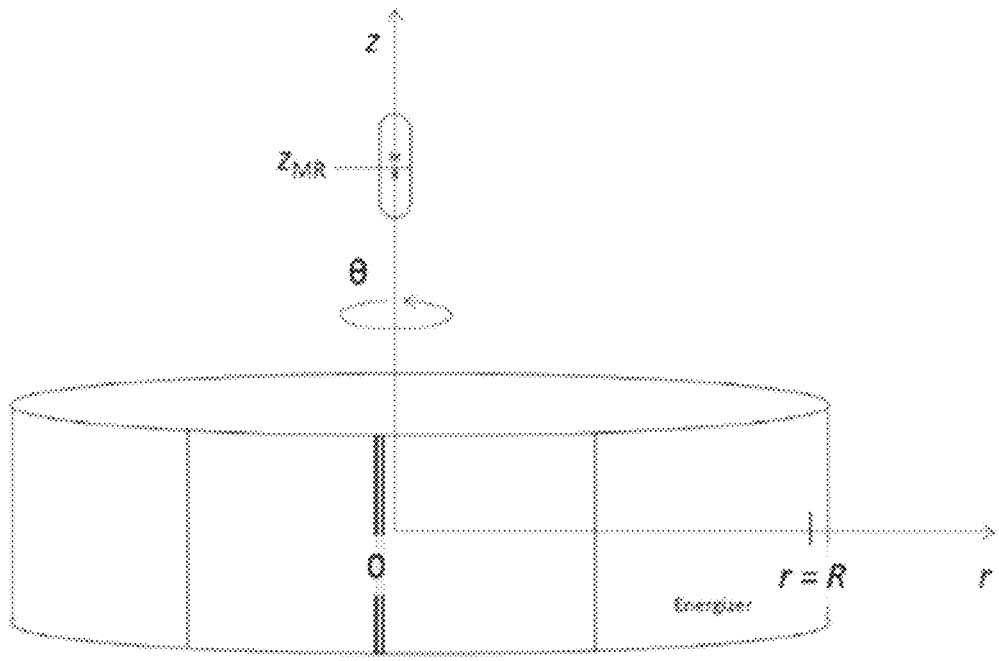
FIG. 12B is a model that shows the position of the implant relative to the charger.
Figure 13:
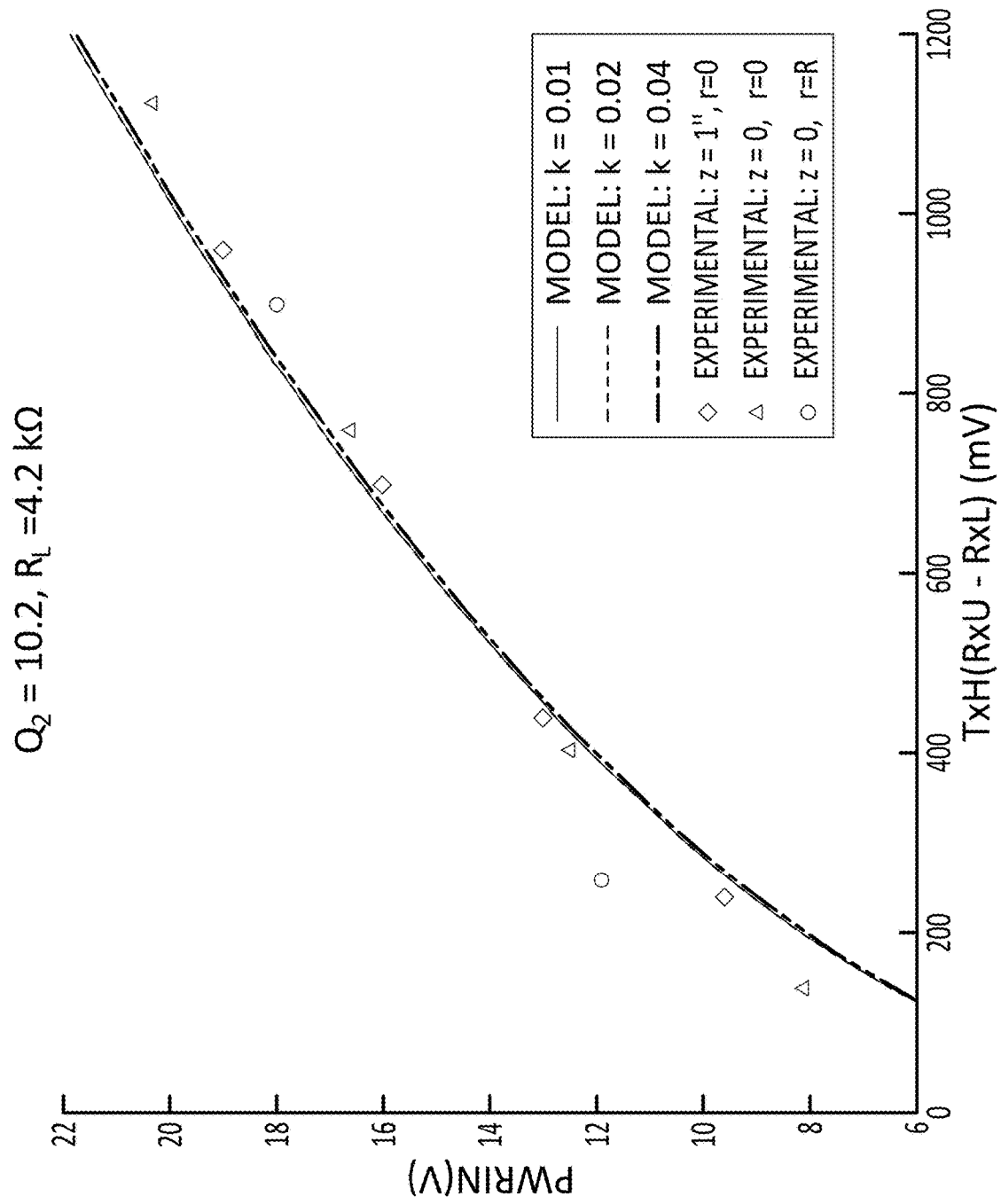
FIG. 13 is another example of an estimation of charger parameters illustrating estimate of power in to the microcontroller may be estimated regardless of coupling coefficient, when RxU−RxL is multiplied by TxH (to give the same curve for any value of k, as TxH is a linear function of V2 where V2=0 when TxH=0).
Figure 14:
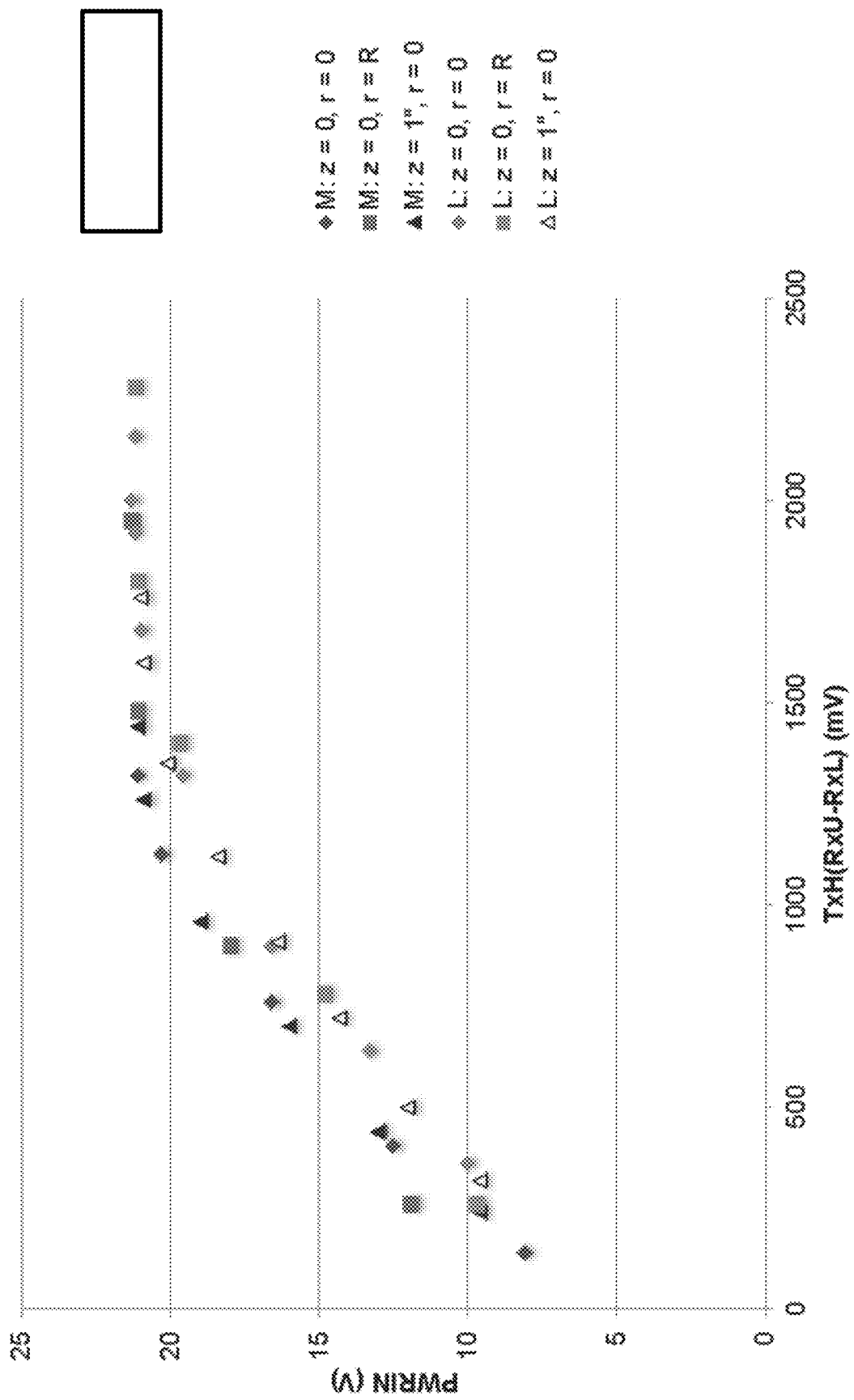
FIG. 14 illustrates a proposed loop parameter, in which each charger size may have a unique target value for TxH(RxU−RxL), from which an estimate of PWRIN may be made.

Then:

$$|V_1| = |i_1(R_1 + j\omega L_1 + Z_T)|,$$

or $$|V_1| = |V_{1 unloaded}| + |V_T|,$$

where $V_{1 unloaded}$ corresponds to RxU and $V_T$ to RxU−Rxl. Plotting V2=PWRN vs. margin (RxU-RxL) gives a different curve for each value of k, as shown in FIG. 11. However, it is possible to find a relationship between $V_2$ and $V_1$ that is independent of k. For example, multiplying RxU by RxU-RxL may bring the coupling curves within close alignment, as show in FIGS. 12A-12B. These curves do not match perfectly because RxU has an offset with respect to $V_2$ (e.g., there is a threshold $V_2$ for RxU=0). Alternatively, multiplying TxH by RxU−RxL may give the same curve for any value of k since TxH is a linear function of V2, where V2=0, when TxH=0, as shown in FIG. 13. The TxH value does not need to be measured, as it is being generated. Thus, using a given target value for TxH(RxU-RxL), it may be possible to determine the power in (PWRIN) within at least +/−1 V, regardless of the coupling between the implant and the charger (in the charger). Although each size of charger (e.g., coil) may have a unique target value for TxH(RxU−RxL), multiplying TxH in this manner (instead, for example, or RxU) may reduce the difference between value for different sizes, as shown in FIG. 14. Thus, the charger does not require that the communication link between the implant and the charger to query the MS for PWRIN. In any of these examples, however, the link may be active (or at least the MS may be switching and RxU−RxL may be above a detection threshold). If RxU−RxL is not detected, the implant may be configured to keep the temperature within the desired range (e.g., +/−2° C.) by duty cycling.

Figure 15A:
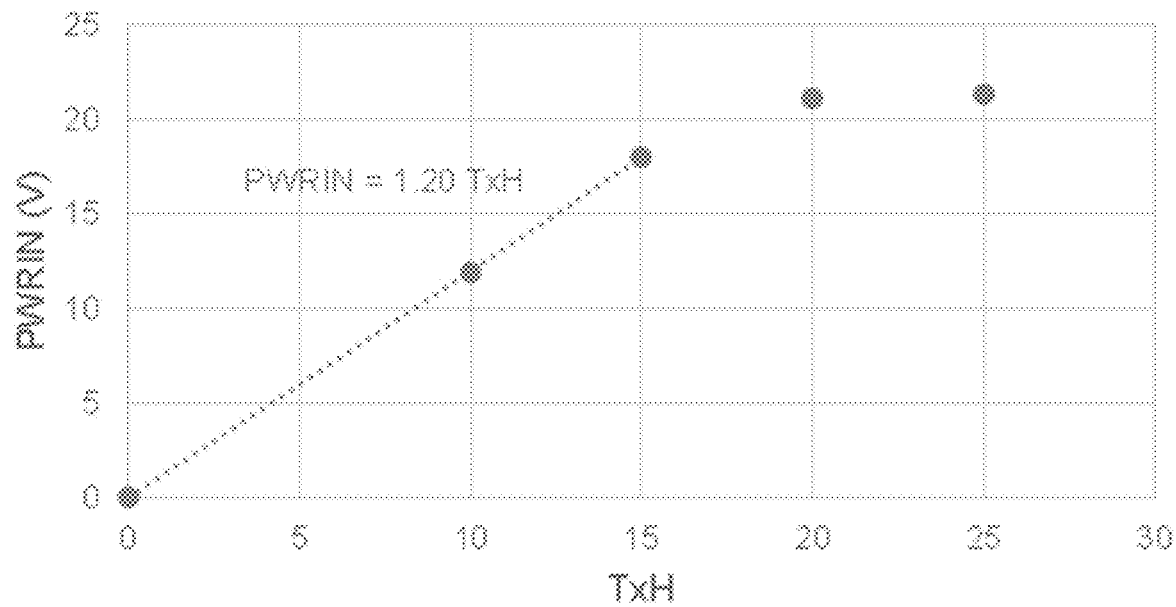
FIG. 15A shows the relationship between PWRIN and TxH for worse-case placement of an implantable micro stimulator.
Figure 15B:
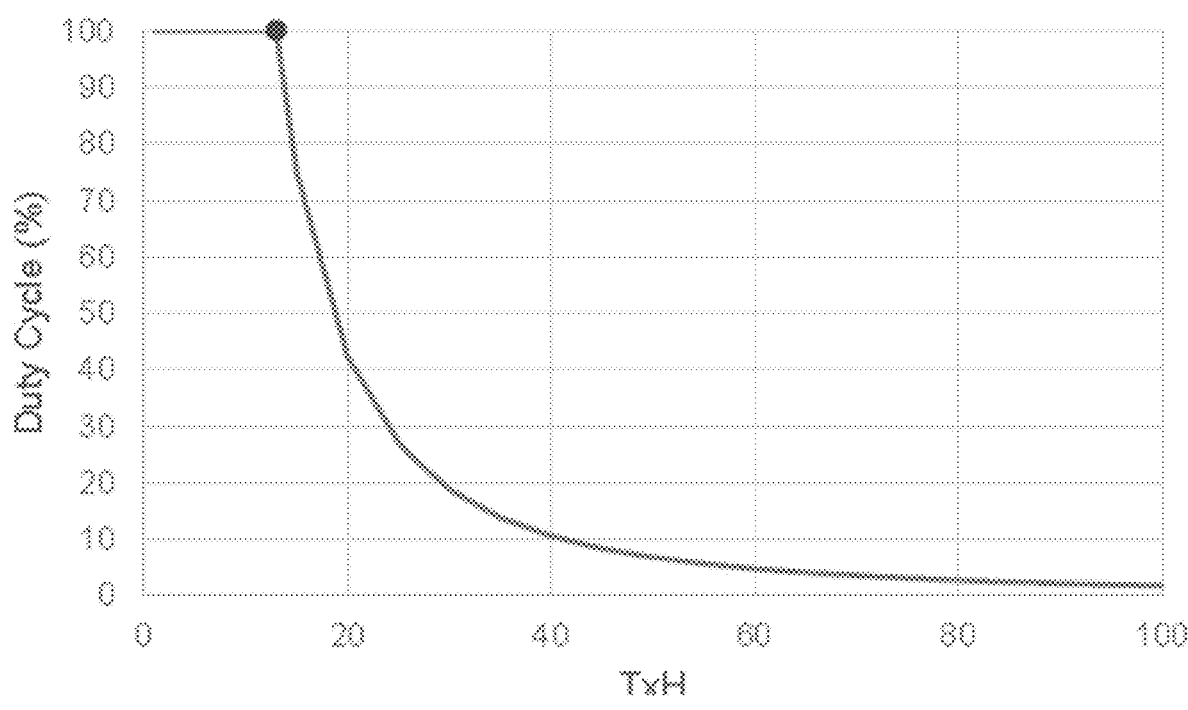
FIG. 15B is a graph illustrating modulating duty cycling the MS based on communication between the implant and the charger to prevent overheating of the implant.

Even for worst-case placement of the micro stimulator, the apparatus may determine the value of $TxH_{max}$ that gives a target PWRIN (e.g., 16V in the examples above) to keep the temperature within a desired range. For example, for any value of TxH above $TxH_{max}$, the implant may use duty cycling to keep the average power constant, as shown in FIGS. 15A-15B. In this example, a duty cycle period may be picked such that, for $D_{min}$ (e.g., 2% duty cycle) may be chosen such that ton is sufficient to establish a communication link between the implant and the charger.

For example:

$$D = \begin{cases} 100\%, & \text{if } T \times H \leq T \times H_{max} \\ \left(\frac{T \times H_{max}}{T \times H}\right)^2 \times 100\%, & \text{if } T \times H > T \times H_{max} \end{cases}$$

Figure 16:
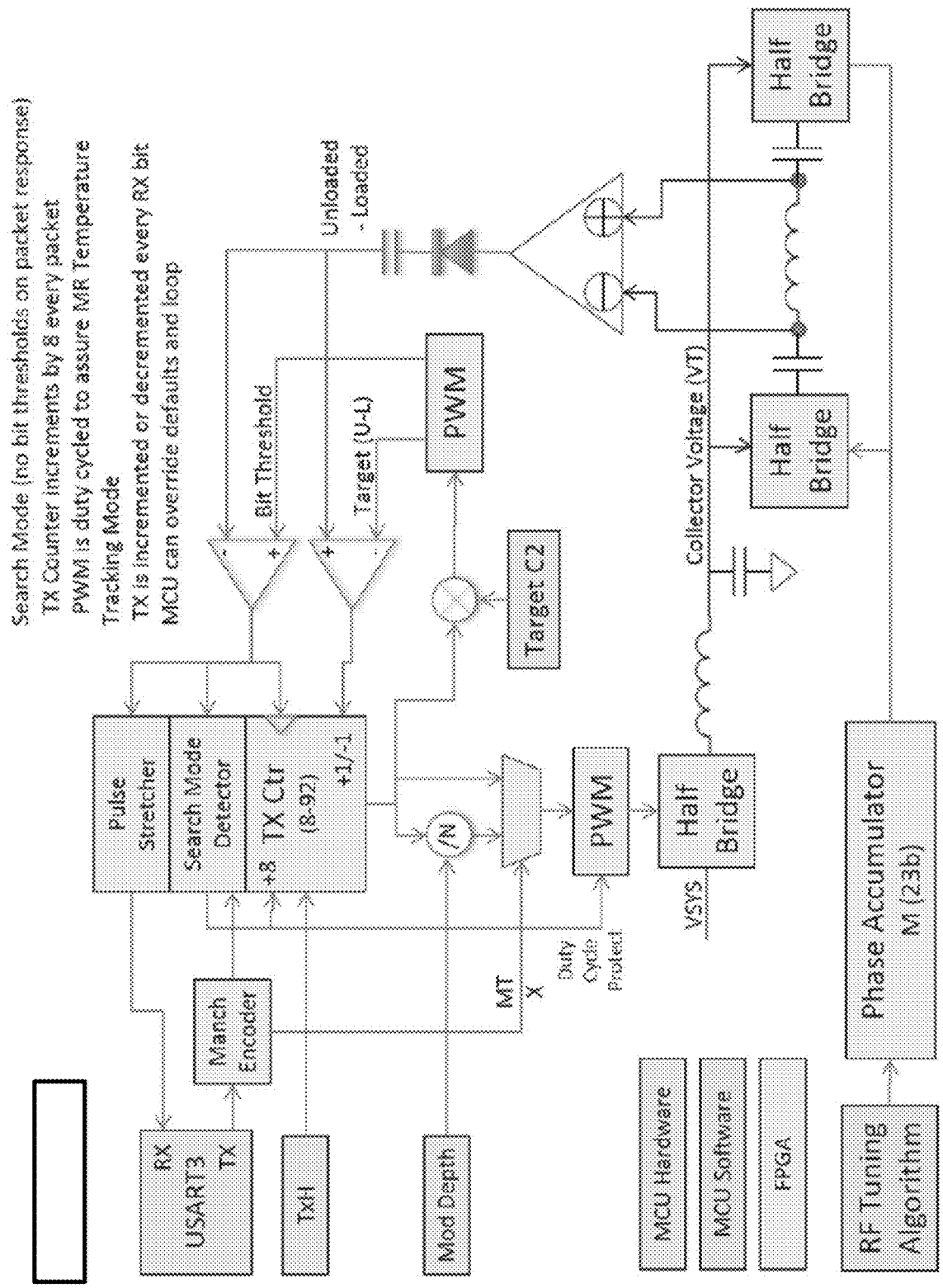
FIG. 16 is a schematic of a controller (including a power control loop) of a micro stimulator.

FIG. 16 illustrates schematically duty cycling in the absence of communication between the implant and the charger.

Based on this, the apparatus may determine, for a particular combination of implant and charger, a PWRIN that keeps the $T_{max}$ of the surface of the implant within a predetermined limit (e.g., +/−2° C.). In general, MR temperature is proportional to the square of PWRIN. PWRIN may be estimated based only on measurements of energizer coil voltage, and an energizer power control loop may be based on the parameter TxH(RxU−RxL) to maintain a relatively constant value of PWRIN regardless of implant location. When the implant (microstimulator) load modulation is not detected by the charger, duty-cycling may keep the $T_{max}$ within limit assuming the worst-case position of the micro stimulator. The power control loop may be entirely hardware based, or can include firmware or software.

Thus, a target value for the power control parameter can be determined based on the type of charger, the type of implant, and the type of coupling between the two. The target values can be determined based on in vitro experiments, or can be determined in vivo during a calibration procedure. The above method of controlling the outer temperature of the MR works well except when the MR load modulation (RxU−RxL) is not detected. In this situation, the MR can be duty cycled to keep the temperature within limits, assuming the worst-case placement for MR placement, as shown in FIGS. 15A and 16. For example, a maximum value of TxH can be determined for the worst case placement that results in the target PWRIN (e.g. 16 V). When TxH of the charger is below the maximum TxH, then the charger is operated at 100% duty cycle. However, when the TxH is greater than the maximum TxH, then the charger can be operated at less than 100% duty cycle, such as according to the equation $(TxH_{max}/TxH)^2 \times 100\%$.

As mentioned, a power negotiation protocol can be used by the charger and MR to determine what power level (e.g. TxH) or charge rate should be used to charge the MR. At the start of the protocol, the charging may be turned off or throttled and the communications between the charger and MR can be turned on. The initial communications can be used to exchange information regarding the type of charger (charger capabilities), the type of battery (implant capabilities), and the coupling used between the two devices, which can all be used to determine the appropriate charge rate or power level.

When the MS draws too much power, communications may collapse. Therefore, the power drawn by the MS can be throttled to restore communications. For example, in some embodiments, as the battery (e.g., a Quallion lithium-ion battery) charge is depleted, the charging current drawn from the RF tank circuit increases. This can cause antenna voltage of the implant to drop below the regulator drop out voltage in situations where insufficient RF power is available (e.g., when the implant is far from the external charger or separated from the charger by greater than a predetermined distance), which can cause communications to drop out.

In some embodiments, to mitigate this problem and prevent the antenna voltage from dropping below the regulator drop out voltage, the implant can use an adjustable current limit that restricts the amount of current drawn by the implant to perform functions outside of communication, such as charging the battery. When the implant initiates RF contact with the charger, the current limit of the implant is set to a predetermined minimum level, which presents a maximum load impedance to the RF tank circuit. If the antenna voltage of the implant is above a predetermined limit, the current limit of the implant may be increased to the next level by a predetermined amount. The process may be repeated until either the predetermined maximum current limit is reached, or the antenna voltage of the implant falls below the predetermined limit. If the antenna voltage of the implant falls below the predetermined limit, the current limit of the implant can be set at the previous level by decreasing the current limit by a predetermined amount.

Figure 17:
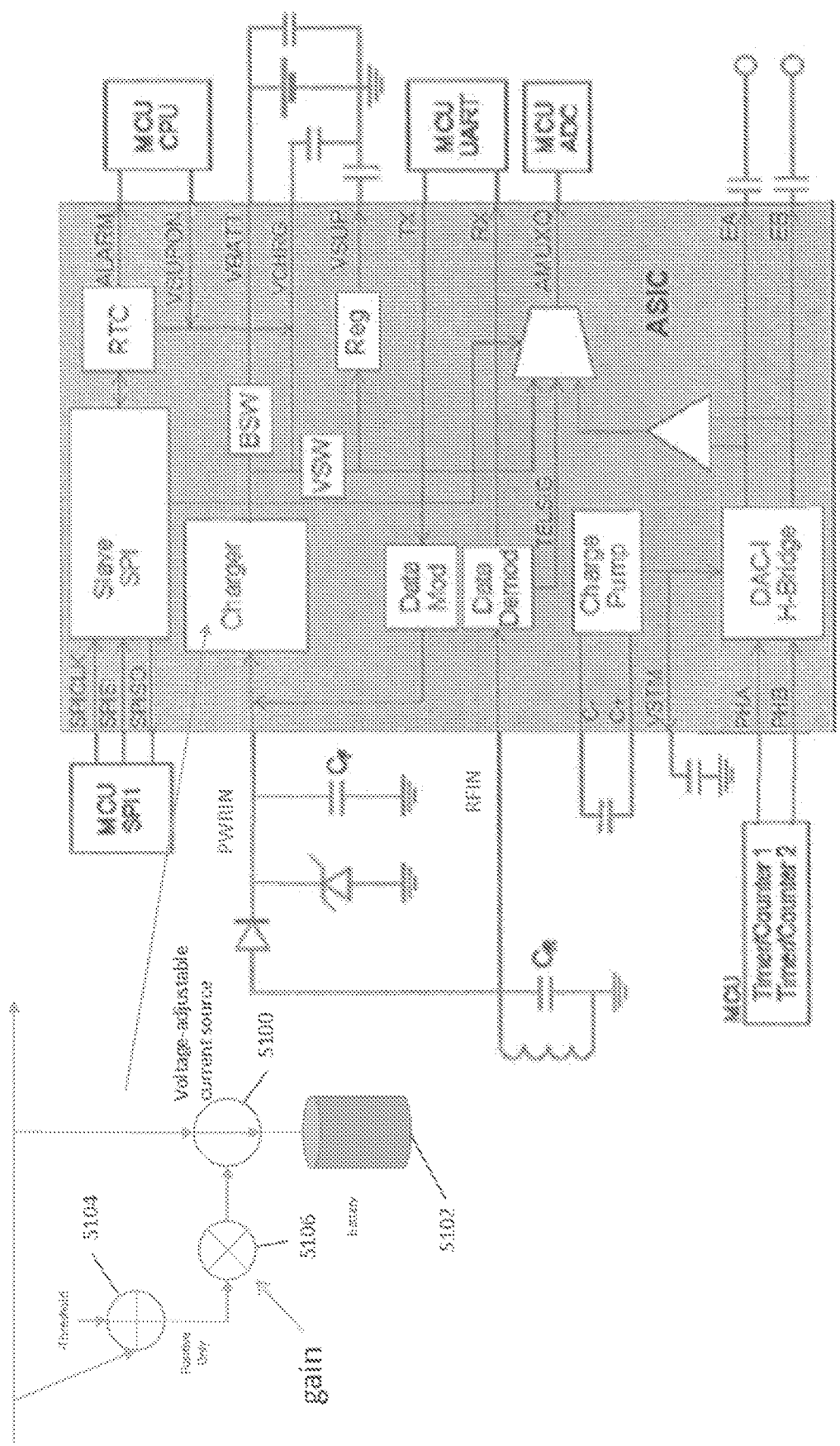
FIG. 17 illustrates another embodiment of a schematic of one variation of a controller for use in the microstimulator that includes a voltage-adjustable current source.

One embodiment for adjusting the current in the implant is to provide the implant with a voltage controlled current source in the charging circuit as shown in FIG. 17. The voltage controlled current source 5100 can adjust the current for charging the battery 5102 based on the antenna voltage of the implant, such that when the antenna voltage approaches and/or drops to or below a predetermined threshold, then the current is decreased or set to zero. If the antenna voltage is greater than a predetermined minimum operational threshold 5104, then the current can be increased by, for example, a multiplying factor 5106 based on the difference between the actual antenna voltage and the predetermined minimum operational threshold voltage multiplied by a gain. Below the predetermined minimum operational threshold, the current can be set to zero to preserve communication.

Prior art implants typically adjust the RF external power provided by the charger to meet the internal needs of the implant. In contrast, the implant described above is uniquely designed to modulate the power drawn by the implant, by throttling the current for example, given the RF external power provided by the charger. Such a configuration prioritizes communications over powering other functions of the implant, such as charging the battery, even though both functions may share the same circuit channel. Such a configuration also enables a "low power mode" which preserves communications even when the RF external power provided by the charger is relatively low.

Alternatively or additionally, an intermediate field communication link can be used instead of communicating through the power signal. The intermediate field communication link can be powered by the battery of the MR and use a high-gain amplifier to amplify the RF signal for transmission to the charger. This would allow the charger and MR to communicate at a longer range and enable more convenient pairing or initialization of the devices, such as before the charger is worn around the neck. For example, the patient can initiate communications while simply holding the charger in his hands, rather than having to wear the charger before initiating communications.

Figure 18:
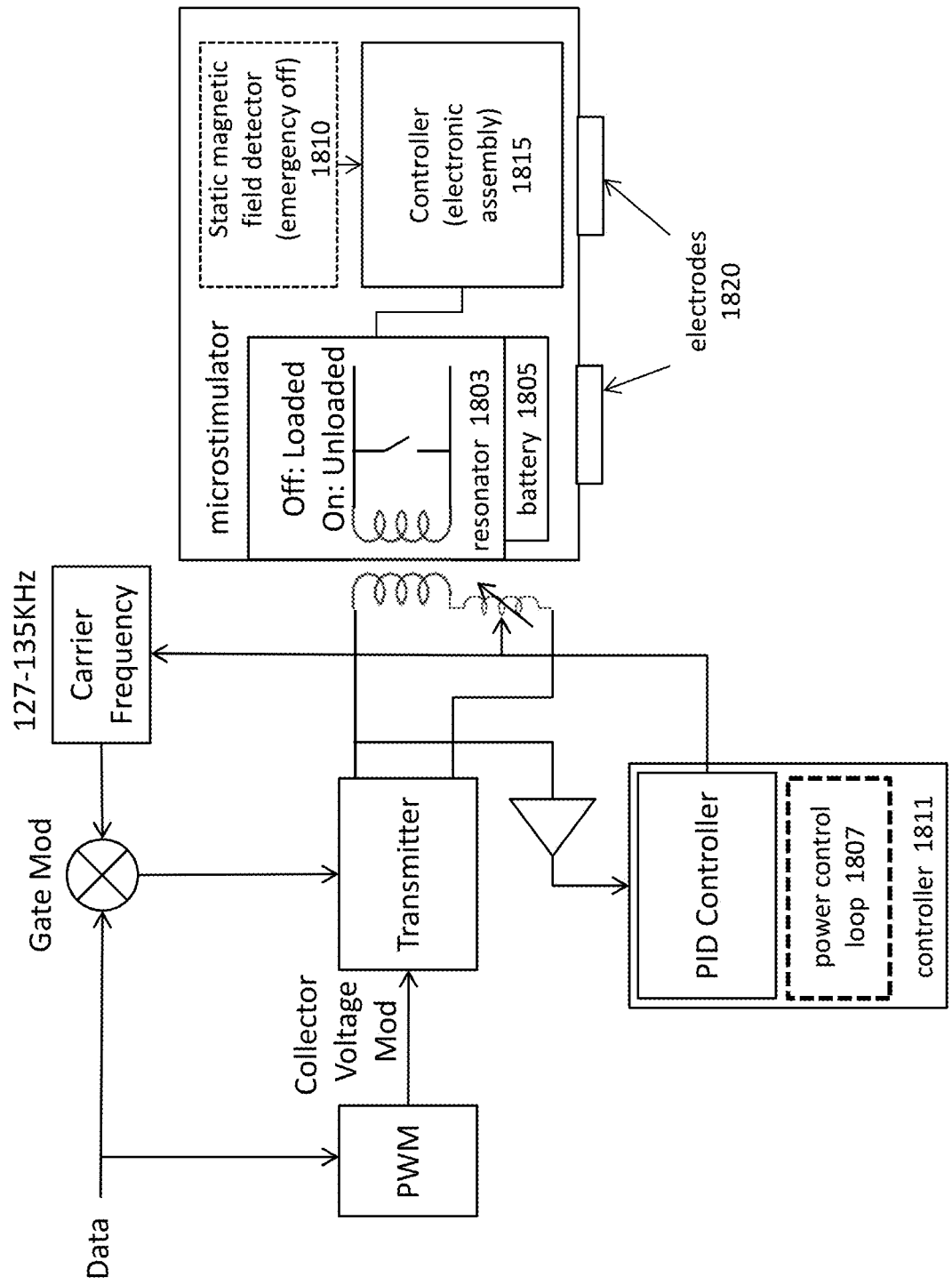
FIG. 18 schematically illustrates a system including a charger (on left) and a microstimulator implant (on right). The microcontroller may optionally include a static magnetic field detector and/or controller including adapted for regulating the power and therefore the temperature of the implant; the charger may likewise be adapted to adjust the applied energy to prevent overheating (e.g., based on the PWRIN from the microcontroller).

FIG. 18 schematically illustrates a charger and a microstimulator optionally incorporating both the static magnetic field detector (emergency off) 1810 and the power control loop 1807 in the charger (as part of the charger controller 1811), as discussed above. The controller may also include PID controller that uses the voltage across the two series inductors to control the carrier frequency and the inductance through a DC voltage that in turn varies the static flux in the variable inductor.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims. The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method to shut down an implantable microstimulator device for treating chronic inflammation by a static magnetic field, the method comprising:
   generating pulses by a low power pulse generator;
   introducing the pulses into a resonator of the implantable microstimulator device;
   monitoring a decay rate of the pulses using a detection circuit of the implantable microstimulator device; and
   shutting down the implantable microstimulator device when the decay rate increases to a predetermined threshold decay rate.

2. The method of claim 1, further comprising placing a magnet near the implantable microstimulator device.

3. The method of claim 1, wherein shutting down the implantable microstimulator device comprises shutting down the implantable microstimulator device when the predetermined threshold decay rate increases 2 times.

4. The method of claim 1, wherein introducing the pulses into the resonator comprises introducing the pulses into a built-in receiving coil, the built-in receiving coil configured to receive power from an external charger.

5. The method of claim 1, wherein shutting down the implantable microstimulator device comprises shutting down the implantable microstimulator device using a shorting switch configured to shut down the implantable microstimulator device.

6. The method of claim 1, wherein a power of the pulses is between 1 nanowatt and 10 microwatts.

7. The method of claim 1, wherein a power of the pulses is between 1 nanowatt and 1 microwatt.

8. The method of claim 1, wherein the pulses are introduced periodically.

9. The method of claim 1, wherein the resonator is a resonant circuit (RLC) resonator.

10. The method of claim 1, further comprising receiving power from the resonator to charge a battery of the implantable microstimulator device.

11. The method of claim 1, further comprising stimulating of a vagus nerve using the implantable microstimulator device.

12. A method of shutting down an implanted neurostimulator device using a static magnetic field, the method comprising:
    applying the static magnetic field of a predetermined amplitude to a region outside of a user's body near the implanted neurostimulator device;
    detecting the static magnetic field using a detection circuit that monitors a decay rate of pulses of a resonator in the implanted neurostimulator device; and
    shutting down the implanted neurostimulator device when the implanted neurostimulator device detects the static magnetic field.

13. The method of claim 12, wherein detecting the static magnetic field is performed without using a Hall effect sensor.

14. The method of claim 12, further comprising:
    generating the pulses by a low power pulse generator;
    introducing the pulses into the resonator;
    monitoring a decay rate of the pulses; and
    shutting down the implanted neurostimulator device when the decay rate increases to a predetermined threshold decay rate.

15. The method of claim 14, wherein shutting down the implanted neurostimulator device comprises shutting down the implanted neurostimulator device when the predetermined threshold decay rate increases 2 times.

16. The method of claim 12, wherein shutting down the implanted neurostimulator device comprises using a shorting switch to shut down the implanted neurostimulator device.

17. The method of claim 12, further comprising stimulating a vagus nerve using the implanted neurostimulator device.

18. The method of claim 12, further comprising generating an antenna voltage when power is inductively received from an external charger.

19. The method of claim 18, further comprising limiting power drawn by a battery based on the antenna voltage.

20. The method of claim 17, wherein stimulating the vagus nerve comprises apply stimulation in the presence of an inductive field.

* * * * *